(12) United States Patent
Cohen et al.

(10) Patent No.: US 10,226,517 B2
(45) Date of Patent: *Mar. 12, 2019

(54) DNA VACCINES ENCODING HEAT SHOCK PROTEINS

(71) Applicant: Alma Bio Therapeutics, Lyons (FR)

(72) Inventors: Irun R. Cohen, Rehovot (IL); Francisco J. Quintana, Capital Federal (AR); Pnina Carmi, Rehovot (IL); Felix Mor, Kfar Saba (IL)

(73) Assignee: Alma Bio Therapeutics, Lyons (FR)

( * ) Notice: Subject to any disclaimer, the term of this patent is extended or adjusted under 35 U.S.C. 154(b) by 0 days.

This patent is subject to a terminal disclaimer.

(21) Appl. No.: 15/957,625

(22) Filed: Apr. 19, 2018

(65) Prior Publication Data

US 2018/0236052 A1    Aug. 23, 2018

Related U.S. Application Data

(60) Continuation of application No. 15/012,540, filed on Feb. 1, 2016, now Pat. No. 9,974,843, which is a continuation of application No. 14/507,648, filed on Oct. 6, 2014, now Pat. No. 9,283,265, which is a continuation of application No. 13/720,088, filed on Dec. 19, 2012, now abandoned, which is a division of application No. 13/293,722, filed on Nov. 10, 2011, now Pat. No. 8,361,987, which is a continuation of application No. 12/396,401, filed on Mar. 2, 2009, now Pat. No. 8,058,254, which is a division of application No. 10/994,152, filed on Nov. 19, 2004, now abandoned, which is a continuation of application No. PCT/IL03/00417, filed on May 21, 2003.

(60) Provisional application No. 60/381,821, filed on May 21, 2002.

(51) Int. Cl.
| A61K 39/00 | (2006.01) |
| A61K 31/7088 | (2006.01) |
| A61K 38/17 | (2006.01) |
| A61K 48/00 | (2006.01) |

(52) U.S. Cl.
CPC ...... *A61K 39/0008* (2013.01); *A61K 31/7088* (2013.01); *A61K 38/1709* (2013.01); *A61K 39/00* (2013.01); *A61K 48/00* (2013.01); *A61K 2039/53* (2013.01); *A61K 2039/54* (2013.01); *A61K 2039/545* (2013.01); *A61K 2039/57* (2013.01)

(58) Field of Classification Search
CPC .................. A61K 39/0008; A61K 31/7088
See application file for complete search history.

(56) References Cited

U.S. PATENT DOCUMENTS

| 5,993,803 | A | 11/1999 | Cohen et al. |
| 6,007,821 | A | 12/1999 | Srivastava et al. |
| 6,316,420 | B1 | 11/2001 | Karin et al. |
| 6,884,785 | B2 | 4/2005 | von Herrath |
| 9,283,265 | B2 * | 3/2016 | Cohen ............... A61K 38/1709 |
| 9,974,843 | B2 | 5/2018 | Cohen et al. |
| 2001/0031264 | A1 | 10/2001 | Segal |
| 2002/0150586 | A1 | 10/2002 | Naparstek et al. |
| 2003/0171280 | A1 | 9/2003 | Soderstrom |
| 2003/0190323 | A1 | 10/2003 | Cohen et al. |
| 2004/0022869 | A1 * | 2/2004 | Chen ................... A61K 31/337 424/623 |
| 2006/0089302 | A1 | 4/2006 | Abulafia-Lapid et al. |

FOREIGN PATENT DOCUMENTS

| EP | 0262710 | 4/1988 | |
| EP | 0322990 | 7/1989 | |
| WO | WO 1992/04049 | 3/1992 | |
| WO | WO 1997/01959 | 1/1997 | |
| WO | WO 1997/02016 | 1/1997 | |
| WO | 1999/018801 | 4/1999 | |
| WO | WO1999/018801 | * 4/1999 | ............ A01N 63/00 |
| WO | WO 1999/18801 | 4/1999 | |
| WO | WO 2000/27870 | 5/2000 | |
| WO | WO 2001/16174 | 3/2001 | |
| WO | WO 2001/17554 | 3/2001 | |
| WO | WO 2001/23421 | 4/2001 | |
| WO | WO 2001/57056 | 8/2001 | |
| WO | WO 2002/16549 | 2/2002 | |
| WO | WO 2003/026579 | 4/2003 | |
| WO | WO 2005/048914 | 6/2005 | |

OTHER PUBLICATIONS

Mor et al. (Human Gene Therapy. 1997; 8: 293-300) (Year: 1997).*
Gurunathan et al (Annu. Rev . Immunol. 2000; 18: 927-974). (Year: 2000).*
Abulafia-Lapid et al. (1999) "T cell proliferative responses of type 1 diabetes patients and healthy individuals to human hsp60 and its peptides," *J Autoimmun.*; 12(2):121-129.
Anderton et al. (1995) "Activation of T Cells Recognizing Self 60-kD Heat Shock Protein Can Protect Against Experimental Arthritis," *J. Exp Med.*; 181:943-952.
Anderton et al. (1994) "Differential Mycobacterial 60-kDa Heat-Shock Protein T Cell Epitope Recognition After Adjuvant Arthritis-Inducing or Protective Immunization Protocols," *Journal of Immunology*; 152:3656-3664.

(Continued)

*Primary Examiner* — Scott Long
(74) *Attorney, Agent, or Firm* — Carol L. Francis; Bozicevic, Field & Francis LLP

(57) ABSTRACT

A method of treating a T cell-mediated inflammatory autoimmune disease by administering to an individual in need thereof an immunogenic composition comprising a recombinant construct of a nucleic acid sequence encoding heat shock protein 90 (HSP 90), or an active fragment thereof, wherein the nucleic acid sequence is operatively linked to one or more transcription control sequences. The disease is other than insulin dependent diabetes mellitus (IDDM) or rheumatoid arthritis. The administering of the immunogenic composition results in a shift of the immune response to a Th2 response, thereby treating the disease.

15 Claims, 21 Drawing Sheets

Specification includes a Sequence Listing.

(56) References Cited

OTHER PUBLICATIONS

Bellmann et al. (1996) "Heat shock protein hsp70 overexpression confers resistance against nitric oxide," *FEBS Letters*; 391:185-188.
Benhamou et al. (1998) "Strategies for Graft Immunomodulation in Islet Transplantation," *Diabetes & Metabolism* ; (Paris); 24:215-224.
Billingham et al. (1990) "A Mycobacterial65-kD Heat Shock Protein Induces Antigen-Specific Suppression of Adjuvant Arthritis, But Is Not Itself Arthritogenic," *J. Exp. Med.*; 171;334-339.
Boog et al. (1992) "Two Monoclonal Antibodies Generated Against Human hsp60 Show Reactivity With Synovial Membranes OfPatients With Juvenile Chronic Arthritis," *J. Exp. Med*; 175:1805-1810.
Borges et al. (2012) "The anti-inflammatory mechanisms of Hsp70," *Frontiers in Immunology*; 3:95.
Chen et al. (2000) "Enhancement of DNA Vaccine Potency by Linkage of Antigen Gene to an HSP70 Gene" *Cancer Research*; 60:1035-1042.
Chen et al. (2005) "The HSP90 family of genes in the human genome: Insights into their divergence and evolution," *Genomics*; 86:627-637.
Chernajovsky et al. (1997) "Pathogenic Lymphoid Cells Engineered to Express Tgf Beta1 Ameliorate Disease in a Collagen-Induced Arthritis," *Gene Therapy*; 4(6):553-559.
Cohen (2000) "Discrimination and Dialogue in the Immune System," *Seminars in Immunology*; 12(3):215-219.
Corr et al. (1999) "In Vivo Priming by DNA Injection Occurs Predominantly by Antigen Transfer," *The Journal of Immunology*; 163:4721-4727.
Csermely et al. (1998) "The 90-kDa Molecular Chaperone Family: Structure, Function, and Clinical Applications. A Comprehensive Review," *Pharmacal. Ther.*; 79(2):129-168.
Denis et al. (1998) "Vaccination with plasmid DNA encoding mycobacterial antigen 85A stimulates a CD4+ and CDS+ T-cell epitopic repertoire broader than that stimulated by *Mycobacterium tuberculosis* H37Rv infection," *Infection and Immunity*; 66(4):1527-1533.
Dietz et al. (1998) "High Efficiency Adenovirus-Mediated Gene Transfer to Human Dendritic Cells," (*Blood*; 91(2):392-398.
Ditzian-Kadanoff (1999) "Testicular-Associated Immune Deviation and Prevention of Adjuvant-Induced Arthritis by Three Tolerization Methods," *Scandanavian Journal of Immunology*; 50(2):150-158.
Elias et al. (1990) "Induction and therapy of autoimmune diabetes in the non-obese diabetic (NOD/Lt) mouse by a 65-kDa heat shock protein," *PNAS*; 87:1576-1580.
Elias et al. (1991) "Vaccination against autoimmune mouse diabetes with a T-cell epitope of the human 65-kDa heat shock protein," *Proc. National Academy Science, USA*; 88(8):3088-3091.
Elias et al. (1999) "Regulation of NOD mouse autoimmune diabetes by T cells that recognize a TCR CDR3 peptide," *International Immunology*; 11(6):957-966.
Giomi et al. (2002) "Th1, Th2 and Th3 Cytokines in the Pathogenesis of Bullous Pemphigoid," *J Dermato. Sci*; 30(2):116-128.
Haque et al. (1996) "Suppression of Adjuvant Arthritis in Rats by Induction of Oral Tolerance to Mycobacterial 65-Kda Heat Shock Protein," *European Journal Immunology*; vol. 26(11):2650-2656.
Heiser et al. (2002) "Autologous Dendritic Cells Transfected with Prostate-Specific Antigen Rna C3 Stimulate CTL Responses Against Metastatic Prostate Tumors," *I. Clin. Invest.*; 109:409-417.
Hermans et al. (1999) "Cellular and Humoral Immune Responses Against Autoreactive T-cells in Multiple Sclerosis Patients After T cell Vaccination," *Journal of Autoimmunity*; 13(2):233-246.
Hermans et al. (2000) "Myelin Reactive T Cells After T Cell Vaccination in Multiple Sclerosis: Cytokine Profile and Depletion by Additional Immunizations," *Journal of Neuroimmunology*; 102(1):79-84.
Hogervorst et al. (1991) "Modulation of Experimental Autoimmunity: Treatment of Adjuvant Arthritis by Immunization With a Recombinant Vaccinia Virus," *Infection and Immunity*; 59(6):2029-2035.

Holoshitz et al. (1984) "Arthritis Induced in Rats by Cloned T Lymphocytes Responsive to Mycobacteria But Not to Collage Type IT," *J. Chin Invest.*; 73:211-215.
Holoshitz et al. (1983) "Lines OfT Lymphocytes Induce or Vaccinate Against Autoimmune Arthritis," *Science*; 219:56-58.
Invitrogen pcDNA3 sequence, Jul. 1, 1995.
Kingston et al. (1996) "A 71-Kd Heat Shock Protein (Hsp) From *Mycobacterium tuberculosis* Has Modulatory Effects on Experimental Rat Arthritis," *Clinical and Experimental Immunology*; 103(1):77-82.
Kroemer et al. (1996) "Differential Involvement OfTh1 and Th2 Cytokines in Autoimmune Diseases," *Autoimmunity*; 24:25-33.
Kumar et al. (2001) "Induction of a type 1 regulatory CD4 T cell response following V beta 8.2 DNA vaccination results in immune deviation and protection from experimental autoimmune encephalomyelitis," *International Immunology*; 13(6):835-841.
Lanza et al. (1997) "Transplantation of encapsulated cells and tissues," *Surgery*, 121(1):1-9.
Li, et al.(1993) "Tumor Rejection Antigen Gp96/Grp94 is an Atpase: Implications for Protein Folding and Antigen Presentation," *The EMBO Journal*; 12(8):3143-3151.
Lopez-Guerrero et al. (1993) "Modulation of Adjuvant Arthritis in Lewis Rats by Recombinant Vaccinia Virus Expressing the Human 60-Kilodalton Heat Shock Protein," *Infection and Immunity*; 61:4225-4231.
Lopez-Guerrero et al. (1994) "Therapeutic Effect of Recombinant Vaccinia Virus Expressing the 60-kD Heat-Shock Protein on Adjuvant Arthritis," *Arthritis Rheumatism*; 37(1 0): 1462-1467.
Manickan et al. (1997) "Enhancement of immune response to naked DNA vaccine by immunization with transfected dendritic cells," *J. Leukoc. Biol.*; 61:125-132.
Menoret et al. (2002) "Natural Autoantibodies Against Heat-Shock Proteins Hsp70 and Gp96: Implications for Immunotherapy Using Heat-Shock Proteins," *Immunology*; 101:364-370.
Mor et al. (1997) "Do DNA Vaccines Induce Autoimmune Disease?" *Human Gene Therapy*; 8:293-300.
Moudgil et al. (2001) "Environmental Modulation of Autoimmune Arthritis Involves the Spontaneous Microbial Induction Oft Cell Responses to Regulatory Determinants Within Heat Shock Protein 65," *The Journal of Immunology*; 166(6):4237-4244.
Moudgil (1997) "Diversification Of T-Cell Responses to Carboxy-Terminal Determinants Within the 65-kD Heat-Shock Protein Is Involved in Regulation of Autoimmune Arthritis," *J Exp Med*; 185(7):I307-1316.
Mumper et al. (2001) "Dendritic Cell Delivery of Plasmid DNA," *Molecular Biotechnology*; 19:79-95.
Nemoto et al. (1997) "Domain Structures and Immunogenic Regions of the 90-Kda Heat-Shock Protein (HSP90). Probing With a Library Ofanti-Hsp90 Monoclonal Antibodies and Limited Proteolysis," *J Biol Chem*; 272(42):26179-26187.
Nemoto et al. (2001) "Substrate-Binding Characteristics of Proteins in the 90 Kda Heat Shock Protein Family," *Biochem. J*; 354:663-670.
Olson et al. (2001) "Virus-induced autoimmunity: potential role of viruses in initiation, perpetuation, and progression of T-cell-mediated autoimmune disease" *ViralImmunol*; 14(3):227-250.
Paul (2000) "Highly Autoproliferative T Cells Specific for 60-Kda Heat Shock Protein Produce II-4/II-1 0 and Ifn-Gamma and Are Protective in Adjuvant Arthritis," *The Journal of Immunology*; 165(12):7270-7277.
Phipps et al. (2003) "Prevention of Mucosally Induced Uveitis With a Hsp60-Derived Peptide Linked to Cholera Toxin B Subunit," *Eur J Immunol.*; 33(1):224-232.
Prakken et al. (2002) "Heat Shock Proteins in Juvenile Idiopathic Arthritis: Keys for Understanding Remitting Arthritis and Candidate Antigens for Immune Therapy," *Current Rheumatology Reports*; 4:466-473.
Prakken (1997) "T-Cell Reactivity to Human Hsp60 in Oligo-Articular Juvenile Chronic Arthritis is Associated With a Favorable Prognosis and the Generation of Regulatory Cytokines in the Inflamed Joint," *Immunology Letters*; 57:139-142.

(56) References Cited

OTHER PUBLICATIONS

Prakken et al. (2001) "Induction of II-10 and Inhibition of Experimental Arthritis are Specific Features of Microbial Heat Shock Proteins That are Absent for Other Evolutionarily Conserved Immunodominant Proteins," *The Journal of Immunology*; 167(8):4147-4153.
Prodromou et al. (2000) "The 90-kDa Molecular Chaperone Family: Structure, Function, and Clinical Applications. A Comprehensive Review," *The EMBO Journal*; 19(16): 4383-4392.
Prud'Homme and Piccirillo (2000) "The Inhibitory Effects of Transforming Growth Factor-Beta-1 (TGF-131)in Autoimmune Diseases," *Journal of Autoimmunity*; 14(1):23-42.
Quattrocchi et al. (2001) "Murine II-10 Gene Transfer Inhibits Established Collagen-Induced Arthritis and Reduces Adenovirus-Mediated Inflammatory Responses in Mouse Liver," *The Journal of Immunology*; 166(10): 5970-5978.
Quintana et al. (2000) "Vaccination With Empty Plasmid DNA or CpG Oligonucleotide Inhibits Diabetes in Nonobese Diabetic Mice. Modulation of Spontaneous 60-KDa Heat Shock Protein Autoimmnnity1," *Journal of Immunology*; 165:6148-6155.
Quintana et al. (2002) "Inhibition of Adjuvant Arthritis by a DNA Vaccine Encoding Human Heat Shock Protein 601," *Journal of Immunology*, 169:3422-3428.
Ragno et al. (1997) "Protection of Rats From Adjuvant Arthritis by Immunization With Naked DNA Encoding for Mycobacterial Heat Shock Protein 65," *Arthritis Rheumatism*; 40(2):277-283.
Ragno et al. (1996) "A Synthetic 1 0-Kd Heat Shock Protein (Hsp1 0) From *Mycobacterium tuberculosis* Modulates Adjuvant Arthritis," *Clinical and Experimental Immunology*; 103(3):384-390.
Raz et al. (2001) "Beta-Cell Function in New-Onset Type 1 Diabetes and Immunomodulation With a Heat-Shock Protein Peptide (DiaPep277): A Randomised, Double-Blind, Phase li Trial," *Lancet*; 358(9295):1749-1753.
Schwartz and Cohen (2000) "Autoimmunity Can Benefit Self-Maintenance," *Immunology Today*; 21(6):265-268.
Setoguchi et al. (2000) "Antigen-Specific T Cells Transduced With II-10 Ameliorate Experimentally Induced Arthritis Without Impairing the Systemic Immune Response to the Antigen," *The Journal of Immunology*; 165(1 0): 5980-5986.
Srivastava et al. (2003) "Gene Vaccines," *Annals of Internal Medicine*; 138(7):550-559.
Storni et al. (2004) "Loading of Mhc Class I and II Presentation Pathways by Exogenous Antigens: A Quantitative in Vivo Comparison," *J. Immunol.*; 172:6129-6135.
Suzue et al. (1996) "Adjuvant-Free Hsp70 Fusion Protein System Elicits Humoral and Cellular Immune Responses to Hiv-1 P24," *Journal of Immunology*; 156:873-879.
Tanaka et al. (1999) "Activation ofT Cells Recognizing an Epitope of Heat-Shock Protein 70 Can Protect Against Rat Adjuvant Arthritis," *The Journal of Immunology*; 163(1 0):5560-5565.
Tavaria et al. (1996) "A Hitchhiker's Guide to the Human Hsp70 Family," *Cell Stress & Chaperones*; 1(1)23-28.
Udono et al. (1993) "Heat Shock Protein 70-associated Peptides Elicit Specific Cancer Immunity" *J. Exp. Med.*; 178:1391-1396.
Van Der Zee et al. (1988) "T-Cell Responses to Conserved Bacterial Heat-Shock-Protein Epitopes Induce Resistance in Experimental Autoimmunity," *Seminars in Immunology*; 10(1): 35-41.
Van Eden et al. (2003) "Immunopotentiating heat shock proteins: negotiators between innate danger and control of autoimmunity," *Vaccine*; 21:897-901.
Van Eden et al. (1998) "Do Heat Shock Proteins Control the Balance of T -Cell Regulation in Inflammatory Diseases?" *Immunology Today*; 19(7):303-307.
Van Eden et al. (1985) "Arthritis Induced by a T-Lymphocyte Clone That Responds to *Mycobacterium tuberculosis* and to Cartilage Proteoglycans," *Proc. Natl. Acad Sci USA*; 82:5117-5120.
Van Eden et al. "Cloning of the Mycobacterial Epitope Recognized by T Lymphocytes in Adjuvant Arthritis," *Nature*; 331(6152):171-173.
Van Eden et al. (2000) "Arthritis Protective Regulatory Potential of Self-Heat Shock Protein Cross-Reactive T Cells," *Cell Stress & Chaperones*; 5(5): 452-457.
Van Halteren et al. (2002) "Cross-Reactive Mycobacterial and Self hsp60 Epitope Recognition in 1-A Expressing NOD, NOD-asp and Biozzi AB/H Mice," *Journal of Autoimmunity*; 18:139-147.
Van Molle et al. (2002) "HSP70 Protects against TNF-Induced Lethal Inflammatory Shock," *Immunity*; 16:685-695.
Van Roon et al. (1997) "Stimulation of Suppressive T Cell Responses by Human but Not Bacterial 60-Kd Heat-Shock Protein in Synovial Fluid of Patients with Rheumatoid Arthritis," *Journal of Clinical Investigation*; 100(2):459-463.
Van Tienhoven et al. (2001) "Induction of Antigen Specific Cd4+ T Cell Responses by Invariant Chain Based DNA Vaccines," *Vaccine*; 19:1515-1519.
Venner et al. (1990) "Nucleotide Sequences and Novel Structural Features of Human and Chinese Hamster hsp60 (Chaperonin) Gene Families" *DNA Cell Bioi.*; 9(8):545-552.
Waisman (1996) "Suppressive Vaccination with Dna Encoding a Variable Region Gene of the T-Cell Receptor Prevents Autoimmune Encephalomyelitis and Activates Th2 Immunity," *Nature Medicine*; 2(8):899-905.
Wendling et al. (2000) "A Conserved Mycobacterial Heat Shock Protein (hsp) 70 Sequence Prevents Adjuvant Arthritis upon Nasal Administration and Induces IL-I 0-Producing T Cells that Cross-React with the Mammalian Self-hsp70 Homologue," *The Journal of Immunology*; 164:2711-2717.
Yang et al. (1992) "Prevention of Adjuvant Arthritis in Rats by a Nonapeptide From the 65-kD Mycobacterial Heat Shock Protein: Specificity and Mechanism," *Clin. Exp Immunol.*; 87:99-104.
Kinner-Bibeau, Lauren, B., et al., (2017) "HSPs drive dichotomous T-cell immune responses via DNA methylome remodelling in antigen presenting cells", Nature Communications, 13 pages.
Van Den Broek, Maries, F., et al., (1989) "Protection Against Streptococcal Cell Wall-Induced Arthritis by Pretreatment With the 65-kD Mycobacterial Heat Shock Protein", J. Exp. Med., 170:449-466.
Gurunathan et al., (2000) "DNA Vaccines: Immunology, Application, and Optimization", Annu. Rev. Immunol., 18:927-974.

\* cited by examiner

A

B

A

B

C

```
                        SEQUENCE LISTING

<160> NUMBER OF SEQ ID NOS: 35

<210> SEQ ID NO 1
<211> LENGTH: 140
<212> TYPE: PRT
<213> ORGANISM: Homo sapiens

<400> SEQUENCE: 1

Met Leu Arg Leu Pro Thr Val Phe Arg Gln Met Arg Pro Val Ser Arg
1               5                   10                  15

Val Leu Ala Pro His Leu Thr Arg Ala Tyr Ala Lys Asp Val Lys Phe
            20                  25                  30

Gly Ala Asp Ala Arg Ala Leu Met Leu Gln Gly Val Asp Leu Leu Ala
        35                  40                  45

Asp Ala Val Ala Val Thr Met Gly Pro Lys Gly Arg Thr Val Ile Ile
    50                  55                  60

Glu Gln Gly Trp Gly Ser Pro Lys Val Thr Lys Asp Gly Val Thr Val
65                  70                  75                  80

Ala Lys Ser Ile Asp Leu Lys Asp Lys Tyr Lys Asn Ile Gly Ala Lys
                85                  90                  95

Leu Val Gln Asp Val Ala Asn Asn Thr Asn Glu Glu Ala Gly Asp Gly
            100                 105                 110

Thr Thr Thr Ala Thr Val Leu Ala Arg Ser Ile Ala Lys Glu Gly Phe
        115                 120                 125

Glu Lys Ile Ser Lys Gly Ala Asn Pro Val Glu Ile
    130                 135                 140

<210> SEQ ID NO 2
<211> LENGTH: 131
<212> TYPE: PRT
<213> ORGANISM: Homo sapiens

<400> SEQUENCE: 2

Lys Ile Ser Lys Gly Ala Asn Pro Val Glu Ile Arg Arg Gly Val Met
1               5                   10                  15

Leu Ala Val Asp Ala Val Ile Ala Glu Leu Lys Lys Gln Ser Lys Pro
            20                  25                  30

Val Thr Thr Pro Glu Glu Ile Ala Gln Val Ala Thr Ile Ser Ala Asn
        35                  40                  45
```

Gly Asp Lys Glu Ile Gly Asn Ile Ile Ser Asp Ala Met Lys Lys Val
 50                  55                  60

Gly Arg Lys Gly Val Ile Thr Val Lys Asp Gly Lys Thr Leu Asn Asp
 65                  70                  75                  80

Glu Leu Glu Ile Ile Glu Gly Met Lys Phe Asp Arg Gly Tyr Ile Ser
                 85                  90                  95

Pro Tyr Phe Ile Asn Thr Ser Lys Gly Gln Lys Cys Glu Phe Gln Asp
                100                 105                 110

Ala Tyr Val Leu Leu Ser Glu Lys Lys Ile Ser Ser Ile Gln Ser Ile
            115                 120                 125

Val Pro Ala
    130

<210> SEQ ID NO 3
<211> LENGTH: 20
<212> TYPE: PRT
<213> ORGANISM: Homo sapiens

<400> SEQUENCE: 3

Lys Phe Gly Ala Asp Ala Arg Ala Leu Met Leu Gln Gly Val Asp Leu
1                   5                  10                  15

Leu Ala Asp Ala
            20

<210> SEQ ID NO 4
<211> LENGTH: 641
<212> TYPE: PRT
<213> ORGANISM: Homo sapiens

<400> SEQUENCE: 4

Met Ala Lys Ala Ala Ile Gly Ile Asp Leu Gly Thr Thr Tyr Ser
1                   5                  10                  15

Cys Val Gly Val Phe Gln His Gly Lys Val Glu Ile Ile Ala Asn Asp
                 20                  25                  30

Gln Gly Asn Arg Thr Thr Pro Ser Tyr Val Ala Phe Thr Asp Thr Glu
             35                  40                  45

Arg Leu Ile Gly Asp Ala Ala Lys Asn Gln Val Ala Leu Asn Pro Gln
 50                  55                  60

Asn Thr Val Phe Asp Ala Lys Arg Leu Ile Gly Arg Lys Phe Gly Asp
 65                  70                  75                  80

Pro Val Val Gln Ser Asp Met Lys His Trp Pro Phe Gln Val Ile Asn
                 85                  90                  95

Asp Gly Asp Lys Pro Lys Val Gln Val Ser Tyr Lys Gly Glu Thr Lys
                100                 105                 110

Ala Phe Tyr Pro Glu Glu Ile Ser Ser Met Val Leu Thr Lys Met Lys
            115                 120                 125

Glu Ile Ala Glu Ala Tyr Leu Gly Tyr Pro Val Thr Asn Ala Val Ile
            130                 135                 140

Thr Val Pro Ala Tyr Phe Asn Asp Ser Gln Arg Gln Ala Thr Lys Asp
145                 150                 155                 160

Ala Gly Val Ile Ala Gly Leu Asn Val Leu Arg Ile Ile Asn Glu Pro
                165                 170                 175

Thr Ala Ala Ala Ile Ala Tyr Gly Leu Asp Arg Thr Gly Lys Gly Glu
            180                 185                 190

Arg Asn Val Leu Ile Phe Asp Leu Gly Gly Gly Thr Phe Asp Val Ser
        195                 200                 205

```
Ile Leu Thr Ile Asp Asp Gly Ile Phe Glu Val Lys Ala Thr Ala Gly
210                 215                 220

Asp Thr His Leu Gly Gly Glu Asp Phe Asp Asn Arg Leu Val Asn His
225                 230                 235                 240

Phe Val Glu Glu Phe Lys Arg Lys His Lys Lys Asp Ile Ser Gln Asn
            245                 250                 255

Lys Arg Ala Val Arg Arg Leu Arg Thr Ala Cys Glu Arg Ala Lys Arg
            260                 265                 270

Thr Leu Ser Ser Ser Thr Gln Ala Ser Leu Glu Ile Asp Ser Leu Phe
        275                 280                 285

Glu Gly Ile Asp Phe Tyr Thr Ser Ile Thr Arg Ala Arg Phe Glu Glu
290                 295                 300

Leu Cys Ser Asp Leu Phe Arg Ser Thr Leu Glu Pro Val Glu Lys Ala
305                 310                 315                 320

Leu Arg Asp Ala Lys Leu Asp Lys Ala Gln Ile His Asp Leu Val Leu
            325                 330                 335

Val Gly Gly Ser Thr Arg Ile Pro Lys Val Gln Lys Leu Leu Gln Asp
            340                 345                 350

Phe Phe Asn Gly Arg Asp Leu Asn Lys Ser Ile Asn Pro Asp Glu Ala
        355                 360                 365

Val Ala Tyr Gly Ala Ala Val Gln Ala Ala Ile Leu Met Gly Asp Lys
370                 375                 380

Ser Glu Asn Val Gln Asp Leu Leu Leu Leu Asp Val Ala Pro Leu Ser
385                 390                 395                 400

Leu Gly Leu Glu Thr Ala Gly Gly Val Met Thr Ala Leu Ile Lys Arg
            405                 410                 415

Asn Ser Thr Ile Pro Thr Lys Gln Thr Gln Ile Phe Thr Thr Tyr Ser
            420                 425                 430

Asp Asn Gln Pro Gly Val Leu Ile Gln Val Tyr Glu Gly Glu Arg Ala
        435                 440                 445

Met Thr Lys Asp Asn Asn Leu Leu Gly Arg Phe Glu Leu Ser Gly Ile
450                 455                 460

Pro Pro Ala Pro Arg Gly Val Pro Gln Ile Glu Val Thr Phe Asp Ile
465                 470                 475                 480

Asp Ala Asn Gly Ile Leu Asn Val Thr Ala Thr Asp Lys Ser Thr Gly
            485                 490                 495

Lys Ala Asn Lys Ile Thr Ile Thr Asn Asp Lys Gly Arg Leu Ser Lys
            500                 505                 510

Glu Glu Ile Glu Arg Met Val Gln Glu Ala Glu Lys Tyr Lys Ala Glu
        515                 520                 525

Asp Glu Val Gln Arg Glu Arg Val Ser Ala Lys Asn Ala Leu Glu Ser
530                 535                 540

Tyr Ala Phe Asn Met Lys Ser Ala Val Glu Asp Glu Gly Leu Lys Gly
545                 550                 555                 560

Lys Ile Ser Glu Ala Asp Lys Lys Lys Val Leu Asp Lys Cys Gln Glu
            565                 570                 575

Val Ile Ser Trp Leu Asp Ala Asn Thr Leu Ala Glu Lys Asp Glu Phe
            580                 585                 590

Glu His Lys Arg Lys Glu Leu Glu Gln Val Cys Asn Pro Ile Ile Ser
        595                 600                 605

Gly Leu Tyr Gln Gly Ala Gly Gly Pro Gly Pro Gly Gly Phe Gly Ala
610                 615                 620
```

```
Gln Gly Pro Lys Gly Gly Ser Gly Ser Gly Pro Thr Ile Glu Glu Val
625                 630                 635                 640

Asp
```

<210> SEQ ID NO 5
<211> LENGTH: 641
<212> TYPE: PRT
<213> ORGANISM: Homo sapiens

<400> SEQUENCE: 5

```
Met Ala Lys Ala Ala Ile Gly Ile Asp Leu Gly Thr Thr Tyr Ser
1               5                   10                  15

Cys Val Gly Val Phe Gln His Gly Lys Val Glu Ile Ile Ala Asn Asp
                20                  25                  30

Gln Gly Asn Arg Thr Thr Pro Ser Tyr Val Ala Phe Thr Asp Thr Glu
            35                  40                  45

Arg Leu Ile Gly Asp Ala Ala Lys Asn Gln Val Ala Leu Asn Pro Gln
    50                  55                  60

Asn Thr Val Phe Asp Ala Lys Arg Leu Ile Gly Arg Lys Phe Gly Asp
65                  70                  75                  80

Pro Val Val Gln Ser Asp Met Lys His Trp Pro Phe Gln Val Ile Asn
                85                  90                  95

Asp Gly Asp Lys Pro Lys Val Gln Val Ser Tyr Lys Gly Glu Thr Lys
            100                 105                 110

Ala Phe Tyr Pro Glu Glu Ile Ser Ser Met Val Leu Thr Lys Met Lys
        115                 120                 125

Glu Ile Ala Glu Ala Tyr Leu Gly Tyr Pro Val Thr Asn Ala Val Ile
    130                 135                 140

Thr Val Pro Ala Tyr Phe Asn Asp Ser Gln Arg Gln Ala Thr Lys Asp
145                 150                 155                 160

Ala Gly Val Ile Ala Gly Leu Asn Val Leu Arg Ile Ile Asn Glu Pro
                165                 170                 175

Thr Ala Ala Ala Ile Ala Tyr Gly Leu Asp Arg Thr Gly Lys Gly Glu
            180                 185                 190

Arg Asn Val Leu Ile Phe Asp Leu Gly Gly Gly Thr Phe Asp Val Ser
        195                 200                 205

Ile Leu Thr Ile Asp Asp Gly Ile Phe Glu Val Lys Ala Thr Ala Gly
    210                 215                 220

Asp Thr His Leu Gly Gly Glu Asp Phe Asp Asn Arg Leu Val Asn His
225                 230                 235                 240

Phe Val Glu Glu Phe Lys Arg Lys His Lys Lys Asp Ile Ser Gln Asn
                245                 250                 255

Lys Arg Ala Val Arg Arg Leu Arg Thr Ala Cys Glu Arg Ala Lys Arg
            260                 265                 270

Thr Leu Ser Ser Ser Thr Gln Ala Ser Leu Glu Ile Asp Ser Leu Phe
        275                 280                 285

Glu Gly Ile Asp Phe Tyr Thr Ser Ile Thr Arg Ala Arg Phe Glu Glu
    290                 295                 300

Leu Cys Ser Asp Leu Phe Arg Ser Thr Leu Glu Pro Val Glu Lys Ala
305                 310                 315                 320

Leu Arg Asp Ala Lys Leu Asp Lys Ala Gln Ile His Asp Leu Val Leu
                325                 330                 335

Val Gly Gly Ser Thr Arg Ile Pro Lys Val Gln Lys Leu Leu Gln Asp
            340                 345                 350
```

```
Phe Phe Asn Gly Arg Asp Leu Asn Lys Ser Ile Asn Pro Asp Glu Ala
            355                 360                 365

Val Ala Tyr Gly Ala Ala Val Gln Ala Ala Ile Leu Met Gly Asp Lys
    370                 375                 380

Ser Glu Asn Val Gln Asp Leu Leu Leu Asp Val Ala Pro Leu Ser
385                 390                 395                 400

Leu Gly Leu Glu Thr Ala Gly Gly Val Met Thr Ala Leu Ile Lys Arg
                405                 410                 415

Asn Ser Thr Ile Pro Thr Lys Gln Thr Gln Ile Phe Thr Thr Tyr Ser
                420                 425                 430

Asp Asn Gln Pro Gly Val Leu Ile Gln Val Tyr Glu Gly Glu Arg Ala
            435                 440                 445

Met Thr Lys Asp Asn Asn Leu Leu Gly Arg Phe Glu Leu Ser Gly Ile
            450                 455                 460

Pro Pro Ala Pro Arg Gly Val Pro Gln Ile Glu Val Thr Phe Asp Ile
465                 470                 475                 480

Asp Ala Asn Gly Ile Leu Asn Val Thr Ala Thr Asp Lys Ser Thr Gly
                485                 490                 495

Lys Ala Asn Lys Ile Thr Ile Thr Asn Asp Lys Gly Arg Leu Ser Lys
            500                 505                 510

Glu Glu Ile Glu Arg Met Val Gln Glu Ala Glu Lys Tyr Lys Ala Glu
            515                 520                 525

Asp Glu Val Gln Arg Glu Arg Val Ser Ala Lys Asn Ala Leu Glu Ser
        530                 535                 540

Tyr Ala Phe Asn Met Lys Ser Ala Val Glu Asp Glu Gly Leu Lys Gly
545                 550                 555                 560

Lys Ile Ser Glu Ala Asp Lys Lys Val Leu Asp Lys Cys Gln Glu
            565                 570                 575

Val Ile Ser Trp Leu Asp Ala Asn Thr Leu Ala Glu Lys Asp Glu Phe
            580                 585                 590

Glu His Lys Arg Lys Glu Leu Glu Gln Val Cys Asn Pro Ile Ile Ser
            595                 600                 605

Gly Leu Tyr Gln Gly Ala Gly Gly Pro Gly Pro Gly Gly Phe Gly Ala
    610                 615                 620

Gln Gly Pro Lys Gly Gly Ser Gly Ser Gly Pro Thr Ile Glu Glu Val
625                 630                 635                 640

Asp

<210> SEQ ID NO 6
<211> LENGTH: 641
<212> TYPE: PRT
<213> ORGANISM: Homo sapiens

<400> SEQUENCE: 6

Met Ala Thr Ala Lys Gly Ile Ala Ile Gly Ile Asp Leu Gly Thr Thr
1               5                   10                  15

Tyr Ser Cys Val Gly Val Phe Gln His Gly Lys Val Glu Ile Ile Ala
                20                  25                  30

Asn Asp Gln Gly Asn Arg Thr Thr Pro Ser Tyr Val Ala Phe Thr Asp
            35                  40                  45

Thr Glu Arg Leu Ile Gly Asp Ala Ala Lys Asn Gln Val Ala Met Asn
        50                  55                  60

Pro Gln Asn Thr Val Phe Asp Ala Lys Arg Leu Ile Gly Arg Lys Phe
65                  70                  75                  80
```

-continued

```
Asn Asp Pro Val Val Gln Ala Asp Met Lys Leu Trp Pro Phe Gln Val
             85                  90                  95
Ile Asn Glu Gly Gly Lys Pro Lys Val Leu Val Ser Tyr Lys Gly Glu
        100                 105                 110
Asn Lys Ala Phe Tyr Pro Glu Glu Ile Ser Ser Met Val Leu Thr Lys
            115                 120                 125
Leu Lys Glu Thr Ala Glu Ala Phe Leu Gly His Pro Val Thr Asn Ala
        130                 135                 140
Val Ile Thr Val Pro Ala Tyr Phe Asn Asp Ser Gln Arg Gln Ala Thr
145                 150                 155                 160
Lys Asp Ala Gly Val Ile Ala Gly Leu Asn Val Leu Arg Ile Ile Asn
                165                 170                 175
Glu Pro Thr Ala Ala Ala Ile Ala Tyr Gly Leu Asp Lys Gly Gly Gln
            180                 185                 190
Gly Glu Arg His Val Leu Ile Phe Asp Leu Gly Gly Gly Thr Phe Asp
        195                 200                 205
Val Ser Ile Leu Thr Ile Asp Asp Gly Ile Phe Glu Val Lys Ala Thr
    210                 215                 220
Ala Gly Asp Thr His Leu Gly Gly Glu Asp Phe Asp Asn Arg Leu Val
225                 230                 235                 240
Ser His Phe Val Glu Glu Phe Lys Arg Lys His Lys Lys Asp Ile Ser
                245                 250                 255
Gln Asn Lys Arg Ala Val Arg Arg Leu Arg Thr Ala Cys Glu Arg Ala
            260                 265                 270
Lys Arg Thr Leu Ser Ser Ser Thr Gln Ala Asn Leu Glu Ile Asp Ser
        275                 280                 285
Leu Tyr Glu Gly Ile Asp Phe Tyr Thr Ser Ile Thr Arg Ala Arg Phe
    290                 295                 300
Glu Glu Leu Cys Ala Asp Leu Phe Arg Gly Thr Leu Glu Pro Val Glu
305                 310                 315                 320
Lys Ala Leu Arg Asp Ala Lys Met Asp Lys Ala Lys Ile His Asp Ile
                325                 330                 335
Val Leu Val Gly Gly Ser Thr Arg Ile Pro Lys Val Gln Arg Leu Leu
            340                 345                 350
Gln Asp Tyr Phe Asn Gly Arg Asp Leu Asn Lys Ser Ile Asn Pro Asp
        355                 360                 365
Glu Ala Val Ala Tyr Gly Ala Ala Val Gln Ala Ala Ile Leu Met Gly
    370                 375                 380
Asp Lys Ser Glu Lys Val Gln Asp Leu Leu Leu Leu Asp Val Ala Pro
385                 390                 395                 400
Leu Ser Leu Gly Leu Glu Thr Ala Gly Gly Val Met Thr Ala Leu Ile
                405                 410                 415
Lys Arg Asn Ser Thr Ile Pro Thr Lys Gln Thr Gln Ile Phe Thr Thr
            420                 425                 430
Tyr Ser Asp Asn Gln Pro Gly Val Leu Ile Gln Val Tyr Glu Gly Glu
        435                 440                 445
Arg Ala Met Thr Lys Asp Asn Asn Leu Leu Gly Arg Phe Asp Leu Thr
    450                 455                 460
Gly Ile Pro Pro Ala Pro Arg Gly Val Pro Gln Ile Glu Val Thr Phe
465                 470                 475                 480
Asp Ile Asp Ala Asn Gly Ile Leu Asn Val Thr Ala Thr Asp Lys Ser
                485                 490                 495
```

-continued

```
Thr Gly Lys Val Asn Lys Ile Thr Ile Thr Asn Asp Lys Gly Arg Leu
            500                 505                 510

Ser Lys Glu Glu Ile Glu Arg Met Val Leu Asp Ala Glu Lys Tyr Lys
            515                 520                 525

Ala Glu Asp Glu Val Gln Arg Glu Lys Ile Ala Ala Lys Asn Ala Leu
530                 535                 540

Glu Ser Tyr Ala Phe Asn Met Lys Ser Val Val Ser Asp Glu Gly Leu
545                 550                 555                 560

Lys Gly Lys Ile Ser Glu Ser Asp Lys Asn Lys Ile Leu Asp Lys Cys
            565                 570                 575

Asn Glu Leu Leu Ser Trp Leu Glu Val Asn Gln Leu Ala Glu Lys Asp
            580                 585                 590

Glu Phe Asp His Lys Arg Lys Glu Leu Glu Gln Met Cys Asn Pro Ile
            595                 600                 605

Ile Thr Lys Leu Tyr Gln Gly Gly Cys Thr Gly Pro Ala Cys Gly Thr
            610                 615                 620

Gly Tyr Val Pro Gly Arg Pro Ala Thr Gly Pro Thr Ile Glu Glu Val
625                 630                 635                 640

Asp

<210> SEQ ID NO 7
<211> LENGTH: 639
<212> TYPE: PRT
<213> ORGANISM: Homo sapiens

<400> SEQUENCE: 7

Met Ser Ala Arg Gly Pro Ala Ile Gly Ile Asp Leu Gly Thr Thr Tyr
1               5                   10                  15

Ser Cys Val Gly Val Phe Gln His Gly Lys Val Glu Ile Ile Ala Asn
            20                  25                  30

Asp Gln Gly Asn Arg Thr Thr Pro Ser Tyr Val Ala Phe Thr Asp Thr
            35                  40                  45

Glu Arg Leu Ile Gly Asp Ala Ala Lys Asn Gln Val Ala Met Asn Pro
50                  55                  60

Thr Asn Thr Ile Phe Asp Ala Lys Arg Leu Ile Gly Arg Lys Phe Glu
65                  70                  75                  80

Asp Ala Thr Val Gln Ser Asp Met Lys His Trp Pro Phe Arg Val Val
            85                  90                  95

Ser Glu Gly Gly Lys Pro Lys Val Gln Val Glu Tyr Lys Gly Glu Thr
            100                 105                 110

Lys Thr Phe Phe Pro Glu Glu Ile Ser Ser Met Val Leu Thr Lys Met
            115                 120                 125

Lys Glu Ile Ala Glu Ala Tyr Leu Gly Gly Lys Val His Ser Ala Val
            130                 135                 140

Ile Thr Val Pro Ala Tyr Phe Asn Asp Ser Gln Arg Gln Ala Thr Lys
145                 150                 155                 160

Asp Ala Gly Thr Ile Thr Gly Leu Asn Val Leu Arg Ile Ile Asn Glu
            165                 170                 175

Pro Thr Ala Ala Ala Ile Ala Tyr Gly Leu Asp Lys Lys Gly Cys Ala
            180                 185                 190

Gly Gly Glu Lys Asn Val Leu Ile Phe Asp Leu Gly Gly Gly Thr Phe
            195                 200                 205

Asp Val Ser Ile Leu Thr Ile Glu Asp Gly Ile Phe Glu Val Lys Ser
            210                 215                 220
```

```
Thr Ala Gly Asp Thr His Leu Gly Gly Glu Asp Phe Asp Asn Arg Met
225                 230                 235                 240

Val Ser His Leu Ala Glu Glu Phe Lys Arg Lys His Lys Lys Asp Ile
                245                 250                 255

Gly Pro Asn Lys Arg Ala Val Arg Arg Leu Arg Thr Ala Cys Glu Arg
            260                 265                 270

Ala Lys Arg Thr Leu Ser Ser Ser Thr Gln Ala Ser Ile Glu Ile Asp
        275                 280                 285

Ser Leu Tyr Glu Gly Val Asp Phe Tyr Thr Ser Ile Thr Arg Ala Arg
    290                 295                 300

Phe Glu Glu Leu Asn Ala Asp Leu Phe Arg Gly Thr Leu Glu Pro Val
305                 310                 315                 320

Glu Lys Ala Leu Arg Asp Ala Lys Leu Asp Lys Gly Gln Ile Gln Glu
                325                 330                 335

Ile Val Leu Val Gly Gly Ser Thr Arg Ile Pro Lys Ile Gln Lys Leu
            340                 345                 350

Leu Gln Asp Phe Phe Asn Gly Lys Glu Leu Asn Lys Ser Ile Asn Pro
        355                 360                 365

Asp Glu Ala Val Ala Tyr Gly Ala Ala Val Gln Ala Ala Ile Leu Ile
    370                 375                 380

Gly Asp Lys Ser Glu Asn Val Gln Asp Leu Leu Leu Leu Asp Val Thr
385                 390                 395                 400

Pro Leu Ser Leu Gly Ile Glu Thr Ala Gly Gly Val Met Thr Pro Leu
                405                 410                 415

Ile Lys Arg Asn Thr Thr Ile Pro Thr Lys Gln Thr Gln Thr Phe Thr
            420                 425                 430

Thr Tyr Ser Asp Asn Gln Ser Ser Val Leu Val Gln Val Tyr Glu Gly
        435                 440                 445

Glu Arg Ala Met Thr Lys Asp Asn Asn Leu Leu Gly Lys Phe Asp Leu
    450                 455                 460

Thr Gly Ile Pro Pro Ala Pro Arg Gly Val Pro Gln Ile Glu Val Thr
465                 470                 475                 480

Phe Asp Ile Asp Ala Asn Gly Ile Leu Asn Val Thr Ala Ala Asp Lys
                485                 490                 495

Ser Thr Gly Lys Glu Asn Lys Ile Thr Ile Thr Asn Asp Lys Gly Arg
            500                 505                 510

Leu Ser Lys Asp Asp Ile Asp Arg Met Val Gln Glu Ala Glu Arg Tyr
        515                 520                 525

Lys Ser Glu Asp Glu Ala Asn Arg Asp Arg Val Ala Ala Lys Asn Ala
    530                 535                 540

Leu Glu Ser Tyr Thr Tyr Asn Ile Lys Gln Thr Val Glu Asp Glu Lys
545                 550                 555                 560

Leu Arg Gly Lys Ile Ser Glu Gln Asp Lys Asn Lys Ile Leu Asp Lys
                565                 570                 575

Cys Gln Glu Val Ile Asn Trp Leu Asp Arg Asn Gln Met Ala Glu Lys
            580                 585                 590

Asp Glu Tyr Glu His Lys Gln Lys Glu Leu Glu Arg Val Cys Asn Pro
        595                 600                 605

Ile Ile Ser Lys Leu Tyr Gln Gly Gly Pro Gly Gly Gly Ser Gly Gly
    610                 615                 620

Gly Gly Ser Gly Ala Ser Gly Gly Pro Thr Ile Glu Glu Val Asp
625                 630                 635
```

```
<210> SEQ ID NO 8
<211> LENGTH: 654
<212> TYPE: PRT
<213> ORGANISM: Homo sapiens

<400> SEQUENCE: 8

Met Lys Leu Ser Leu Val Ala Ala Met Leu Leu Leu Leu Ser Ala Ala
 1               5                  10                  15

Arg Ala Glu Glu Glu Asp Lys Lys Glu Asp Val Gly Thr Val Val Gly
            20                  25                  30

Ile Asp Leu Gly Thr Thr Tyr Ser Cys Val Gly Val Phe Lys Asn Gly
        35                  40                  45

Arg Val Glu Ile Ile Ala Asn Asp Gln Gly Asn Arg Ile Thr Pro Ser
    50                  55                  60

Tyr Val Ala Phe Thr Pro Glu Gly Glu Arg Leu Ile Gly Asp Ala Ala
65                  70                  75                  80

Lys Asn Gln Leu Thr Ser Asn Pro Glu Asn Thr Val Phe Asp Ala Lys
                85                  90                  95

Arg Leu Ile Gly Arg Thr Trp Asn Asp Pro Ser Val Gln Gln Asp Ile
            100                 105                 110

Lys Phe Leu Pro Phe Lys Val Val Glu Lys Lys Thr Lys Pro Tyr Ile
        115                 120                 125

Gln Val Asp Ile Gly Gly Gly Gln Thr Lys Thr Phe Ala Pro Glu Glu
    130                 135                 140

Ile Ser Ala Met Val Leu Thr Lys Met Lys Glu Thr Ala Glu Ala Tyr
145                 150                 155                 160

Leu Gly Lys Lys Val Thr His Ala Val Val Thr Val Pro Ala Tyr Phe
                165                 170                 175

Asn Asp Ala Gln Arg Gln Ala Thr Lys Asp Ala Gly Thr Ile Ala Gly
            180                 185                 190

Leu Asn Val Met Arg Ile Ile Asn Glu Pro Thr Ala Ala Ala Ile Ala
        195                 200                 205

Tyr Gly Leu Asp Lys Arg Glu Gly Glu Lys Asn Ile Leu Val Phe Asp
    210                 215                 220

Leu Gly Gly Gly Thr Phe Asp Val Ser Leu Leu Thr Ile Asp Asn Gly
225                 230                 235                 240

Val Phe Glu Val Val Ala Thr Asn Gly Asp Thr His Leu Gly Gly Glu
                245                 250                 255

Asp Phe Asp Gln Arg Val Met Glu His Phe Ile Lys Leu Tyr Lys Lys
            260                 265                 270

Lys Thr Gly Lys Asp Val Arg Lys Asp Asn Arg Ala Val Gln Lys Leu
        275                 280                 285

Arg Arg Glu Val Glu Lys Ala Lys Arg Ala Leu Ser Ser Gln His Gln
    290                 295                 300

Ala Arg Ile Glu Ile Glu Ser Phe Tyr Glu Gly Glu Asp Phe Ser Glu
305                 310                 315                 320

Thr Leu Thr Arg Ala Lys Phe Glu Glu Leu Asn Met Asp Leu Phe Arg
                325                 330                 335

Ser Thr Met Lys Pro Val Gln Lys Val Leu Glu Asp Ser Asp Leu Lys
            340                 345                 350

Lys Ser Asp Ile Asp Glu Ile Val Leu Val Gly Gly Ser Thr Arg Ile
        355                 360                 365

Pro Lys Ile Gln Gln Leu Val Lys Glu Phe Phe Asn Gly Lys Glu Pro
    370                 375                 380
```

Ser Arg Gly Ile Asn Pro Asp Glu Ala Val Ala Tyr Gly Ala Ala Val
385                 390                 395                 400

Gln Ala Gly Val Leu Ser Gly Asp Gln Asp Thr Gly Asp Leu Val Leu
            405                 410                 415

Leu Asp Val Cys Pro Leu Thr Leu Gly Ile Glu Thr Val Gly Gly Val
            420                 425                 430

Met Thr Lys Leu Ile Pro Arg Asn Thr Val Pro Thr Lys Lys Ser
            435                 440                 445

Gln Ile Phe Ser Thr Ala Ser Asp Asn Gln Pro Thr Val Thr Ile Lys
    450                 455                 460

Val Tyr Glu Gly Glu Arg Pro Leu Thr Lys Asp Asn His Leu Leu Gly
465                 470                 475                 480

Thr Phe Asp Leu Thr Gly Ile Pro Pro Ala Pro Arg Gly Val Pro Gln
                485                 490                 495

Ile Glu Val Thr Phe Glu Ile Asp Val Asn Gly Ile Leu Arg Val Thr
                500                 505                 510

Ala Glu Asp Lys Gly Thr Gly Asn Lys Asn Lys Ile Thr Ile Thr Asn
            515                 520                 525

Asp Gln Asn Arg Leu Thr Pro Glu Glu Ile Glu Arg Met Val Asn Asp
    530                 535                 540

Ala Glu Lys Phe Ala Glu Glu Asp Lys Lys Leu Lys Glu Arg Ile Asp
545                 550                 555                 560

Thr Arg Asn Glu Leu Glu Ser Tyr Ala Tyr Ser Leu Lys Asn Gln Ile
                565                 570                 575

Gly Asp Lys Glu Lys Leu Gly Gly Lys Leu Ser Ser Gly Asp Lys Glu
            580                 585                 590

Thr Met Glu Lys Ala Val Glu Glu Lys Ile Glu Trp Leu Glu Ser His
            595                 600                 605

Gln Asp Ala Asp Ile Glu Asp Phe Lys Ala Lys Lys Lys Glu Leu Glu
    610                 615                 620

Glu Ile Val Gln Pro Ile Ile Ser Lys Leu Tyr Gly Ser Ala Gly Pro
625                 630                 635                 640

Pro Pro Thr Gly Glu Glu Asp Thr Ala Glu Lys Asp Glu Leu
                645                 650

<210> SEQ ID NO 9
<211> LENGTH: 643
<212> TYPE: PRT
<213> ORGANISM: Homo sapiens

<400> SEQUENCE: 9

Met Gln Ala Pro Arg Glu Leu Ala Val Gly Ile Asp Leu Gly Thr Thr
1               5                   10                  15

Tyr Ser Cys Val Gly Val Phe Gln Gln Gly Arg Val Glu Ile Leu Ala
                20                  25                  30

Asn Asp Gln Gly Asn Arg Thr Thr Pro Ser Tyr Val Ala Phe Thr Asp
            35                  40                  45

Thr Glu Arg Leu Val Gly Asp Ala Ala Lys Ser Gln Ala Ala Leu Asn
    50                  55                  60

Pro His Asn Thr Val Phe Asp Ala Lys Arg Leu Ile Gly Arg Lys Phe
65                  70                  75                  80

Ala Asp Thr Thr Val Gln Ser Asp Met Lys His Trp Pro Phe Arg Val
                85                  90                  95

Val Ser Glu Gly Gly Lys Pro Lys Val Arg Val Cys Tyr Arg Gly Glu
            100                 105                 110

```
Asp Lys Thr Phe Tyr Pro Glu Glu Ile Ser Ser Met Val Leu Ser Lys
            115                 120                 125

Met Lys Glu Thr Ala Glu Ala Tyr Leu Gly Gln Pro Val Lys His Ala
        130                 135                 140

Val Ile Thr Val Pro Ala Tyr Phe Asn Asp Ser Gln Arg Gln Ala Thr
145                 150                 155                 160

Lys Asp Ala Gly Ala Ile Ala Gly Leu Asn Val Leu Arg Ile Ile Asn
                165                 170                 175

Glu Pro Thr Ala Ala Ala Ile Ala Tyr Gly Leu Asp Arg Arg Gly Ala
                180                 185                 190

Gly Glu Arg Asn Val Leu Ile Phe Asp Leu Gly Gly Gly Thr Phe Asp
            195                 200                 205

Val Ser Val Leu Ser Ile Asp Ala Gly Val Phe Glu Val Lys Ala Thr
        210                 215                 220

Ala Gly Asp Thr His Leu Gly Gly Glu Asp Phe Asp Asn Arg Leu Val
225                 230                 235                 240

Asn His Phe Met Glu Glu Phe Arg Arg Lys His Gly Lys Asp Leu Ser
                245                 250                 255

Gly Asn Lys Arg Ala Leu Arg Arg Leu Arg Thr Ala Cys Glu Arg Ala
                260                 265                 270

Lys Arg Thr Leu Ser Ser Ser Thr Gln Ala Thr Leu Glu Ile Asp Ser
            275                 280                 285

Leu Phe Glu Gly Val Asp Phe Tyr Thr Ser Ile Thr Arg Ala Arg Phe
        290                 295                 300

Glu Glu Leu Cys Ser Asp Leu Phe Arg Ser Thr Leu Glu Pro Val Glu
305                 310                 315                 320

Lys Ala Leu Arg Asp Ala Lys Leu Asp Lys Ala Gln Ile His Asp Val
                325                 330                 335

Val Leu Val Gly Gly Ser Thr Arg Ile Pro Lys Val Gln Lys Leu Leu
            340                 345                 350

Gln Asp Phe Phe Asn Gly Lys Glu Leu Asn Lys Ser Ile Asn Pro Asp
        355                 360                 365

Glu Ala Val Ala Tyr Gly Ala Ala Val Gln Ala Ala Val Leu Met Gly
370                 375                 380

Asp Lys Cys Glu Lys Val Gln Asp Leu Leu Leu Leu Asp Val Ala Pro
385                 390                 395                 400

Leu Ser Leu Gly Leu Glu Thr Ala Gly Gly Val Met Thr Thr Leu Ile
                405                 410                 415

Gln Arg Asn Ala Thr Ile Pro Thr Lys Gln Thr Gln Thr Phe Thr Thr
            420                 425                 430

Tyr Ser Asp Asn Gln Pro Gly Val Phe Ile Gln Val Tyr Glu Gly Glu
        435                 440                 445

Arg Ala Met Thr Lys Asp Asn Asn Leu Leu Gly Arg Phe Glu Leu Ser
450                 455                 460

Gly Ile Pro Pro Ala Pro Arg Gly Val Pro Gln Ile Glu Val Thr Phe
465                 470                 475                 480

Asp Ile Asp Ala Asn Gly Ile Leu Ser Val Thr Ala Thr Asp Arg Ser
                485                 490                 495

Thr Gly Lys Ala Asn Lys Ile Thr Ile Thr Asn Asp Lys Gly Arg Leu
            500                 505                 510

Ser Lys Glu Glu Val Glu Arg Met Val His Glu Ala Glu Gln Tyr Lys
        515                 520                 525
```

```
Ala Glu Asp Glu Ala Gln Arg Asp Arg Val Ala Ala Lys Asn Ser Leu
        530                 535                 540
Glu Ala His Val Phe His Val Lys Gly Ser Leu Gln Glu Glu Ser Leu
545                 550                 555                 560
Arg Asp Lys Ile Pro Glu Asp Arg Arg Lys Met Gln Asp Lys Cys
                565                 570                 575
Arg Glu Val Leu Ala Trp Leu Glu His Asn Gln Leu Ala Glu Lys Glu
                580                 585                 590
Glu Tyr Glu His Gln Lys Arg Glu Leu Glu Gln Ile Cys Arg Pro Ile
            595                 600                 605
Phe Ser Arg Leu Tyr Gly Gly Pro Gly Val Pro Gly Gly Ser Ser Cys
610                 615                 620
Gly Thr Gln Ala Arg Gln Gly Asp Pro Ser Thr Gly Pro Ile Ile Glu
625                 630                 635                 640
Glu Val Asp

<210> SEQ ID NO 10
<211> LENGTH: 646
<212> TYPE: PRT
<213> ORGANISM: Homo sapiens

<400> SEQUENCE: 10

Met Ser Lys Gly Pro Ala Val Gly Ile Asp Leu Gly Thr Thr Tyr Ser
1               5                   10                  15
Cys Val Gly Val Phe Gln His Gly Lys Val Glu Ile Ile Ala Asn Asp
                20                  25                  30
Gln Gly Asn Arg Thr Thr Pro Ser Tyr Val Ala Phe Thr Asp Thr Glu
            35                  40                  45
Arg Leu Ile Gly Asp Ala Ala Lys Asn Gln Val Ala Met Asn Pro Thr
        50                  55                  60
Asn Thr Val Phe Asp Ala Lys Arg Leu Ile Gly Arg Arg Phe Asp Asp
65                  70                  75                  80
Ala Val Val Gln Ser Asp Met Lys His Trp Pro Phe Met Val Val Asn
                85                  90                  95
Asp Ala Gly Arg Pro Lys Val Gln Val Glu Tyr Lys Gly Glu Thr Lys
                100                 105                 110
Ser Phe Tyr Pro Glu Glu Val Ser Ser Met Val Leu Thr Lys Met Lys
            115                 120                 125
Glu Ile Ala Glu Ala Tyr Leu Gly Lys Thr Val Thr Asn Ala Val Val
        130                 135                 140
Thr Val Pro Ala Tyr Phe Asn Asp Ser Gln Arg Gln Ala Thr Lys Asp
145                 150                 155                 160
Ala Gly Thr Ile Ala Gly Leu Asn Val Leu Arg Ile Ile Asn Glu Pro
                165                 170                 175
Thr Ala Ala Ala Ile Ala Tyr Gly Leu Asp Lys Lys Val Gly Ala Glu
                180                 185                 190
Arg Asn Val Leu Ile Phe Asp Leu Gly Gly Gly Thr Phe Asp Val Ser
            195                 200                 205
Ile Leu Thr Ile Glu Asp Gly Ile Phe Glu Val Lys Ser Thr Ala Gly
        210                 215                 220
Asp Thr His Leu Gly Gly Glu Asp Phe Asp Asn Arg Met Val Asn His
225                 230                 235                 240
```

```
Phe Ile Ala Glu Phe Lys Arg Lys His Lys Lys Asp Ile Ser Glu Asn
                245                 250                 255
Lys Arg Ala Val Arg Arg Leu Arg Thr Ala Cys Glu Arg Ala Lys Arg
            260                 265                 270
Thr Leu Ser Ser Ser Thr Gln Ala Ser Ile Glu Ile Asp Ser Leu Tyr
        275                 280                 285
Glu Gly Ile Asp Phe Tyr Thr Ser Ile Thr Arg Ala Arg Phe Glu Glu
    290                 295                 300
Leu Asn Ala Asp Leu Phe Arg Gly Thr Leu Asp Pro Val Glu Lys Ala
305                 310                 315                 320
Leu Arg Asp Ala Lys Leu Asp Lys Ser Gln Ile His Asp Ile Val Leu
            325                 330                 335
Val Gly Gly Ser Thr Arg Ile Pro Lys Ile Gln Lys Leu Leu Gln Asp
        340                 345                 350
Phe Phe Asn Gly Lys Glu Leu Asn Lys Ser Ile Asn Pro Asp Glu Ala
    355                 360                 365
Val Ala Tyr Gly Ala Ala Val Gln Ala Ala Ile Leu Ser Gly Asp Lys
370                 375                 380
Ser Glu Asn Val Gln Asp Leu Leu Leu Leu Asp Val Thr Pro Leu Ser
385                 390                 395                 400
Leu Gly Ile Glu Thr Ala Gly Gly Val Met Thr Val Leu Ile Lys Arg
            405                 410                 415
Asn Thr Thr Ile Pro Thr Lys Gln Thr Gln Thr Phe Thr Thr Tyr Ser
        420                 425                 430
Asp Asn Gln Pro Gly Val Leu Ile Gln Val Tyr Glu Gly Glu Arg Ala
    435                 440                 445
Met Thr Lys Asp Asn Asn Leu Leu Gly Lys Phe Glu Leu Thr Gly Ile
    450                 455                 460
Pro Pro Ala Pro Arg Gly Val Pro Gln Ile Glu Val Thr Phe Asp Ile
465                 470                 475                 480
Asp Ala Asn Gly Ile Leu Asn Val Ser Ala Val Asp Lys Ser Thr Gly
            485                 490                 495
Lys Glu Asn Lys Ile Thr Ile Thr Asn Asp Lys Gly Arg Leu Ser Lys
        500                 505                 510
Glu Asp Ile Glu Arg Met Val Gln Glu Ala Glu Lys Tyr Lys Ala Glu
    515                 520                 525
Asp Glu Lys Gln Arg Asp Lys Val Ser Ser Lys Asn Ser Leu Glu Ser
530                 535                 540
Tyr Ala Phe Asn Met Lys Ala Thr Val Glu Asp Glu Lys Leu Gln Gly
545                 550                 555                 560
Lys Ile Asn Asp Glu Asp Lys Gln Lys Ile Leu Asp Lys Cys Asn Glu
            565                 570                 575
Ile Ile Asn Trp Leu Asp Lys Asn Gln Thr Ala Glu Lys Glu Glu Phe
        580                 585                 590
Glu His Gln Gln Lys Glu Leu Glu Lys Val Cys Asn Pro Ile Ile Thr
    595                 600                 605
Lys Leu Tyr Gln Ser Ala Gly Gly Met Pro Gly Met Pro Gly Gly
    610                 615                 620
Phe Pro Gly Gly Gly Ala Pro Pro Ser Gly Gly Ala Ser Ser Gly Pro
625                 630                 635                 640
Thr Ile Glu Glu Val Asp
            645
```

```
<210> SEQ ID NO 11
<211> LENGTH: 679
<212> TYPE: PRT
<213> ORGANISM: Homo sapiens

<400> SEQUENCE: 11
```

| | | | | | | | | | | | | | | | |
|---|---|---|---|---|---|---|---|---|---|---|---|---|---|---|---|
| Met | Ile | Ser | Ala | Ser | Arg | Ala | Ala | Ala | Arg | Leu | Val | Gly | Ala | Ala | |
| 1 | | | | 5 | | | | | 10 | | | | | 15 | |
| Ala | Ser | Arg | Gly | Pro | Thr | Ala | Ala | Arg | His | Gln | Asp | Ser | Trp | Asn | Gly |
| | | | 20 | | | | | 25 | | | | | 30 | | |
| Leu | Ser | His | Glu | Ala | Phe | Arg | Leu | Val | Ser | Arg | Arg | Asp | Tyr | Ala | Ser |
| | | | 35 | | | | 40 | | | | | 45 | | | |
| Glu | Ala | Ile | Lys | Gly | Ala | Val | Val | Gly | Ile | Asp | Leu | Gly | Thr | Thr | Asn |
| | | | 50 | | | | | 55 | | | | | 60 | | |
| Ser | Cys | Val | Ala | Val | Met | Glu | Gly | Lys | Gln | Ala | Lys | Val | Leu | Glu | Asn |
| 65 | | | | | 70 | | | | | 75 | | | | | 80 |
| Ala | Glu | Gly | Ala | Arg | Thr | Thr | Pro | Ser | Val | Val | Ala | Phe | Thr | Ala | Asp |
| | | | | 85 | | | | | 90 | | | | | 95 | |
| Gly | Glu | Arg | Leu | Val | Gly | Met | Pro | Ala | Lys | Arg | Gln | Ala | Val | Thr | Asn |
| | | | 100 | | | | | 105 | | | | | 110 | | |
| Pro | Asn | Asn | Thr | Phe | Tyr | Ala | Thr | Lys | Arg | Leu | Ile | Gly | Arg | Arg | Tyr |
| | | | 115 | | | | | 120 | | | | | 125 | | |
| Asp | Asp | Pro | Glu | Val | Gln | Lys | Asp | Ile | Lys | Asn | Val | Pro | Phe | Lys | Ile |
| | 130 | | | | | 135 | | | | | 140 | | | | |
| Val | Arg | Ala | Ser | Asn | Gly | Asp | Ala | Trp | Val | Glu | Ala | His | Gly | Lys | Leu |
| 145 | | | | | 150 | | | | | 155 | | | | | 160 |
| Tyr | Ser | Pro | Ser | Gln | Ile | Gly | Ala | Phe | Val | Leu | Met | Lys | Met | Lys | Glu |
| | | | | 165 | | | | | 170 | | | | | 175 | |
| Thr | Ala | Glu | Asn | Tyr | Leu | Gly | His | Thr | Ala | Lys | Asn | Ala | Val | Ile | Thr |
| | | | 180 | | | | | 185 | | | | | 190 | | |
| Val | Pro | Ala | Tyr | Phe | Asn | Asp | Ser | Gln | Arg | Gln | Ala | Thr | Lys | Asp | Ala |
| | | | 195 | | | | | 200 | | | | | 205 | | |
| Gly | Gln | Ile | Ser | Gly | Leu | Asn | Val | Leu | Arg | Val | Ile | Asn | Glu | Pro | Thr |
| | 210 | | | | | 215 | | | | | 220 | | | | |
| Ala | Ala | Ala | Leu | Ala | Tyr | Gly | Leu | Asp | Lys | Ser | Glu | Asp | Lys | Val | Ile |
| 225 | | | | | 230 | | | | | 235 | | | | | 240 |
| Ala | Val | Tyr | Asp | Leu | Gly | Gly | Gly | Thr | Phe | Asp | Ile | Ser | Ile | Leu | Glu |
| | | | | 245 | | | | | 250 | | | | | 255 | |
| Ile | Gln | Lys | Gly | Val | Phe | Glu | Val | Lys | Ser | Thr | Asn | Gly | Asp | Thr | Phe |
| | | | 260 | | | | | 265 | | | | | 270 | | |
| Leu | Gly | Gly | Glu | Asp | Phe | Asp | Gln | Ala | Leu | Leu | Arg | His | Ile | Val | Lys |
| | | 275 | | | | | 280 | | | | | 285 | | | |
| Glu | Phe | Lys | Arg | Glu | Thr | Gly | Val | Asp | Leu | Thr | Lys | Asp | Asn | Met | Ala |
| | 290 | | | | | 295 | | | | | 300 | | | | |
| Leu | Gln | Arg | Val | Arg | Glu | Ala | Glu | Lys | Ala | Lys | Cys | Glu | Leu | Ser |
| 305 | | | | | 310 | | | | | 315 | | | | | 320 |
| Ser | Ser | Val | Gln | Thr | Asp | Ile | Asn | Leu | Pro | Tyr | Leu | Thr | Met | Asp | Ser |
| | | | | 325 | | | | | 330 | | | | | 335 | |
| Ser | Gly | Pro | Lys | His | Leu | Asn | Met | Lys | Leu | Thr | Arg | Ala | Gln | Phe | Glu |
| | | | 340 | | | | | 345 | | | | | 350 | | |
| Gly | Ile | Val | Thr | Asp | Leu | Ile | Arg | Arg | Thr | Ile | Ala | Pro | Cys | Gln | Lys |
| | | 355 | | | | | 360 | | | | | 365 | | | |
| Ala | Met | Gln | Asp | Ala | Glu | Val | Ser | Lys | Ser | Asp | Ile | Gly | Glu | Val | Ile |
| | 370 | | | | | 375 | | | | | 380 | | | | |

```
Leu Val Gly Gly Met Thr Arg Met Pro Lys Val Gln Gln Thr Val Gln
385                 390                 395                 400

Asp Leu Phe Gly Arg Ala Pro Ser Lys Ala Val Asn Pro Asp Glu Ala
            405                 410                 415

Val Ala Ile Gly Ala Ala Ile Gln Gly Gly Val Leu Ala Gly Asp Val
        420                 425                 430

Thr Asp Val Leu Leu Asp Val Thr Pro Leu Ser Leu Gly Ile Glu
    435                 440                 445

Thr Leu Gly Gly Val Phe Thr Lys Leu Ile Asn Arg Asn Thr Thr Ile
    450                 455                 460

Pro Thr Lys Lys Ser Gln Val Phe Ser Thr Ala Ala Asp Gly Gln Thr
465                 470                 475                 480

Gln Val Glu Ile Lys Val Cys Gln Gly Glu Arg Glu Met Ala Gly Asp
            485                 490                 495

Asn Lys Leu Leu Gly Gln Phe Thr Leu Ile Gly Ile Pro Pro Ala Pro
        500                 505                 510

Arg Gly Val Pro Gln Ile Glu Val Thr Phe Asp Ile Asp Ala Asn Gly
        515                 520                 525

Ile Val His Val Ser Ala Lys Asp Lys Gly Thr Gly Arg Glu Gln Gln
    530                 535                 540

Ile Val Ile Gln Ser Ser Gly Gly Leu Ser Lys Asp Asp Ile Glu Asn
545                 550                 555                 560

Met Val Lys Asn Ala Glu Lys Tyr Ala Glu Asp Arg Arg Lys Lys
            565                 570                 575

Glu Arg Val Glu Ala Val Asn Met Ala Glu Gly Ile Ile His Asp Thr
        580                 585                 590

Glu Thr Lys Met Glu Glu Phe Lys Asp Gln Leu Pro Ala Asp Glu Cys
        595                 600                 605

Asn Lys Leu Lys Glu Glu Ile Ser Lys Met Arg Glu Leu Leu Ala Arg
        610                 615                 620

Lys Asp Ser Glu Thr Gly Glu Asn Ile Arg Gln Ala Ala Ser Ser Leu
625                 630                 635                 640

Gln Gln Ala Ser Leu Lys Leu Phe Glu Met Ala Tyr Lys Lys Met Ala
                645                 650                 655

Ser Glu Arg Glu Gly Ser Gly Ser Ser Gly Thr Gly Glu Gln Lys Glu
            660                 665                 670

Asp Gln Lys Glu Glu Lys Gln
        675

<210> SEQ ID NO 12
<211> LENGTH: 732
<212> TYPE: PRT
<213> ORGANISM: Homo sapiens

<400> SEQUENCE: 12

Met Pro Glu Glu Thr Gln Thr Gln Asp Gln Pro Met Glu Glu Glu Glu
1               5                   10                  15

Val Glu Thr Phe Ala Phe Gln Ala Glu Ile Ala Gln Leu Met Ser Leu
            20                  25                  30

Ile Ile Asn Thr Phe Tyr Ser Asn Lys Glu Ile Phe Leu Arg Glu Leu
        35                  40                  45

Ile Ser Asn Ser Ser Asp Ala Leu Asp Lys Ile Arg Tyr Glu Ser Leu
    50                  55                  60

Thr Asp Pro Ser Lys Leu Asp Ser Gly Lys Glu Leu His Ile Asn Leu
65                  70                  75                  80
```

```
Ile Pro Asn Lys Gln Asp Arg Thr Leu Thr Ile Val Asp Thr Gly Ile
                85                  90                  95

Gly Met Thr Lys Ala Asp Leu Ile Asn Asn Leu Gly Thr Ile Ala Lys
            100                 105                 110

Ser Gly Thr Lys Ala Phe Met Glu Ala Leu Gln Ala Gly Ala Asp Ile
        115                 120                 125

Ser Met Ile Gly Gln Phe Gly Val Gly Phe Tyr Ser Ala Tyr Leu Val
130                 135                 140

Ala Glu Lys Val Thr Val Ile Thr Lys His Asn Asp Asp Glu Gln Tyr
145                 150                 155                 160

Ala Trp Glu Ser Ser Ala Gly Gly Ser Phe Thr Val Arg Thr Asp Thr
                165                 170                 175

Gly Glu Pro Met Gly Arg Gly Thr Lys Val Ile Leu His Leu Lys Glu
            180                 185                 190

Asp Gln Thr Glu Tyr Leu Glu Glu Arg Arg Ile Lys Glu Ile Val Lys
        195                 200                 205

Lys His Ser Gln Phe Ile Gly Tyr Pro Ile Thr Leu Phe Val Glu Lys
210                 215                 220

Glu Arg Asp Lys Glu Val Ser Asp Asp Glu Ala Glu Glu Lys Glu Asp
225                 230                 235                 240

Lys Glu Glu Glu Lys Glu Lys Glu Glu Lys Glu Ser Glu Asp Lys Pro
                245                 250                 255

Glu Ile Glu Asp Val Gly Ser Asp Glu Glu Glu Lys Lys Asp Gly
            260                 265                 270

Asp Lys Lys Lys Lys Lys Ile Lys Glu Lys Tyr Ile Asp Gln Glu
        275                 280                 285

Glu Leu Asn Lys Thr Lys Pro Ile Trp Thr Arg Asn Pro Asp Asp Ile
290                 295                 300

Thr Asn Glu Glu Tyr Gly Glu Phe Tyr Lys Ser Leu Thr Asn Asp Trp
305                 310                 315                 320

Glu Asp His Leu Ala Val Lys His Phe Ser Val Glu Gly Gln Leu Glu
                325                 330                 335

Phe Arg Ala Leu Leu Phe Val Pro Arg Arg Ala Pro Phe Asp Leu Phe
            340                 345                 350

Glu Asn Arg Lys Lys Lys Asn Asn Ile Lys Leu Tyr Val Arg Arg Val
        355                 360                 365

Phe Ile Met Asp Asn Cys Glu Glu Leu Ile Pro Glu Tyr Leu Asn Phe
370                 375                 380

Ile Arg Gly Val Val Asp Ser Glu Asp Leu Pro Leu Asn Ile Ser Arg
385                 390                 395                 400

Glu Met Leu Gln Gln Ser Lys Ile Leu Lys Val Ile Arg Lys Asn Leu
                405                 410                 415

Val Lys Lys Cys Leu Glu Leu Phe Thr Glu Leu Ala Glu Asp Lys Glu
            420                 425                 430

Asn Tyr Lys Lys Phe Tyr Glu Gln Phe Ser Lys Asn Ile Lys Leu Gly
        435                 440                 445

Ile His Glu Asp Ser Gln Asn Arg Lys Lys Leu Ser Glu Leu Leu Arg
450                 455                 460

Tyr Tyr Thr Ser Ala Ser Gly Asp Glu Met Val Ser Leu Lys Asp Tyr
465                 470                 475                 480

Cys Thr Arg Met Lys Glu Asn Gln Lys His Ile Tyr Tyr Ile Thr Gly
                485                 490                 495
```

| | | | | | | | | | | | | |
|---|---|---|---|---|---|---|---|---|---|---|---|---|
|Glu|Thr|Lys|Asp|Gln|Val|Ala|Asn|Ser|Ala|Phe|Val|Glu Arg Leu Arg|
| | | |500| | | |505| | | |510| |

Lys His Gly Leu Glu Val Ile Tyr Met Ile Glu Pro Ile Asp Glu Tyr
        515                 520                 525

Cys Val Gln Gln Leu Lys Glu Phe Glu Gly Lys Thr Leu Val Ser Val
        530                 535                 540

Thr Lys Glu Gly Leu Glu Leu Pro Glu Asp Glu Glu Lys Lys Lys
545                 550                 555                 560

Gln Glu Glu Lys Lys Thr Lys Phe Glu Asn Leu Cys Lys Ile Met Lys
            565                 570                 575

Asp Ile Leu Glu Lys Lys Val Glu Lys Val Val Ser Asn Arg Leu
            580                 585                 590

Val Thr Ser Pro Cys Cys Ile Val Thr Ser Thr Tyr Gly Trp Thr Ala
        595                 600                 605

Asn Met Glu Arg Ile Met Lys Ala Gln Ala Leu Arg Asp Asn Ser Thr
610                 615                 620

Met Gly Tyr Met Ala Ala Lys Lys His Leu Glu Ile Asn Pro Asp His
625                 630                 635                 640

Ser Ile Ile Glu Thr Leu Arg Gln Lys Ala Glu Ala Asp Lys Asn Asp
            645                 650                 655

Lys Ser Val Lys Asp Leu Val Ile Leu Leu Tyr Glu Thr Ala Leu Leu
        660                 665                 670

Ser Ser Gly Phe Ser Leu Glu Asp Pro Gln Thr His Ala Asn Arg Ile
        675                 680                 685

Tyr Arg Met Ile Lys Leu Gly Leu Gly Ile Asp Glu Asp Asp Pro Thr
        690                 695                 700

Ala Asp Asp Thr Ser Ala Ala Val Thr Glu Glu Met Pro Pro Leu Glu
705                 710                 715                 720

Gly Asp Asp Asp Thr Ser Arg Met Glu Glu Val Asp
                725                 730

```
<210> SEQ ID NO 13
<211> LENGTH: 2445
<212> TYPE: DNA
<213> ORGANISM: Homo sapiens

<400> SEQUENCE: 13
ataaaagccc agggggcaagc ggtccggata acggctagcc tgaggagctg ctgcgacagt      60
ccactacctt tttcgagagt gactcccgtt gtcccaaggc ttcccagagc gaacctgtgc     120
ggctgcaggc accggcgcgt cgagtttccg gcgtccggaa ggaccgagct cttctcgcgg     180
atccagtgtt ccgtttccag cccccaatct cagagcggag ccgacagaga gcagggaacc     240
ggcatggcca agccgcggc gatcggcatc gacctgggca ccaccactac ctgcgtgggg     300
gtgttccaac acggcaaggt ggagatcatc gccaacgacc agggcaaccg caccaccccc     360
agctacgtgg ccttcacgga caccgagcgg ctcatcgggg atgcggccaa gaaccaggtg     420
gcgctgaacc cgcagaacac cgtgtttgac gcgaagcggc tgattggccg caagttcggc     480
gacccggtgg tgcagtcgga catgaagcac tggcctttcc aggtgatcaa cgacggagac     540
aagcccaagg tgcaggtgag ctacaagggg gagaccaagg cattctaccc cgaggagatc     600
tcgtccatgg tgctgaccaa gatgaaggag atcgccgagg cgtacctggg ctacccggtg     660
accaacgcgt gatcaccgt gccggcctac ttcaacgact cgcagcgcca ggccaccaag     720
gatgcgggtg tgatcgcggg gctcaacgtg ctgcggatca tcaacgagcc cacggccgcc     780
```

| | |
|---|---|
| gccatcgcct acggcctgga cagaacgggc aaggggagc gcaacgtgct catctttgac | 840 |
| ctgggcgggg gcaccttcga cgtgtccatc ctgacgatcg acgacggcat cttcgaggtg | 900 |
| aaggccacgg ccggggacac ccacctgggt ggggaggact ttgacaacag gctggtgaac | 960 |
| cacttcgtgg aggagttcaa gagaaaacac aagaaggaca tcagccagaa caagcgagcc | 1020 |
| gtgaggcggc tgcgcaccgc ctgcgagagg gccaagagga ccctgtcgtc cagcacccag | 1080 |
| gccagcctgg agatcgactc cctgtttgag ggcatcgact tctacacgtc catcaccagg | 1140 |
| gcgaggttcg aggagctgtg ctccgacctg ttccgaagca ccctggagcc cgtggagaag | 1200 |
| gctctgcgcg acgccaagct ggacaaggcc cagattcacg acctggtcct ggtcggggc | 1260 |
| tccacccgca tccccaaggt gcagaagctg ctgcaggact tcttcaacgg gcgcgacctg | 1320 |
| aacaagagca tcaaccccga cgaggctgtg gcctacgggg cggcggtgca ggcggccatc | 1380 |
| ctgatggggg acaagtccga gaacgtgcag gacctgctgc tgctggacgt ggctcccctg | 1440 |
| tcgctggggc tggagacggc cggaggcgtg atgactgccc tgatcaagcg caactccacc | 1500 |
| atccccacca gcagacgca gatcttcacc acctactccg acaaccaacc cggggtgctg | 1560 |
| atccaggtgt acgagggcga gagggccatg acgaaagaca acaatctgtt ggggcgcttc | 1620 |
| gagctgagcg gcatccctcc ggcccccagg ggcgtgcccc agatcgaggt gaccttcgac | 1680 |
| atcgatgcca acggcatcct gaacgtcacg gccacggaca agagcaccgg caaggccaac | 1740 |
| aagatcacca tcaccaacga caaggccgc ctgagcaagg aggagatcga gcgcatggtg | 1800 |
| caggaggcgg agaagtacaa agcggaggac gaggtgcagc gcgagagggt gtcagccaag | 1860 |
| aacgccctgg agtcctacgc cttcaacatg aagagcgccg tggaggatga ggggctcaag | 1920 |
| ggcaagatca gcgaggcgga caagaagaag gtgctggaca agtgtcaaga ggtcatctcg | 1980 |
| tggctggacg ccaacaccct tggccgagaag gacgagtttg agcacaagag gaaggagctg | 2040 |
| gagcaggtgt gtaaccccat catcagcgga ctgtaccagg gtgccggtgg tcccgggcct | 2100 |
| gggggcttcg gggctcaggg tcccaaggga gggtctgggt caggccccac cattgaggag | 2160 |
| gtagattagg ggcctttcca agattgctgt ttttgttttg gagcttcaag actttgcatt | 2220 |
| tcctagtatt tctgtttgtc agttctcaat ttcctgtgtt tgcaatgttg aaattttttg | 2280 |
| gtgaagtact gaacttgctt tttttccggt ttctacatgc agagatgaat ttatactgcc | 2340 |
| atcttcacgac tatttcttct ttttaataca cttaactcag gccattttt aagttggtta | 2400 |
| cttcaaagta aataaacttt aaaattcaaa aaaaaaaaa aaaaa | 2445 |

<210> SEQ ID NO 14
<211> LENGTH: 3366
<212> TYPE: DNA
<213> ORGANISM: Homo sapiens

<400> SEQUENCE: 14

| | |
|---|---|
| gcatgcgtag gcgcgcggcc gcggcggcgg ctggggaggg ttcttccgga aggttcggga | 60 |
| ggcttctgga aaagcgccg cgcgctgggc gggcccgtcg ctatataagg caggcgcggg | 120 |
| ggtggcgcgt cagttgcttc agcgtcccgg tgtggctgtg ccgttggtcc tgtgcggtca | 180 |
| cttagccaag atgcctgagg aaacccagac ccaagaccaa ccgatggagg aggaggaggt | 240 |
| tgagacgttc gcctttcagg cagaaattgc ccagttgatg tcattgatca tcaatacttt | 300 |
| ctactcgaac aaagagatct ttctgagaga gctcatttca aattcatcag atgcattgga | 360 |
| caaaatccgg tatgaaagct tgacagatcc cagtaaatta gactctggga aagagctgca | 420 |
| tattaacctt ataccgaaca aacaagatcg aactctcact attgtggata ctggaattgg | 480 |

```
aatgaccaag gctgacttga tcaataacct tggtactatc gccaagtctg ggaccaaagc      540
gttcatggaa gctttgcagg ctggtgcaga tatctctatg attggccagt tcggtgttgg      600
tttttattct gcttatttgg ttgctgagaa agtaactgtg atcaccaaac ataacgatga      660
tgagcagtac gcttgggagt cctcagcagg gggatcattc acagtgagga cagacacagg      720
tgaacctatg ggtcgtggaa caaaagttat cctacacctg aaagaagacc aaactgagta      780
cttggaggaa cgaagaataa aggagattgt gaagaaacat tctcagttta ttggatatcc      840
cattactctt tttgtggaga aggaacgtga taaagaagta agcgatgatg aggctgaaga      900
aaaggaagac aaagaagaag aaaaagaaaa agagagaaaa gagtcggaag acaaacctga      960
aattgaagat gttggttctg atgaggaaga agaaaagaag gatggtgaca agaagaagaa     1020
gaagaagatt aaggaaaagt acatcgatca agaaagagctc aacaaaacaa agcccatctg     1080
gaccagaaat cccgacgata ttactaatga ggagtacgga gaattctata agagcttgac     1140
caatgactgg gaagatcact tggcagtgaa gcatttttca gttgaaggac agttggaatt     1200
cagagccctt ctatttgtcc cacgacgtgc tccttttgat ctgtttgaaa acagaaagaa     1260
aaagaacaac atcaaattgt atgtacgcag agttttcatc atggataact gtgaggagct     1320
aatccctgaa tatctgaact tcattagagg ggtggtagac tcggaggatc tccctctaaa     1380
catatcccgt gagatgttgc aacaaagcaa aattttgaaa gttatcagga gaatttggt      1440 caaaaaatgc ttagaactct ttactgaact ggcggaagat aaagagaact acagaaatt      1500 ctatgagcag ttctctaaaa acataaagct tggaatacac gaagactctc aaaatcggaa     1560
gaagctttca gagctgttaa ggtactacac atctgcctct ggtgatgaga tggtttctct     1620
caaggactac tgcaccagaa tgaaggagaa ccagaaacat atctattata tcacaggtga     1680
gaccaaggac caggtagcta actcagcctt tgtggaacgt cttcggaaac atggcttaga     1740
agtgatctat atgattgagc ccattgatga gtactgtgtc caacagctga aggaatttga     1800
ggggaagact ttagtgtcag tcaccaaaga aggcctggaa cttccagagg atgaagaaga     1860 gaaaagaag caggaagaga aaaaaacaaa gtttgagaac ctctgcaaaa tcatgaaaga     1920
catattggag aaaaaagttg aaaaggtggt tgtgtcaaac cgattggtga catctccatg     1980
ctgtattgtc acaagcacat atggctggac agcaaacatg gagagaatca tgaaagctca     2040
agccctaaga gacaactcaa caatgggtta catggcagca aagaaacacc tggagataaa     2100
ccctgaccat tccattattg agaccttaag gcaaaaggca gaggctgata agaacgacaa     2160
gtctgtgaag gatctggtca tcttgcttta tgaaactgcg ctcctgtctt ctggcttcag     2220
tctggaagat ccccagacac atgctaacag gatctacagg atgatcaaac ttggtctggg     2280
tattgatgaa gatgacccta ctgctgatga taccagtgct gctgtaactg aagaaatgcc     2340
accccttgaa ggagatgacg acacatcacg catggaagaa gtagactaat ctctggctga     2400
gggatgactt acctgttcag tactctacaa ttcctctgat aatatatttt caaggatgtt     2460
tttctttatt tttgttaata ttaaaagtc tgtatggcat gacaactact ttaagggaa     2520 gataagattt ctgtctacta agtgatgctg tgataccttaa ggcactaaag cagagctagt     2580
aatgcttttt gagtttcatg ttggtttatt ttcacagatt ggggtaacgt gcactgtaag     2640
acgtatgtaa catgatgtta actttgtggt ctaaagtgtt tagctgtcaa gccggatgcc     2700
taagtagacc aaatcttgtt attgaagtgt tctgagctgt atcttgatgt ttagaaaagt     2760
attcgttaca tcttgtagga tctactttt gaactttca ttccctgtag ttgacaattc      2820
tgcatgtact agtcctctag aaataggtta aactgaagca acttgatgga aggatctctc     2880
```

```
cacagggctt gttttccaaa gaaaagtatt gtttggagga gcaaagttaa aagcctacct    2940
aagcatatcg taaagctgtt caaaaataac tcagacccag tcttgtggat ggaaatgtag    3000
tgctcgagtc acattctgct taaagttgta acaaatacag atgagttaaa agatattgtg    3060
tgacagtgtc ttatttaggg ggaaagggga gtatctggat gacagttagt gccaaaatgt    3120
aaaacatgag gcgctagcag gagatggtta acactagct gctccaaggg ttgacatggt      3180
cttcccagca tgtactcagc aggtgtgggg tggagcacac gtaggcacag aaaacaggaa    3240
tgcagacaac atgcatcccc tgcgtccatg agttacatgt gttctcttag tgtccacgtt    3300
gttttgatgt tattcatgga ataccttctg tgttaaatac agtcacttaa ttccttggcc    3360
ttaaaa                                                              3366
```

<210> SEQ ID NO 15
<211> LENGTH: 20
<212> TYPE: PRT
<213> ORGANISM: Homo sapiens

<400> SEQUENCE: 15

Met Leu Arg Leu Pro Thr Val Phe Arg Gln Met Arg Pro Val Ser Arg
1               5                   10                  15

Val Leu Ala Pro
            20

<210> SEQ ID NO 16
<211> LENGTH: 20
<212> TYPE: PRT
<213> ORGANISM: Homo sapiens

<400> SEQUENCE: 16

Arg Val Leu Ala Pro His Leu Thr Arg Ala Tyr Ala Lys Asp Val Lys
1               5                   10                  15

Phe Gly Ala Asp
            20

<210> SEQ ID NO 17
<211> LENGTH: 19
<212> TYPE: PRT
<213> ORGANISM: Homo sapiens

<400> SEQUENCE: 17

Leu Leu Ala Asp Ala Val Ala Val Thr Met Gly Lys Gly Arg Thr Val
1               5                   10                  15

Ile Ile Glu

<210> SEQ ID NO 18
<211> LENGTH: 20
<212> TYPE: PRT
<213> ORGANISM: Homo sapiens

<400> SEQUENCE: 18

Thr Val Ile Ile Glu Gln Ser Trp Gly Ser Pro Lys Val Thr Lys Asp
1               5                   10                  15

Gly Val Thr Val
            20

<210> SEQ ID NO 19
<211> LENGTH: 20
<212> TYPE: PRT
<213> ORGANISM: Homo sapiens

```
<400> SEQUENCE: 19

Asp Gly Val Thr Val Ala Lys Ser Ile Asp Leu Lys Asp Lys Tyr Lys
1               5                   10                  15

Asn Ile Gly Ala
            20

<210> SEQ ID NO 20
<211> LENGTH: 20
<212> TYPE: PRT
<213> ORGANISM: Homo sapiens

<400> SEQUENCE: 20

Lys Asn Ile Gly Ala Lys Leu Val Gln Asp Val Ala Asn Asn Thr Asn
1               5                   10                  15

Glu Glu Ala Gly
            20

<210> SEQ ID NO 21
<211> LENGTH: 20
<212> TYPE: PRT
<213> ORGANISM: Homo sapiens

<400> SEQUENCE: 21

Asn Glu Glu Ala Gly Lys Gly Thr Thr Thr Ala Thr Val Leu Ala Arg
1               5                   10                  15

Ser Ile Ala Lys
            20

<210> SEQ ID NO 22
<211> LENGTH: 20
<212> TYPE: PRT
<213> ORGANISM: Homo sapiens

<400> SEQUENCE: 22

Arg Ser Ile Ala Lys Glu Gly Phe Glu Lys Ile Ser Lys Gly Ala Asn
1               5                   10                  15

Pro Val Glu Ile
            20

<210> SEQ ID NO 23
<211> LENGTH: 20
<212> TYPE: PRT
<213> ORGANISM: Homo sapiens

<400> SEQUENCE: 23

Asn Pro Val Glu Ile Arg Arg Gly Val Met Leu Ala Val Asp Ala Val
1               5                   10                  15

Ile Ala Glu Leu
            20

<210> SEQ ID NO 24
<211> LENGTH: 20
<212> TYPE: PRT
<213> ORGANISM: Homo sapiens

<400> SEQUENCE: 24

Val Ile Ala Glu Leu Lys Lys Gln Ser Lys Pro Val Thr Thr Pro Glu
1               5                   10                  15

Glu Ile Ala Gln
            20
```

```
<210> SEQ ID NO 25
<211> LENGTH: 20
<212> TYPE: PRT
<213> ORGANISM: Homo sapiens

<400> SEQUENCE: 25

Glu Glu Ile Ala Gln Val Ala Thr Ile Ser Ala Asn Gly Asp Lys Glu
1               5                   10                  15

Ile Gly Asn Ile
            20

<210> SEQ ID NO 26
<211> LENGTH: 19
<212> TYPE: PRT
<213> ORGANISM: Homo sapiens

<400> SEQUENCE: 26

Glu Ile Gly Asn Ile Ile Ser Asp Ala Met Lys Lys Val Gly Arg Lys
1               5                   10                  15

Gly Val Ile

<210> SEQ ID NO 27
<211> LENGTH: 20
<212> TYPE: PRT
<213> ORGANISM: Homo sapiens

<400> SEQUENCE: 27

Arg Lys Gly Val Ile Thr Val Lys Asp Gly Lys Thr Leu Asn Asp Glu
1               5                   10                  15

Leu Glu Ile Ile
            20

<210> SEQ ID NO 28
<211> LENGTH: 20
<212> TYPE: PRT
<213> ORGANISM: Homo sapiens

<400> SEQUENCE: 28

Glu Leu Glu Ile Ile Glu Gly Met Lys Phe Asp Arg Gly Tyr Ile Ser
1               5                   10                  15

Pro Tyr Phe Ile
            20

<210> SEQ ID NO 29
<211> LENGTH: 20
<212> TYPE: PRT
<213> ORGANISM: Homo sapiens

<400> SEQUENCE: 29

Ser Pro Tyr Phe Ile Asn Thr Ser Lys Gly Gln Lys Cys Glu Phe Gln
1               5                   10                  15

Asp Ala Tyr Val
            20

<210> SEQ ID NO 30
<211> LENGTH: 20
<212> TYPE: PRT
<213> ORGANISM: Homo sapiens
```

```
<400> SEQUENCE: 30

Gln Asp Ala Tyr Val Leu Leu Ser Glu Lys Lys Ile Ser Ser Ile Gln
1               5                   10                  15

Ser Ile Val Pro
            20

<210> SEQ ID NO 31
<211> LENGTH: 21
<212> TYPE: PRT
<213> ORGANISM: Homo sapiens

<400> SEQUENCE: 31

Gln Ser Ile Val Pro Ala Leu Glu Ile Ala Asn Ala His Arg Lys Pro
1               5                   10                  15

Leu Val Ile Ile Ala
            20

<210> SEQ ID NO 32
<211> LENGTH: 20
<212> TYPE: PRT
<213> ORGANISM: Mycobacterium tuberculosis

<400> SEQUENCE: 32

Ala Tyr Asp Glu Glu Ala Arg Arg Gly Leu Glu Arg Gly Leu Asn Ala
1               5                   10                  15

Leu Ala Asp Ala
            20

<210> SEQ ID NO 33
<211> LENGTH: 15
<212> TYPE: PRT
<213> ORGANISM: Mycobacterium tuberculosis

<400> SEQUENCE: 33

Glu Glu Ser Asn Thr Phe Gly Leu Gln Leu Glu Leu Thr Glu Gly
1               5                   10                  15

<210> SEQ ID NO 34
<211> LENGTH: 20
<212> TYPE: PRT
<213> ORGANISM: Mycobacterium tuberculosis

<400> SEQUENCE: 34

Ala Tyr Asp Glu Glu Ala Arg Arg Gly Leu Glu Arg Gly Leu Asn Ala
1               5                   10                  15

Leu Ala Asp Ala
            20

<210> SEQ ID NO 35
<211> LENGTH: 20
<212> TYPE: PRT
<213> ORGANISM: Rattus norvergicus

<400> SEQUENCE: 35

Lys Phe Gly Ala Asp Ala Arg Ala Leu Met Leu Gln Gly Val Asp Leu
1               5                   10                  15

Leu Ala Asp Ala
            20
```

DNA VACCINES ENCODING HEAT SHOCK PROTEINS

FIELD OF THE INVENTION

The present invention relates to recombinant constructs encoding heat shock proteins or active fragments thereof, effective in treating T cell mediated diseases including inflammatory autoimmune diseases by DNA vaccination. The present invention further relates to compositions and methods for treating T cell mediated diseases.

BACKGROUND OF THE INVENTION

While the normal immune system is closely regulated, aberrations in immune responses are not uncommon. In some instances, the immune system functions inappropriately and reacts to a component of the host as if it were, in fact, foreign. Such a response results in an autoimmune disease, in which the host's immune system attacks the host's own tissue. T cells, as the primary regulators of the immune system, directly or indirectly effect such autoimmune pathologies. T cell-mediated autoimmune diseases refer to any condition in which an inappropriate T cell response is a component of the disease. This includes both diseases directly mediated by T cells, and also diseases in which an inappropriate T cell response contributes to the production of abnormal antibodies.

Numerous diseases are believed to result from autoimmune mechanisms. Prominent among these are rheumatoid arthritis, systemic lupus erythematosus, multiple sclerosis, Type I diabetes, myasthenia gravis and pemphigus vulgaris. Autoimmune diseases affect millions of individuals worldwide and the cost of these diseases, in terms of actual treatment expenditures and lost productivity, is measured in billions of dollars annually.

Adjuvant arthritis (AA) is an experimental autoimmune disease that models several features of human rheumatoid arthritis (1). AA is induced in Lewis rats by immunization with heat killed *Mycobacterium tuberculosis* (Mt) suspended in Incomplete Freund's Adjuvant (IFA) (1). T-cell reactivity against the mycobacterial 65 kDa heat shock protein (HSP65) is involved in the progression of AA. HSP65-specific T-cells directed against an epitope formed by aa 180-188 (2) cross-react with a self-antigen present in cartilage (3) and can adoptively transfer AA (4, 5). However, vaccination with HSP65 or HSP65-peptides can also prevent the development of AA (6-11). The regulatory properties of HSP65 in AA are thought to involve the activation of T-cells cross-reactive with the endogenous 60 kDa heat shock protein (HSP60) (12). This hypothesis is supported by the finding that immunization with a recombinant vaccinia virus encoding human HSP60 (about 95% homologous to rat HSP60) prevents (13) or treats (14) AA. The inventor of the present invention have recently reported that DNA vaccination with human HSP60 prevents AA (15). Protection from AA was associated with the activation of T-cells responding to HSP60 (15). The human hsp60 molecule was formerly designated HSP65, but is now designated HSP60 in view of more accurate molecular weight information; by either designation, the protein is the same.

A preferable method for treating autoimmune diseases includes modulating the immune system of a patient to assist the patient's natural defense mechanisms. Traditional reagents and methods used to attempt to regulate an immune response in a patient also result in unwanted side effects and have limited effectiveness. For example, immunosuppressive reagents (e.g., cyclosporin A, azathioprine, and prednisone) used to treat patients with autoimmune diseases also suppress the patient's entire immune response, thereby increasing the risk of infection. In addition, immunopharmacological reagents used to treat cancer (e.g., interleukins) are short-lived in the circulation of a patient and are ineffective except in large doses. Due to the medical importance of immune regulation and the inadequacies of existing immunopharmacological reagents, reagents and methods to regulate specific parts of the immune system have been the subject of study for many years.

EP 262710 of Cohen et al. discloses the use of HSP65, or fragments thereof for the preparation of compositions for the alleviation, treatment and diagnosis of autoimmune diseases, especially arthritic conditions. EP 322990 of Cohen et al. discloses that a polypeptide having amino acid sequence 172-192 of HSP65 is capable of inducing resistance to auto-immune arthritis and similar auto-immune diseases. WO 92/04049 of Boog et al. discloses peptides derived from *Mycobacterium tuberculosis* protein HSP-65 containing at least 7 amino acid residues and inhibits antigen recognition by T lymphocytes in treatment of arthritis and organ rejection.

WO 01/57056 of Karin discloses a method of treating rheumatoid arthritis. The method comprising the step of expressing within the individual at least an immunologically recognizable portion of a cytokine from an exogenous polynucleotide encoding at least a portion of the cytokine, wherein a level of expression of the at least a portion of the cytokine is sufficient to induce the formation of anti-cytokine immunoglobulins which serve for neutralizing or ameliorating the activity of a respective and/or cross reactive endogenous cytokine, to thereby treat rheumatoid arthritis. U.S. Pat. No. 6,316,420 to Karin and coworkers further discloses DNA cytokine vaccines and use of same for protective immunity against multiple sclerosis.

WO 02/16549 of Cohen et al., assigned to the assignee of the present invention, relates to DNA vaccines useful for the prevention and treatment of ongoing autoimmune diseases. The compositions and methods of the invention feature the CpG oligonucleotide, preferably in a motif flanked by two 5' purines and two 3' pyrimidines. The vaccines optionally further comprise DNA encoding a peptide or a polypeptide selected from the group consisting of Hsp60, p277 or p277 variants. That disclosure is directed to methods and compositions for the ameliorative treatment of ongoing autoimmune disease in general and Insulin Dependent Diabetes Mellitus (IDDM) in particular.

U.S. Pat. No. 5,993,803 discloses that when HSP60, or peptides and analogs thereof, are administered in a recipient subject before transplantation of an organ or tissue, autoimmunity to HSP60 is down-regulated, resulting in the prevention or suppression of graft rejection of the transplanted organ or tissue.

WO 00/27870 of Naparstek and colleagues discloses a series of related peptides derived from heat shock proteins HSP65 and HSP60, their sequences, antibodies, and use as vaccines for conferring immunity against autoimmune and/or inflammatory disorders such as arthritis. These peptides are intended by the inventors to represent the shortest sequence or epitope that is involved in protection of susceptible rat strains against adjuvant induced arthritis. These sequences further disclose what the inventors identify as the common "protective motif".

There exists a long-felt need for an effective means of curing or ameliorating T cell mediated inflammatory autoimmune diseases. None of the background art discloses DNA vaccines encoding heat shock proteins for treating T cell mediated inflammatory autoimmune diseases. Such a treatment should ideally control the inappropriate T cell response, rather than merely reducing the symptoms.

SUMMARY OF THE INVENTION

DNA vaccination represents a novel and unexpectedly effective means of expressing antigen in vivo for the generation of both humoral and cellular immune responses. The present invention uses this technology to elicit protective immunity against T cell-mediated autoimmune diseases. The compositions and methods of the present invention are effective in any T-cell mediated inflammatory autoimmune disease including but not limited to: rheumatoid arthritis, collagen II arthritis, multiple sclerosis, autoimmune neuritis, systemic lupus erythematosus, psoriasis, juvenile onset diabetes, Sjogren's disease, thyroid disease, sarcoidosis, autoimmune uveitis, inflammatory bowel disease (Crohn's and ulcerative colitis) or autoimmune hepatitis.

In one aspect, the present invention is related to DNA vaccines encoding heat shock proteins for treating T cell-mediated inflammatory autoimmune diseases. According to various specific embodiments of the present invention, the heat shock proteins are mammalian heat shock proteins, preferably the full-length heat shock protein 60 (HSP60), the full-length heat shock protein 70 (HSP70) or the full-length heat shock protein 90 (HSP90). The heat shock proteins according to the present invention are preferably human heat shock proteins, however other mammalian heat shock proteins are within the scope of the present invention. According to another embodiment, the full-length heat shock protein 70 (HSP70) has the amino acid sequence selected from SEQ ID NO:4-SEQ ID NO:11. According to another embodiment, the full-length heat shock protein 70 (HSP70) has the amino acid sequence as set forth as SEQ ID NO:4. According to another embodiment, the full-length heat shock protein 90 (HSP90) has the amino acid sequence as set forth as SEQ ID NO:12.

According to various additional embodiments of the present invention, the DNA vaccines encode active fragments of HSP60, HSP70 or HSP90. In certain specific embodiments, the DNA vaccines encode active fragments of HSP60. Preferred fragments of HSP60 correspond to amino acids 1-140 of HSP60 (SEQ ID NO:1), amino acids 130-260 of HSP60 (SEQ ID NO:2) or amino acids 31-50 of HSP60 (SEQ ID NO:3).

The treatment with the DNA vaccines of the present invention provides long-term expression of specific heat shock proteins or active fragments thereof. Such long-term expression allows for the maintenance of an effective, but non-toxic, dose of the encoded polypeptides to treat the disease and limits the frequency of administration of the therapeutic composition needed to treat an animal. In addition, because of the lack of toxicity, therapeutic compositions of the present invention can be used in repeated treatments.

In another aspect, the present invention is related to novel recombinant constructs comprising a nucleic acid sequence encoding at least part of a heat shock protein being operatively linked to at least one transcription control element. According to various embodiments of the present invention, the heat shock protein is a mammalian heat shock protein, preferably the full-length HSP60, the full-length HSP70 or the full-length HSP90. The heat shock proteins according to the present invention are preferably human heat shock proteins, however other mammalian heat shock proteins are within the scope of the present invention.

According to various embodiments of the present invention, the recombinant constructs encoding active fragments of HSP60, HSP70 or HSP90. In a preferred embodiment, the recombinant constructs encode active fragments of HSP60, said active fragments selected from: amino acids 1-140 of HSP60 (SEQ ID NO:1), amino acids 130-260 of HSP60 (SEQ ID NO:2) or amino acids 31-50 of HSP60 (SEQ ID NO:3), the nucleic acid sequence being operatively linked to at least one transcription control element.

According to various specific embodiments, the constructs of the present invention comprise at least one transcription control element selected from the group consisting of: RSV control sequences, CMV control sequences, retroviral LTR sequences, SV-40 control sequences and β-actin control sequences.

In another aspect, the present invention is related to an eukaryotic expression vector comprising the recombinant constructs of the present invention. According to various embodiments, the eukaryotic expression vector is selected from pcDNA3, pcDNA3.1(+/−), pZeoSV2(+/−), pSecTag2, pDisplay, pEF/myc/cyto, pCMV/myc/cyto, pCR3.1, pCI, pBK-RSV, pBK-CMV and pTRES.

Another aspect of the present invention provides a pharmaceutical composition effective for treating a T cell-mediated inflammatory autoimmune disease, the composition comprising (a) a recombinant construct comprising an isolated nucleic acid sequence encoding a heat shock protein, or an active fragment thereof, the nucleic acid sequence being operatively linked to one or more transcription control sequences; and (b) a pharmaceutically acceptable carrier.

In one embodiment, the nucleic acid sequence encodes the full-length HSP60, the full-length HSP70 or the full-length HSP90. In another embodiment, the nucleic acid sequence encoding an active fragment of HSP60, HSP70 or HSP90. In a preferred embodiment, the nucleic acid sequence encoding amino acids 1-140 of human HSP60 (SEQ ID NO:1). In another preferred embodiment, the nucleic acid sequence encoding amino acids 130-260 of human HSP60 (SEQ ID NO:2). In yet another preferred embodiment, the nucleic acid sequence encoding amino acids 31-50 of human HSP60 (SEQ ID NO:3).

The pharmaceutical compositions comprising the recombinant constructs according to the present invention may advantageously comprise liposomes, micelles, emulsions or cells. Still further embodiments utilize a virus as is known in the art in order to introduce and express the nucleic acid sequences according to the present invention in the host cells.

In another aspect, the present invention is related to a method of inhibiting or preventing the symptoms of a T-cell mediated inflammatory autoimmune disease, the method comprising administering to an individual in need of said treatment, preferably a human individual, a therapeutic composition comprising a recombinant construct, said recombinant construct comprising an isolated nucleic acid sequence encoding a heat shock protein, or a fragment thereof, thereby inhibiting or preventing the symptoms of said autoimmune disease.

In one embodiment, the nucleic acid sequence encodes the full-length HSP60, the full-length HSP70 or the full-length HSP90. In another embodiment, the nucleic acid sequence encoding the full-length HSP70 has the nucleic acid sequence as set forth as SEQ ID NO:13. In another embodiment, the nucleic acid sequence encoding the full-length HSP90 has the nucleic acid sequence as set forth as SEQ ID NO:14.

According to various embodiments, the compositions and methods of the present invention are effective in any T-cell mediated inflammatory autoimmune disease such as: rheumatoid arthritis, collagen II arthritis, multiple sclerosis, autoimmune neuritis, systemic lupus erythematosus, psoriasis, juvenile onset diabetes, Sjogren's disease, thyroid disease, sarcoidosis, autoimmune uveitis, inflammatory bowel disease (Crohn's and ulcerative colitis) or autoimmune hepatitis.

The present invention is particularly exemplified by the animal disease model of adjuvant arthritis (AA), a T cell-mediated autoimmune disease that serves as an experimental model for rheumatoid arthritis. This model is intended as a non-limitative example used for illustrative purposes of the principles of the invention In one embodiment, the therapeutic composition of the present invention is administered to an individual at risk of developing a T-cell mediated inflammatory autoimmune disease, thus serving as a preventive treatment. In another embodiment, the therapeutic composition of the present invention is administered to an individual during the initial stages of the disease or after the appearance of disease symptoms.

According to another aspect, the present invention provides a method for treating a T cell-mediated inflammatory autoimmune disease comprising the steps of (a) obtaining cells from an individual; (b) transfecting the cells ex vivo with a recombinant construct comprising an isolated nucleic acid sequence encoding a heat shock protein, or a fragment thereof, the nucleic acid sequence being operatively linked to one or more transcription control sequences; and (c) reintroducing the transfected cells to the individual.

According to another aspect, the present invention provides a method for treating a T cell-mediated inflammatory autoimmune disease comprising the steps of (a) obtaining cells from an individual; (b) infecting the cells ex vivo with a virus comprising a recombinant construct comprising an isolated nucleic acid sequence encoding a heat shock protein, or a fragment thereof, the nucleic acid sequence being operatively linked to one or more transcription control sequences; and (c) reintroducing the infected cells to the individual.

According to another aspect, the present invention provides a method for treating a T cell-mediated inflammatory autoimmune disease comprising administering to an individual in need thereof a therapeutic composition comprising (a) a fragment of mammalian HSP60 having amino acid sequence selected from SEQ ID NO:1, SEQ ID NO:2 and SEQ ID NO:3; and (b) a pharmaceutically acceptable carrier.

According to another aspect, the present invention provides a method of treating arthritis, said method comprising administering to an individual in need thereof a therapeutic composition comprising (a) a fragment of mammalian HSP60 having amino acid sequence Lys Phe Gly Ala Asp Ala Arg Ala Leu Met Leu Gln Gly Val Asp Leu Leu Ala Asp Ala corresponding to amino acid residus 31-50 of human HSP60 (denoted as SEQ ID NO:3); and (b) a pharmaceutically acceptable carrier, thereby treating arthritis. According to various embodiments, the carrier comprises a delivery vehicle that delivers the fragment to the individual.

According to another aspect, the present invention provides a method of treating arthritis, said method comprising the steps of (a) obtaining cells from an individual; (b) exposing the cells ex vivo with an active amount of a fragment of mammalian HSP60 having amino acid sequence corresponding to amino acids 31-50 of HSP60 (denoted as SEQ ID NO:3); and (c) reintroducing the exposed cells to the individual, thereby treating arthritis. In a preferred embodiment the cells are autologous T cells. In another preferred embodiment, the mammalian HSP60 is human HSP60.

These and further embodiments will be apparent from the detailed description and examples that follow.

DETAILED DESCRIPTION OF THE INVENTION

Figure 1:
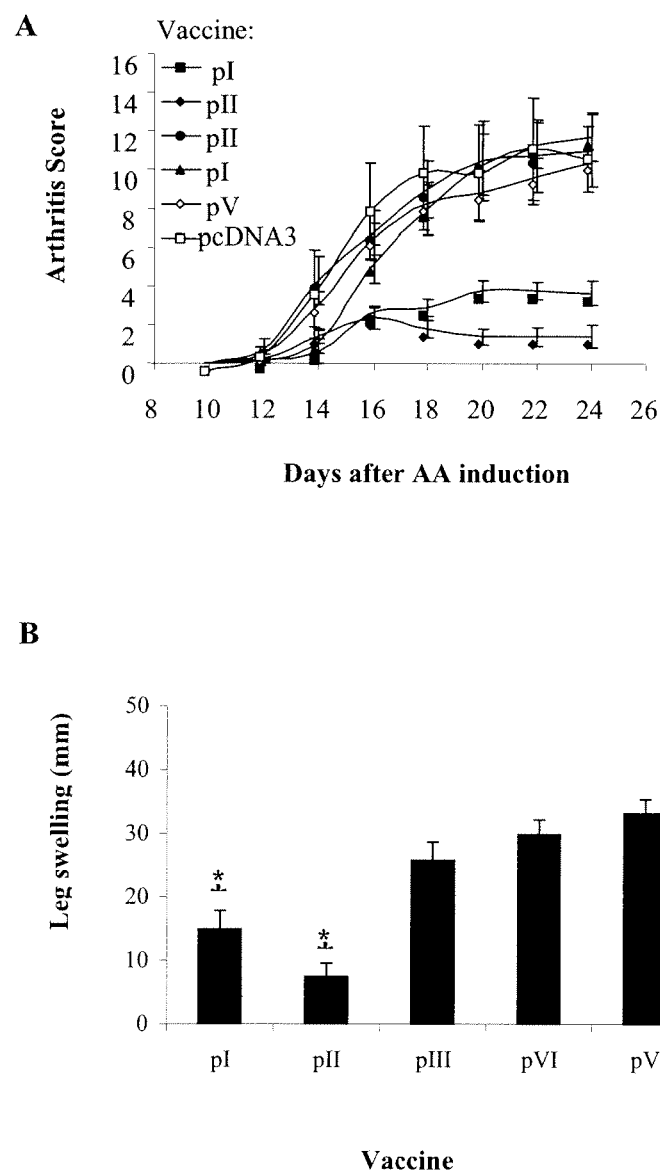
FIG. 1: Prevention of AA by vaccination with pI and pII. A. Time course of AA. Rats were vaccinated in the quadriceps three times (on days −40, −26 −12 relative to AA induction) with 150 µg of pcDNA3, pI, pII, pIII, pIV or pV. On day 0, AA was induced by injecting 1 mg of Mt suspended in 100 µl of IFA, and arthritis scores were assessed every two or three days starting at day 10. Bars show the mean±SEM assessment of disease severity. B. Leg swelling measured at day 26 after AA induction.

According to the present invention it is now disclosed that it is possible to treat or prevent T cell-mediated inflammatory autoimmune diseases by using DNA vaccines encoding a heat shock protein, or active fragments thereof. The compositions and methods of the present invention are effective in any T-cell mediated inflammatory autoimmune disease including but not limited to: rheumatoid arthritis, collagen II arthritis, multiple sclerosis, autoimmune neuritis, systemic lupus erythematosus, psoriasis, juvenile onset diabetes, Sjogren's disease, thyroid disease, sarcoidosis, autoimmune uveitis, inflammatory bowel disease (Crohn's and ulcerative colitis) or autoimmune hepatitis.

The present invention is based in part on studies of the role of DNA vaccines encoding a heat shock protein, or fragments thereof in adjuvant induced arthritis in experimental rats. Specifically, the present invention is based on the unexpected discovery that certain DNA constructs encoding specific heat shock proteins, such as HSP60, HSP70 or HSP90, or active fragments thereof are useful in decreasing the symptoms associated with arthritis. The protective effect of these DNA constructs was reflected for example by a significant reduction in ankle swelling.

It is now disclosed that it is possible to treat or prevent T cell-mediated diseases by using DNA vaccines encoding mammalian heat shock proteins or active fragments thereof. The present invention is based in part on studies of the role of the immune response to HSP60 in adjuvant induced arthritis in experimental rats, using DNA vaccines encoding human HSP60, human HSP70, human HSP90 or active fragments thereof. The results led to the identification of novel constructs encoding at least part of the HSP60 sequence that could effectively suppress AA. In addition, specific HSP60 fragments were found to be effective in suppressing AA. The immune effects associated with specific DNA or peptide suppression of AA were complex and included enhanced T-cell proliferation to a variety of disease-associated antigens. Effective vaccination with HSP60 DNA fragments or the HSP60 peptide led to up-regulation of IFNγ secretion to HSP60 and, concomitantly to down-regulation of IFNγ secretion to mycobacterial HSP65 epitopes. There were also variable changes in the profiles of IL-10 secretion to those antigens. The production of TGFβ1, however, was enhanced to both HSP60 and HSP65 epitopes. The regulation of AA might be due to the induction of regulatory T-cells directed to HSP60, secreting both Th1 and Th2 cytokines that shifted the immune response towards mycobacterial antigens to a Th2 non-pathogenic response.

The present invention provides an effective method of DNA vaccination for T cell-mediated inflammatory autoimmune diseases, which avoids many of the problems associated with the previously suggested methods of treatment. By vaccinating, rather than passively administering heterologous antibodies, the host's own immune system is mobilized to suppress the autoaggressive T cells. Thus, the suppression is persistent and may involve any and all immunological mechanisms in effecting that suppression. This multi-faceted response is more effective than the uni-dimensional suppression achieved by passive administration of monoclonal antibodies or extant-derived regulatory T cell clones.

In one aspect, the present invention is related to novel recombinant constructs comprising a nucleic acid sequence corresponding to mammalian heat shock proteins, the nucleic acid sequence being operatively linked to at least one transcription control element. Preferably, the recombinant constructs of the present invention correspond to human heat shock proteins. However, recombinant constructs corresponding to the rat or mouse heat shock proteins may also be used in the present invention.

The nucleic acid sequence corresponding to mammalian heat shock proteins may include DNA, RNA, or derivatives of either DNA or RNA. An isolated nucleic acid sequence encoding heat shock proteins can be obtained from its natural source, either as an entire (i.e., complete) gene or a portion thereof. A nucleic acid molecule can also be produced using recombinant DNA technology (e.g., polymerase chain reaction (PCR) amplification, cloning) or chemical synthesis. Nucleic acid sequences include natural nucleic acid sequences and homologues thereof, including, but not limited to, natural allelic variants and modified nucleic acid sequences in which nucleotides have been inserted, deleted, substituted, and/or inverted in such a manner that such modifications do not substantially interfere with the nucleic acid molecule's ability to encode a functional heat shock protein or an active fragment thereof.

A nucleic acid sequence homologue can be produced using a number of methods known to those skilled in the art (see, for example, Sambrook et al., Molecular Cloning: A Laboratory Manual, Cold Spring Harbor Labs Press, 1989). For example, nucleic acid sequences can be modified using a variety of techniques including, but not limited to, classic mutagenesis techniques and recombinant DNA techniques, such as site-directed mutagenesis, chemical treatment of a nucleic acid molecule to induce mutations, restriction enzyme cleavage of a nucleic acid fragment, ligation of nucleic acid fragments, polymerase chain reaction (PCR) amplification and/or mutagenesis of selected regions of a nucleic acid sequence, synthesis of oligonucleotide mixtures and ligation of mixture groups to "build" a mixture of nucleic acid molecules and combinations thereof. Nucleic acid molecule homologues can be selected from a mixture of modified nucleic acids by screening for the function of the protein encoded by the nucleic acid.

The present invention includes a nucleic acid sequence operatively linked to one or more transcription control sequences to form a recombinant molecule. The phrase "operatively linked" refers to linking a nucleic acid sequence to a transcription control sequence in a manner such that the molecule is able to be expressed when transfected (i.e., transformed, transduced or transfected) into a host cell. Transcription control sequences are sequences which control the initiation, elongation, and termination of transcription. Particularly important transcription control sequences are those which control transcription initiation, such as promoter, enhancer, operator and repressor sequences. Suitable transcription control sequences include any transcription control sequence that can function in at least one of the recombinant cells of the present invention. A variety of such transcription control sequences are known to those skilled in the art. Preferred transcription control sequences include those which function in animal, bacteria, helminth, insect cells, and preferably in animal cells. More preferred transcription control sequences include, but are not limited to RSV control sequences, CMV control sequences, retroviral LTR sequences, SV-40 control sequences and β-actin control sequences as well as other sequences capable of controlling gene expression in eukaryotic cells. Additional suitable transcription control sequences include tissue-specific promoters and enhancers (e.g., T cell-specific enhancers and promoters). Transcription control sequences of the present invention can also include naturally occurring transcription control sequences naturally associated with a gene encoding a heat shock protein of the present invention.

The present invention is further related to an expression vector comprising the recombinant constructs of the present invention. Suitable eukaryotic expression vector is for example: pcDNA3, pcDNA3.1(+/−), pZeoSV2(+/−), pSecTag2, pDisplay, pEF/myc/cyto, pCMV/myc/cyto, pCR3.1, pCI, pBK-RSV, pBK-CMV, pTRES or their derivatives.

According to the present invention, a host cell can be transfected in vivo (i.e., in an animal) or ex vivo (i.e., outside of an animal). Transfection of a nucleic acid molecule into a host cell can be accomplished by any method by which a nucleic acid molecule can be inserted into the cell. Transfection techniques include, but are not limited to, transfection, electroporation, microinjection, lipofection, adsorption, and protoplast fusion. Preferred methods to transfect host cells in vivo include lipofection and adsorption.

It may be appreciated by one skilled in the art that use of recombinant DNA technologies can improve expression of transfected nucleic acid molecules by manipulating, for example, the number of copies of the nucleic acid molecules within a host cell, the efficiency with which those nucleic acid molecules are transcribed, the efficiency with which the resultant transcripts are translated, and the efficiency of post-translational modifications. Recombinant techniques useful for increasing the expression of nucleic acid molecules of the present invention include, but are not limited to, operatively linking nucleic acid molecules to high-copy number plasmids, integration of the nucleic acid molecules into one or more host cell chromosomes, addition of vector stability sequences to plasmids, substitutions or modifications of transcription control signals (e.g., promoters, operators, enhancers), substitutions or modifications of translational control signals (e.g., ribosome binding sites, Shine-Dalgarno sequences), modification of nucleic acid molecules of the present invention to correspond to the codon usage of the host cell, and deletion of sequences that destabilize transcripts.

According to yet another aspect of the present invention there is provided a pharmaceutical composition suitable for effecting the above methods of the present invention. The composition includes a recombinant construct including an isolated nucleic acid sequence encoding a heat shock protein or a fragment thereof, the nucleic acid sequence being operatively linked to one or more transcription control sequences, and a pharmaceutically acceptable carrier.

In one embodiment of the invention, the composition is useful for treating a T cell-mediated inflammatory autoimmune disease such as multiple sclerosis, rheumatoid arthritis, collagen II arthritis, autoimmune neuritis, systemic lupus erythematosus, psoriasis, juvenile onset diabetes, Sjogren's disease, thyroid disease, sarcoidosis, autoimmune uveitis, inflammatory bowel disease (Crohn's and ulcerative colitis) or autoimmune hepatitis.

The therapeutic composition of the invention is administered to an individual in need of said treatment. According to still further features in the described preferred embodiments the individual is selected from the group consisting of humans, dogs, cats, sheep, cattle, horses and pigs.

In another embodiment of the present invention, a therapeutic composition further comprises a pharmaceutically acceptable carrier. As used herein, a "carrier" refers to any substance suitable as a vehicle for delivering a nucleic acid sequence of the present invention to a suitable in vivo site. As such, carriers can act as a pharmaceutically acceptable excipient of a therapeutic composition containing a nucleic acid molecule of the present invention. Preferred carriers are capable of maintaining a nucleic acid molecule of the present invention in a form that, upon arrival of the nucleic acid molecule to a cell, the nucleic acid molecule is capable of entering the cell and being expressed by the cell. Carriers of the present invention include: (1) excipients or formularies that transport, but do not specifically target a nucleic acid molecule to a cell (referred to herein as non-targeting carriers); and (2) excipients or formularies that deliver a nucleic acid molecule to a specific site in an animal or a specific cell (i.e., targeting carriers). Examples of non-targeting carriers include, but are not limited to, water, phosphate buffered saline, Ringer's solution, dextrose solution, serum-containing solutions, Hank's solution, other aqueous physiologically balanced solutions, oils, esters and glycols. Aqueous carriers can contain suitable auxiliary substances required to approximate the physiological conditions of the recipient, for example, by enhancing chemical stability and isotonicity.

Suitable auxiliary substances include, for example, sodium acetate, sodium chloride, sodium lactate, potassium chloride, calcium chloride, and other substances used to produce phosphate buffer, Tris buffer, and bicarbonate buffer. Auxiliary substances can also include preservatives, such as thimerosal, m- and o-cresol, formalin and benzol alcohol. Preferred auxiliary substances for aerosol delivery include surfactant substances non-toxic to an animal, for example, esters or partial esters of fatty acids containing from about six to about twenty-two carbon atoms. Examples of esters include, caproic, octanoic, lauric, palmitic, stearic, linoleic, linolenic, olesteric, and oleic acids. Other carriers can include metal particles (e.g., gold particles) for use with, for example, a biolistic gun through the skin. Therapeutic compositions of the present invention can be sterilized by conventional methods.

Targeting carriers are herein referred to as "delivery vehicles". Delivery vehicles of the present invention are capable of delivering a therapeutic composition of the present invention to a target site in an animal. A "target site" refers to a site in an animal to which one desires to deliver a therapeutic composition. For example, a target site can be a cancer cell, a tumor, or a lesion caused by an infectious agent, or an area around such cell, tumor or lesion, which is targeted by direct injection or delivery using liposomes or other delivery vehicles. Examples of delivery vehicles include, but are not limited to, artificial and natural lipid-containing delivery vehicles. Natural lipid-containing delivery vehicles include cells and cellular membranes. Artificial lipid-containing delivery vehicles include liposomes and micelles. A delivery vehicle of the present invention can be modified to target to a particular site in an animal, thereby targeting and making use of a nucleic acid molecule of the present invention at that site. Suitable modifications include manipulating the chemical formula of the lipid portion of the delivery vehicle and/or introducing into the vehicle a compound capable of specifically targeting a delivery vehicle to a preferred site, for example, a preferred cell type. Specifically targeting refers to causing a delivery vehicle to bind to a particular cell by the interaction of the compound in the vehicle to a molecule on the surface of the cell. Suitable targeting compounds include ligands capable of selectively (i.e., specifically) binding another molecule at a particular site. Examples of such ligands include antibodies, antigens, receptors and receptor ligands. For example, an antibody specific for an antigen found on the surface of a cancer cell can be introduced to the outer surface of a liposome delivery vehicle so as to target the delivery vehicle to the cancer cell. Tumor cell ligands include ligands capable of binding to a molecule on the surface of a tumor cell. Manipulating the chemical formula of the lipid portion of the delivery vehicle can modulate the extracellular or intracellular targeting of the delivery vehicle. For example, a chemical can be added to the lipid formula of a liposome that alters the charge of the lipid bilayer of the liposome so that the liposome fuses with particular cells having particular charge characteristics.

According to one embodiment, fat emulsions may be used as a vehicle for DNA vaccines. Two examples of such emulsions are the available commercial fat emulsions known as Intralipid and Lipofundin. "Intralipid" is a registered trademark of Kabi Pharmacia, Sweden, for a fat emulsion for intravenous nutrition, described in U.S. Pat. No. 3,169,094. "Lipofundin" is a registered trademark of B. Braun Melsungen, Germany. Both contain soybean oil as fat (100 or 200 g in 1,000 ml distilled water: 10% or 20%, respectively). Egg-yolk phospholipids are used as emulsifiers in Intralipid (12 g/l distilled water) and egg-yolk lecithin in Lipofundin (12 g/l distilled water). Isotonicity results from the addition of glycerol (25 g/l) both in Intralipid and Lipofundin.

According to another embodiment, the delivery vehicle of the present invention may be a liposome. A liposome is capable of remaining stable in an animal for a sufficient amount of time to deliver a nucleic acid sequence of the present invention to a preferred site in the animal. A liposome of the present invention is preferably stable in the animal into which it has been administered for at least about 30 minutes, more preferably for at least about 1 hour and even more preferably for at least about 24 hours.

A liposome of the present invention comprises a lipid composition that is capable of fusing with the plasma membrane of the targeted cell to deliver a nucleic acid molecule into a cell. Preferably, the transfection efficiency of a liposome of the present invention is about 0.5 microgram (µg) of DNA per 16 nanomole (nmol) of liposome delivered to about $10^6$ cells, more preferably about 1.0 µg of DNA per 16 nmol of liposome delivered to about $10^6$ cells, and even more preferably about 2.0 µg of DNA per 16 nmol of liposome delivered to about $10^6$ cells.

A preferred liposome of the present invention is between about 100 and 500 nanometers (nm), more preferably between about 150 and 450 nm and even more preferably between about 200 and 400 nm in diameter.

Suitable liposomes for use with the present invention include any liposome. Preferred liposomes of the present invention include those liposomes standardly used in, for example, gene delivery methods known to those of skill in the art. More preferred liposomes comprise liposomes having a polycationic lipid composition and/or liposomes having a cholesterol backbone conjugated to polyethylene glycol.

Complexing a liposome with a nucleic acid sequence of the present invention can be achieved using methods standard in the art. A suitable concentration of a nucleic acid molecule of the present invention to add to a liposome includes a concentration effective for delivering a sufficient amount of nucleic acid molecule to a cell such that the cell can produce sufficient heat shock protein to regulate effector cell immunity in a desired manner. Preferably, from about 0.1 µg to about 10 µg of nucleic acid sequence of the present invention is combined with about 8 nmol liposomes, more preferably from about 0.5 µg to about 5 µg of nucleic acid molecule is combined with about 8 nmol liposomes, and even more preferably about 1.0 µg of nucleic acid molecule is combined with about 8 nmol liposomes.

According to another embodiment, the delivery vehicle comprises a recombinant cell vaccine. Preferred recombinant cell vaccines of the present invention include cell vaccines, in which allogeneic (i.e., cells derived from a source other than a patient, but that are histiotype compatible with the patient) or autologous (i.e., cells isolated from a patient) cells are transfected with recombinant molecules contained in a therapeutic composition, irradiated and administered to a patient by, for example, intradermal, intravenous or subcutaneous injection. Therapeutic compositions to be administered by cell vaccine, include recombinant molecules of the present invention without carrier.

In order to treat an animal with disease, a therapeutic composition of the present invention is administered to the animal in an effective manner such that the composition is capable of treating that animal from disease. For example, a recombinant molecule, when administered to an animal in an effective manner, is able to stimulate effector cell immunity in a manner that is sufficient to alleviate the disease afflicting the animal. According to the present invention, treatment of a disease refers to alleviating a disease and/or preventing the development of a secondary disease resulting from the occurrence of a primary disease. An effective administration protocol (i.e., administering a therapeutic composition in an effective manner) comprises suitable dose parameters and modes of administration that result in treatment of a disease. Effective dose parameters and modes of administration can be determined using methods standard in the art for a particular disease. Such methods include, for example, determination of survival rates, side effects (i.e., toxicity) and progression or regression of disease. In particular, the effectiveness of dose parameters and modes of administration of a therapeutic composition of the present invention when treating cancer can be determined by assessing response rates. Such response rates refer to the percentage of treated patients in a population of patients that respond with either partial or complete remission.

In accordance with the present invention, a suitable single dose size is a dose that is capable of treating an animal with disease when administered one or more times over a suitable time period. Doses can vary depending upon the disease being treated. Doses of a therapeutic composition of the present invention suitable for use with direct injection techniques can be used by one of skill in the art to determine appropriate single dose sizes for systemic administration based on the size of an animal. A suitable single dose of a therapeutic composition is a sufficient amount of heat shock protein-encoding recombinant sequence to reduce, and preferably eliminate, the T-cell mediated autoimmune disease following transfection of the recombinant molecules into cells. A preferred single dose of heat shock protein-encoding recombinant molecule is an amount that, when transfected into a target cell population leads to the production of from about 250 femtograms (fg) to about 1 µg, preferably from about 500 fg to about 500 picogram (pg), and more preferably from about 1 pg to about 100 pg of a heat shock protein or fragment thereof per transfected cell.

A preferred single dose of heat shock protein-encoding recombinant molecule complexed with liposomes, is from about 100 µg of total DNA per 800 nmol of liposome to about 2 mg of total recombinant molecules per 16 micromole (µmol) of liposome, more preferably from about 150 µg per 1.2 µmol of liposome to about 1 mg of total recombinant molecules per 8 µmol of liposome, and even more preferably from about 200 µg per 2 µmol of liposome to about 400 µg of total recombinant molecules per 3.2 µmol of liposome.

A preferred single dose of heat shock protein-encoding recombinant molecule in a non-targeting carrier to administer to an animal, is from about 100 µg to about 4 mg of total recombinant molecules, more preferably from about 150 µg to about 3 mg of total recombinant molecules, and even more preferably from about 200 µg to about 2 mg of total recombinant molecules.

It will be obvious to one of skill in the art that the number of doses administered to an animal is dependent upon the extent of the disease and the response of an individual patient to the treatment. Thus, it is within the scope of the present invention that a suitable number of doses includes any number required to cause regression of a disease. A preferred protocol is monthly administrations of single doses (as described above) for up to about 1 year. A preferred number of doses of a therapeutic composition comprising heat shock protein-encoding recombinant molecule in a non-targeting carrier or complexed with liposomes is from about 1 to about 10 administrations per patient, preferably from about 2 to about 8 administrations per patient, and even more preferably from about 3 to about 5 administrations per person. Preferably, such administrations are given once every 2 weeks until signs of remission appear, then once a month until the disease is gone.

A therapeutic composition is administered to an animal in a fashion to enable expression of the administered recombinant molecule of the present invention into a curative protein in the animal to be treated for disease. A therapeutic composition can be administered to an animal in a variety of methods including, but not limited to, local administration of the composition into a site in an animal, and systemic administration.

Therapeutic compositions to be delivered by local administration include: (a) recombinant molecules of the present invention in a non-targeting carrier (e.g., as "naked" DNA molecules, such as is taught, for example in Wolff et al., 1990, Science 247, 1465-1468); and (b) recombinant molecules of the present invention complexed to a delivery vehicle of the present invention. Suitable delivery vehicles for local administration comprise liposomes or emulsions. Delivery vehicles for local administration can further comprise ligands for targeting the vehicle to a particular site.

Therapeutic compositions useful in systemic administration include recombinant molecules of the present invention complexed to a targeted delivery vehicle of the present invention. Suitable delivery vehicles for use with systemic administration comprise liposomes comprising ligands for targeting the vehicle to a particular site. Systemic administration is particularly advantageous when organs, in particular difficult to reach organs (e.g., heart, spleen, lung or liver) are the targeted sites of treatment.

Preferred methods of systemic administration, include intravenous injection, aerosol, oral and percutaneous (topical) delivery. Intravenous injections can be performed using methods standard in the art. Aerosol delivery can also be performed using methods standard in the art (see, for example, Stribling et al., Proc. Natl. Acad. Sci. USA 189: 11277-11281, 1992, which is incorporated herein by reference in its entirety). Oral delivery can be performed by complexing a therapeutic composition of the present invention to a carrier capable of withstanding degradation by digestive enzymes in the gut of an animal. Examples of such carriers include plastic capsules or tablets, such as those known in the art. Topical delivery can be performed by mixing a therapeutic composition of the present invention with a lipophilic reagent (e.g., DMSO) that is capable of passing into the skin.

Suitable embodiments, single dose sizes, number of doses and modes of administration of a therapeutic composition of the present invention useful in a treatment method of the present invention are disclosed in detail herein.

A therapeutic composition of the present invention is also advantageous for the treatment of autoimmune diseases in that the composition suppresses the harmful stimulation of T cells by autoantigens (i.e., a "self", rather than a foreign antigen). Heat shock protein-encoding recombinant molecules in a therapeutic composition, upon transfection into a cell, produce a heat shock protein or a fragment thereof that reduces the harmful activity of T cells involved in an autoimmune disease. A preferred therapeutic composition for use in the treatment of autoimmune disease comprises heat shock protein-encoding recombinant molecule of the present invention. A more preferred therapeutic composition for use in the treatment of autoimmune disease comprises heat shock protein-encoding recombinant molecule combined with a non-targeting carrier of the present invention, preferably saline or phosphate buffered saline.

A single dose of heat shock protein-encoding nucleic acid molecule in a non-targeting carrier to administer to an animal to treat an autoimmune disease is from about 0.1 µg to about 200 µg of total recombinant molecules per kilogram (kg) of body weight, more preferably from about 0.5 µg to about 150 µg of total recombinant molecules per kg of body weight, and even more preferably from about 1 µg to about 10 µg of total recombinant molecules per kg of body weight.

The number of doses of heat shock protein-encoding recombinant molecule in a non-targeting carrier to be administered to an animal to treat an autoimmune disease is an injection about once every 6 months, more preferably about once every 3 months, and even more preferably about once a month.

A preferred method to administer a therapeutic composition of the present invention to treat an autoimmune disease is by direct injection. Direct injection techniques are particularly important in the treatment of an autoimmune disease. Preferably, a therapeutic composition is injected directly into muscle cells in a patient, which results in prolonged expression (e.g., weeks to months) of a recombinant molecule of the present invention. Preferably, a recombinant molecule of the present invention in the form of "naked DNA" is administered by direct injection into muscle cells in a patient.

It is to be noted that the compositions and methods of the present invention do not include the obligatory presence of the CpG motif disclosed in WO 02/16549, in DNA vaccines suitable for the treatment of ongoing autoimmune diseases.

The following examples are presented in order to more fully illustrate certain embodiments of the invention. They should in no way, however, be construed as limiting the broad scope of the invention. One skilled in the art can readily devise many variations and modifications of the principles disclosed herein without departing from the scope of the invention.

EXAMPLES

Materials and Methods
Animals

Female Lewis rats were raised and maintained under pathogen-free conditions in the Animal Breeding Center of The Weizmann Institute of Science. One- to two-month old rats were used for DNA vaccination and peptide-vaccination experiments. The experiments were performed under the supervision and guidelines of the Animal Welfare Committee.

Antigens and Adjuvants

Peptides were synthesized as previously described (15). The HSP60 peptides used in these studies are listed in Table I. Two HSP65 peptides were also used: Mt176-190, EESNTFGLQLELTEG (16) and Mt3, AYDEEARRGLERGLNALADA. Purified recombinant HSP65 was generously provided by Prof. Ruurd van der Zee (Institute of Infectious Diseases and Immunology, Faculty of Veterinary Medicine, Utrecht, The Netherlands). Recombinant HSP60 was prepared in our laboratory as described (11). *M. tuberculosis* Strain H37Ra and incomplete Freund's adjuvant (IFA) were purchased from Difco (Detroit, Mich., USA). Tuberculin purified protein derivative (PPD) was provided by the Statens Seruminstitut (Copenhagen, Denmark). Ovalbumin (OVA) and Concanavalin A (Con A) were purchased from Sigma (Rehovot, Israel).

DNA Plasmids

The vector containing the human hsp60 gene (pHSP60) has been described (17). The construct encoding *Mycobacterium leprae* HSP65 (pHSP65) was kindly provided by Dr. Douglas Lowrie (Medical Research Council, London, UK). Five fragments of the human hsp60 gene were amplified by PCR from hsp60 cDNA in pGEM (Promega, Madison, Wis., USA) using specific oligonucleotides containing restriction sites for the enzymes BamHI (oligonucleotide 5') or HindIII (oligonucleotide 3'), and cloned into the pcDNA3 vector (Invitrogen, NV, Leek, The Netherlands) using standard molecular biology techniques (Table II). The 5' oligonucleotide also included an ATG sequence necessary for protein translation. The plasmids were sequenced to confirm correct insertion of the cDNA and transcribed in vitro to check that they are functional (data not shown).

Plasmid DNA was prepared in large scale and injected after pretreatment with cardiotoxin (Sigma, Rehovot, Israel). Briefly, rats were vaccinated in the quadriceps three times (on days −40, −26 −12 relative to AA induction) with 150 µg of pcDNA3, pI, pII, pIII, pIV or pV. Endotoxin levels were checked by *Limulus* Amoebocyte Lysate and found always to be under acceptable levels for in vivo use (less than 0.02 EU/µg DNA). AA was induced 12 days after the last injection of DNA. The empty vector pcDNA3 was used as a DNA vaccination control.

AA Induction and Assessment

AA was induced using 1 mg per rat of heat-killed Mt strain H37Ra (Difco). The day of AA induction was designated as day 0, and disease severity was assessed by direct observation of all 4 limbs in each animal. A relative score between 0 and 4 was assigned to each limb, based on the degree of joint inflammation, redness and deformity; thus the maximum possible score for an individual animal was 16. Arthritis was also quantified by measuring hind limb diameter with a caliper. Measurements were taken on the day of AA induction and 26 days later, and they are presented as the mean±SEM of the difference between the two values. The person who scored the disease was blinded to the identity of the groups.

T-Cell Proliferation

Popliteal and inguinal lymph node cells (LNC) taken 26 days after the induction of AA were cultured in quadruplicates in 200 µl round bottom microtiter wells (Costar Corp., Cambridge, USA) at $2\times10^5$ cells per well with or without antigen. The T-cell mitogen Concanavalin A (Con A) was used as a positive control for T-cell proliferation. Cultures were incubated for 96 hrs at 37° C. in a humidified atmosphere of 5% $CO_2$. T-cell responses were detected by incorporation of [methyl-$^3$H]-thymidine (Amersham, Buckinghamshire, UK; 1 µCi/well), which was added to the wells for the last 18 hours. The stimulation index (SI) was computed as the ratio of the mean c.p.m. of antigen- or mitogen-containing wells to control wells cultured with medium alone.

Transfer of Cells

Spleen cells were prepared from peptide-vaccinated rats 26 days after the induction of AA. The splenocytes ($10^7$ cells per ml) were activated with 2.5 μg/ml of Con A for 48 hr at 37° C. in a humidified atmosphere of 5% $CO_2$. The cells were washed with sterile PBS and injected iv into naïve rats ($5 \times 10^7$ cells per rat). Three days after the transfer of the splenocytes, AA was induced.

Cytokine Assays

Supernatants were collected after 72 hrs of stimulation with each of the antigens tested. Rat IL-10 and IFNγ were quantitated in culture supernatants by enzyme-linked immunosorbent assay (ELISA) using Pharmingen's OPTEIA kit (Pharmingen, San Diego, USA). Rat TGFβ1 was quantified using the TGFβ1 $E_{max}$® ImmunoAssay System (Promega, Madison, USA) according to the manufacturer's instructions. Cytokine levels in supernatants are expressed as pg/ml based on calibration curves constructed using recombinant cytokines as standards. The lower limits of detection for the experiments described in this paper were 15 pg/ml for TGFβ1, IL-10 and IFNγ.

Statistical Significance

The InStat 2.01 program was used for statistical analysis. Student's t-test and the Mann-Whitney test were carried out to assay significant differences between the different experimental groups.

Example 1: HSP60 DNA Fragments Inhibit AA

To learn whether fragments of HSP60 DNA could inhibit AA, the cDNA corresponding to the human hsp60 gene was divided into five fragments, each with a 30 pb overlap, and each was cloned into the pcDNA3 vector (Table II). In this way, five constructs corresponding to HSP60-derived fragments were generated overlapping by 10 aa: pI, aa 1-140; pII, aa 130-260; pIII, aa 250-410, pIV, aa 400-470 and pV, aa 460-540 (Table II). Lewis rats were vaccinated with one of the HSP60 fragment constructs or with pcDNA3 as a control, and AA was induced. FIG. 1A shows that the rats vaccinated with pI or pII manifested significantly decreased arthritis compared to rats vaccinated with constructs pIII, pIV or pV or with control pcDNA3. The protective effect of the vaccination with constructs pI and pII was also reflected by a significant reduction in ankle swelling (FIG. 1B), and by a reduction of the mean maximal score, which was lower in those rats vaccinated with pI and pII (p=0.0007 and p=0.0003, respectively, compared to rats vaccinated with pcDNA3).

Figure 2:
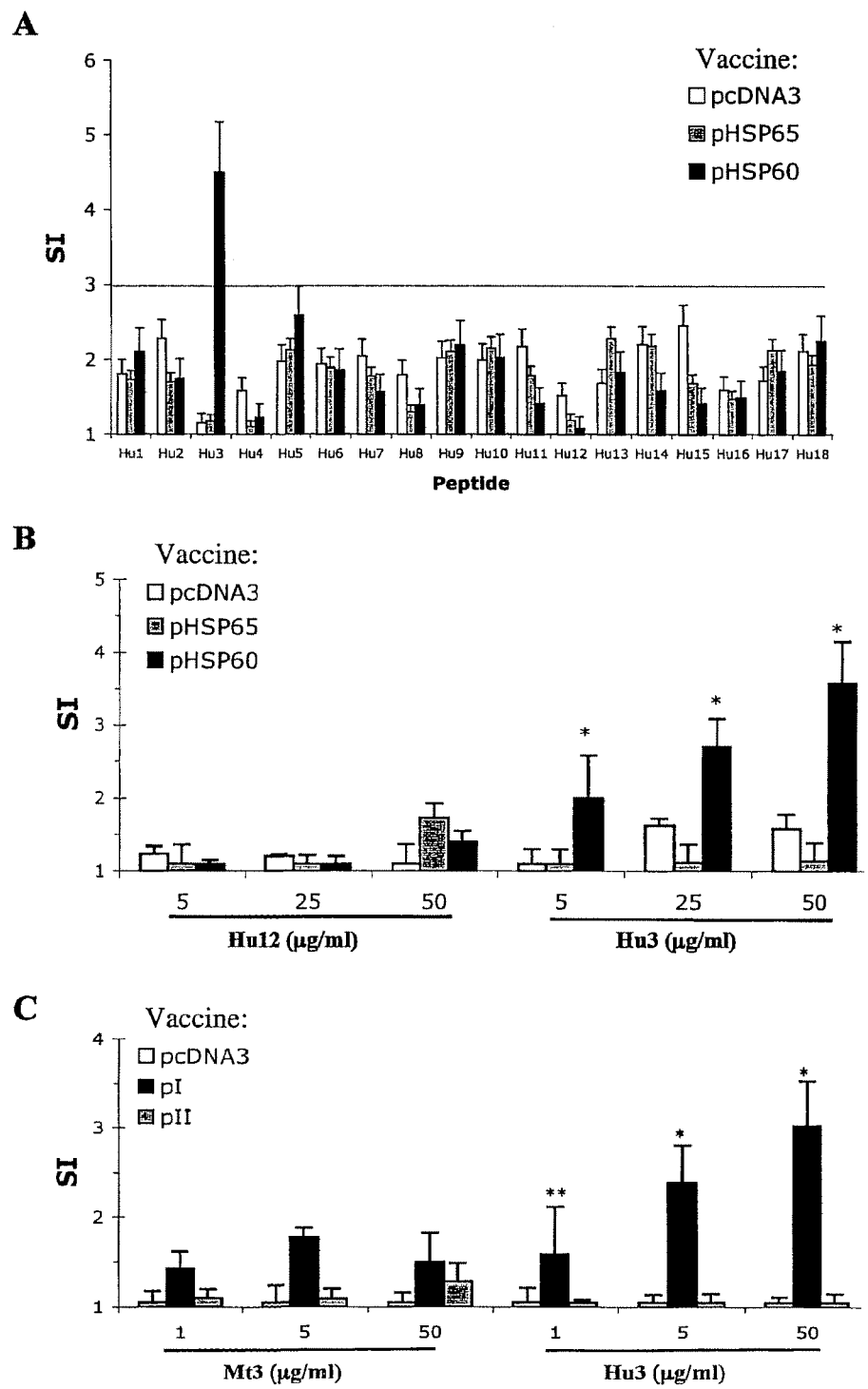
FIG. 2: pHSP60 and pI-vaccination activate T-cell responses to Hu3. A. Proliferative responses (Stimulation Index, SI) to overlaping peptides corresponding to the first 260 aa of HSP60. Rats vaccinated were killed and LNC were collected on day 26 after induction of AA. B. Dose-response to Hu3 of pHSP60, pHSP65 and pcDNA3-vaccinated rats. Rats vaccinated were killed and LNC were collected on day 26 after induction of AA. C. Dose-response to Hu3 of pI, pII and pcDNA3-vaccinated rats. Rats vaccinated were killed and LNC were collected on day 26 after induction of AA.

Example 2: In Vitro Proliferation of LNC Isolated from pHSP60- or PI-Vaccinated Rats in Response to Various HSP60 Peptides To learn whether the suppression of AA by DNA vaccination with pHSP60, pI or pII was associated with T-cell reactivity to a specific HSP60 epitope, the proliferation (Stimulation Index, SI) of LNC isolated from pHSP60-vaccinated rats was studied in response to a panel of overlapping peptides spanning the region of human HSP60 encoded by pI and pII (aa 1-275; Table I). Controls were LNC prepared from rats vaccinated with pcDNA3 or pHSP65 and challenged with Mt suspended in IFA to induce AA. FIG. 2A shows that only peptide Hu3 (aa 31-50 of human HSP60) induced a significant response in LNC taken from pHSP60-vaccinated rats; cells prepared from pHSP65 or pcDNA-vaccinated rats did not respond to Hu3. Note that the sequence of the HSP60 protein in the region 31-50 is identical in rat and human HSP60; thus Hu3 is a self-peptide (Table III). FIG. 2B shows a dose-dependant proliferative response to Hu3 using LNC isolated from pHSP60-vaccinated rats. No significant responses to the control peptide Hu12 (aa 166-185 of human HSP60) were detected. To confirm these results, T-cell proliferative responses were studied in LNC taken 26 days after the induction of AA from rats vaccinated with pI, pII or pcDNA3. FIG. 2C shows that Hu3, but not its mycobacterial homologue Mt3, triggered a significant proliferation of LNC taken from pI-immunized rats, but not by LNC from rats vaccinated with pII or pcDNA3. Non of the HSP60 peptides was specifically recognized by LNC taken from pII-immunized rats. In summary, these results show that pHSP60- and pI-vaccinated rats manifested up-regulated T-cell responses to the Hu3 peptide of HSP60.

Example 3: Peptide Hu3 Inhibits AA

Figure 3:
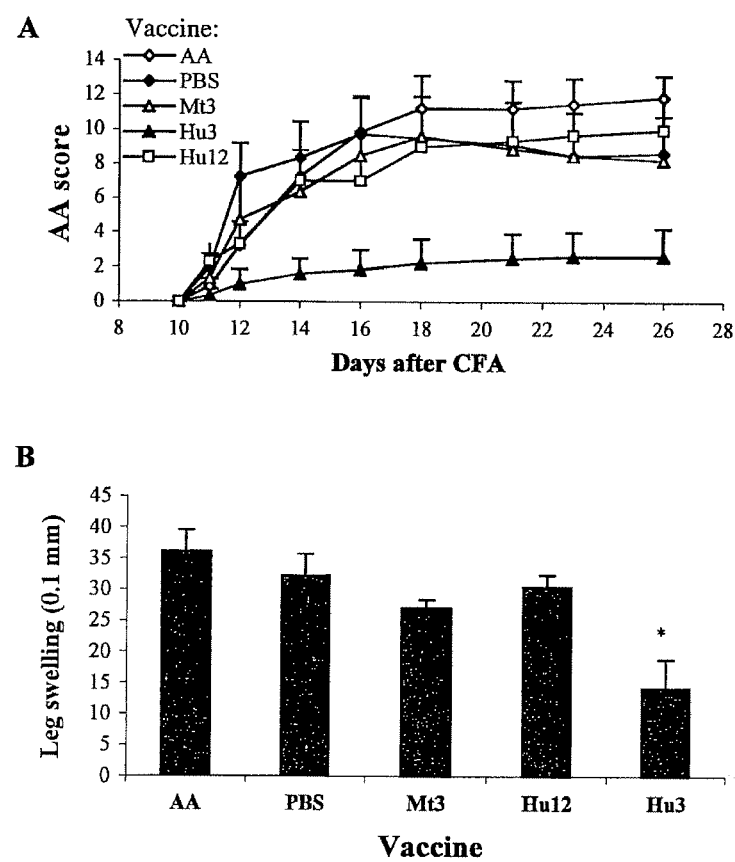
FIG. 3: Prevention of AA by vaccination with Hu3. A. Time course of AA. Rats were vaccinated once (on day −7 relative to AA induction) with 100 µg of Hu3, Hu12, Mt3 or PBS in 100 µl of IFA, or left unvaccinated (AA); and AA was induced on day 0 and arthritis scores were assessed. B. Leg swelling measured on day 26 after AA induction.

To establish a link between the immune response to Hu3 and prevention of AA, rats were vaccinated with Hu3, or with its mycobacterial counterpart Mt3 (Table III) or with Hu12 (Table I) as controls. Each rat received a single i.p. dose of 100 μg of peptide in IFA seven days (day −7) before the induction of AA (day 0). FIG. 3A shows that the Hu3-vaccinated rats developed significantly decreased disease compared to non-immunized rats or rats vaccinated with PBS, Hu12 or Mt3. This reduction in AA was also reflected by a significant reduction in ankle swelling (14.2±4.7 in Hu3-vaccinated rats vs 32.2±3.5 in PBS/IFA-vaccinated rats, p=0.02; FIG. 3B). Therefore, vaccination with Hu3 prevents AA.

Example 4: Adoptive Transfer of Peptide-Induced Regulation

Figure 4:
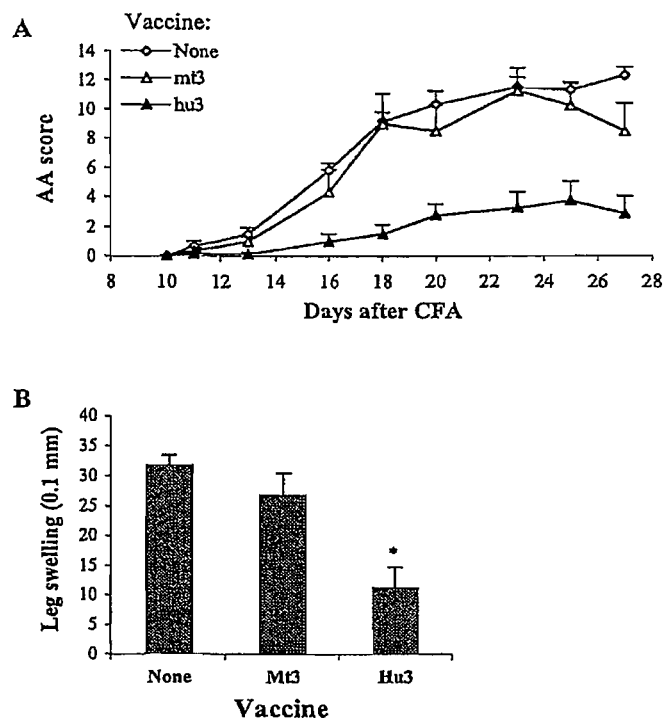
FIG. 4: Prevention of AA by transfer of Con A-activated splenocytes from Hu3-vaccinated rats. A. Time course of AA. Rats were vaccinated once (on day −7 relative to AA induction) with 100 µg of Hu3 or Mt3 in 100 µl of IFA and AA was induced on day 0. Splenocytes were collected on day 26 after induction of AA, activated for 48 hr with Con A and transferred iv to naïve rats. Three days later, AA was induced in the recipients and arthritis scores were assessed. B. Leg swelling measured on day 26 after AA induction.

To learn whether the protection triggered by Hu3-vaccination could be adoptively transferred by activated T-cells, splenocytes prepared from Hu3 vaccinated rats were stimulated in vitro for 2 days with the T-cell mitogen Con A, washed, and injected iv ($5 \times 10^7$ cells per rat) into naïve rats. Only the recipients of cells taken from Hu3-vaccinated rats were protected against the subsequent induction of AA (FIGS. 4A and 4B). No protection was seen in rats that had received Con A activated cells from Mt3 injected rats. Thus, inhibition of AA by vaccination with Hu3 could be adoptively transferred by activated T-cells.

Figure 5:
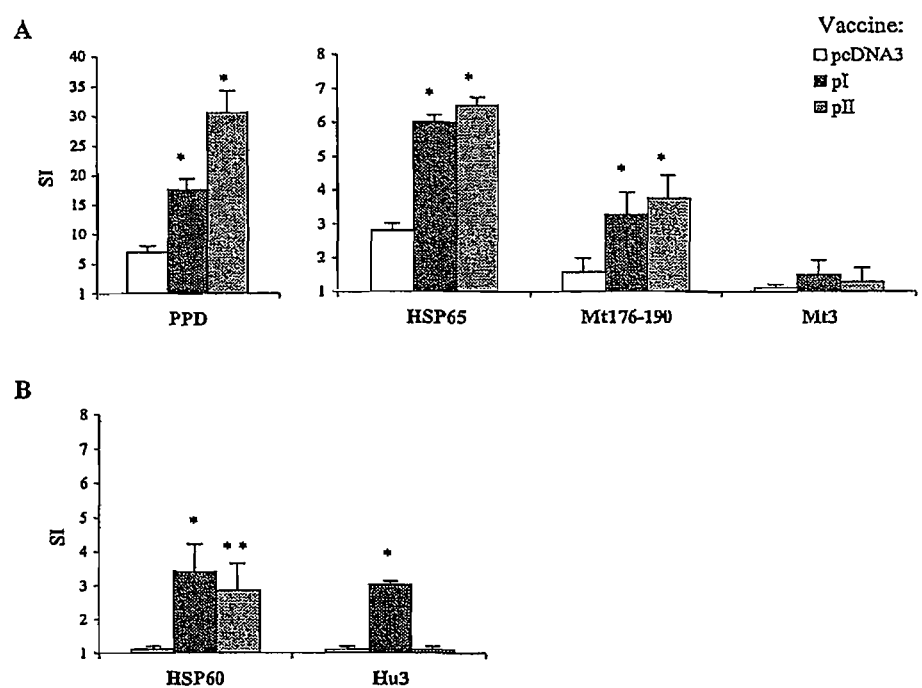
FIG. 5: T-cell responses after DNA vaccination. Lewis rats were vaccinated with pI, pII or pcDNA3 and AA was induced. Twenty-six days later, LNC were collected, and the proliferative responses to (A) PPD, (B) HSP65, Mt176-190, Mt3, HSP60 and Hu3 were studied.

Example 5: In Vitro Proliferation of LNC Isolated from PI- or PII-Vaccinated Rats in Response to Various Mycobacterial Antigens, HSP60 or its Hu3 Peptide To study the mechanism associated with the inhibition of AA by DNA vaccination with pI or pII, the T-cell responses of immunized rats was analysed 26 days after the induction of AA. The LNC were stimulated in vitro with a collective of mycobacterial antigens known to be associated with AA: HSP65, PPD, Mt176-90 (which contains the 180-188 epitope of HSP65). The immune response directed to mammalian HSP60, its regulatory peptide Hu3 and the HSP60-derived peptide Hu12 as a control was studied as well. OVA was included as a control antigen. None of the experimental groups showed significant responses to OVA or Hu12, and they did not differ in their response to Con A (data not shown). Nevertheless, inhibition of AA by DNA vaccination with the pI or pII constructs was associated with the up-regulation of the T-cell proliferative responses directed against the panel of mycobacterial antigens (PPD, HSP65 and Mt176-190) (FIG. 5A). FIG. 5B depicts the proliferative responses to HSP60 and its Hu3 peptide. It can be seen that both pI and pII induced significant T-cell responses to HSP60, however, only LNC from pI-vaccinated rats manifested reactivity to Hu3.

Example 6: Cytokine Secretion by LNC Taken from Rats Vaccinated with pI, pII or pcDNA3

Cytokine secretion by LNC taken from rats vaccinated with pI, pII or pcDNA3 was determined. Inhibition of AA by DNA vaccination with pI was associated with a decrease in IFNγ secretion (FIG. 6A), and an increase in IL-10 and TGFβ1 secretion upon stimulation with PPD, HSP65 or Mt176-190 (FIGS. 6B and 6C).

Figure 6:
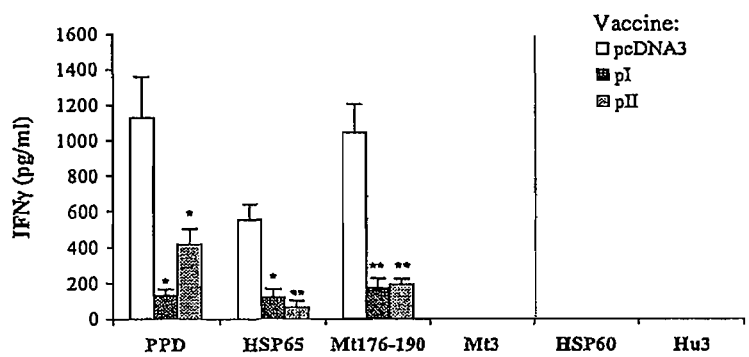
FIG. 6: Cytokine secretion after DNA vaccination. Lewis rats were vaccinated with pI, pII or pcDNA3 and AA was induced. Twenty-six days later, LNC were collected, stimulated in vitro with PPD, (B) HSP65, Mt176-190, Mt3, HSP60 and Hu3 and the supernatants were tested after 72 hr for the amounts of secreted (A) INFγ, (B) IL-10 or (C) TGFβ1.
Figure 6:
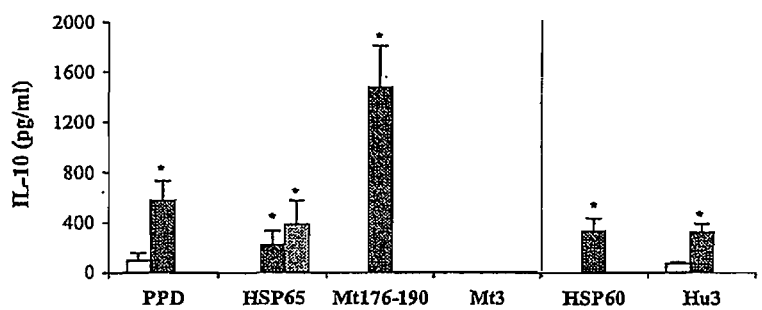
Figure 6:
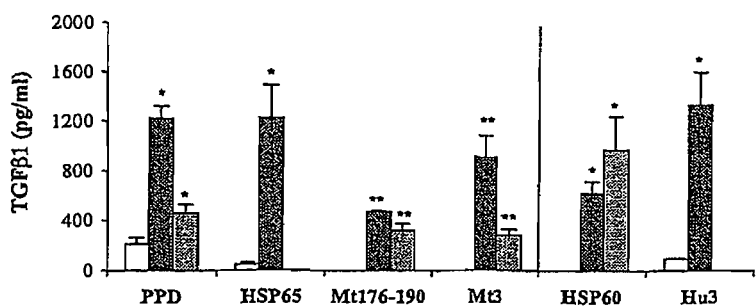

LNC from pII-vaccinated rats also showed a decrease in IFNγ secretion upon stimulation with PPD, HSP65 and Mt176-190 (FIG. 6A), however IL-10 secretion was only detected after activation with HSP65 while TGFβ1 secretion was only detected following activation with Mt176-190 or PPD (FIGS. 6B and 6C). Note that cells from both pI or pII-immunized rats secreted detectable amounts of TGFβ1 upon activation with Mt3. Thus, protection from AA by DNA vaccination with pI or pII was associated with decreased IFNγ secretion and a concomitant increase in IL-10 and/or TGFβ1 secretion upon stimulation with the mycobacterial antigens PPD, HSP65 or Mt176-190 (FIGS. 6A, 6B and 6C).

In addition to the responses to mycobacterial antigens, the effects of DNA vaccination with HSP60 fragments on the responses to HSP60 and Hu3 was studied. IFNγ was not secreted in response to HSP60 or Hu3 by the LNC of either the pI or pII-immunized rats (FIG. 6A). LNC taken from pI immunized rats secreted both IL-10 and TGFβ1 in response to HSP60 or Hu3 (FIGS. 6B and 6C). LNC cells taken from pII-vaccinated rats, in contrast, secreted TGFβ1 upon activation with HSP60, but IL-10 was not detected. Therefore, both pI or pII vaccination induced the secretion of TGFβ1 in response to HSP60. However only pI triggered the secretion of IL-10.

Example 7: In Vitro Proliferation of LNC Isolated from Hu3-Vaccinated Rats in Response to Various Mycobacterial Antigens or HSP60

Figure 7:
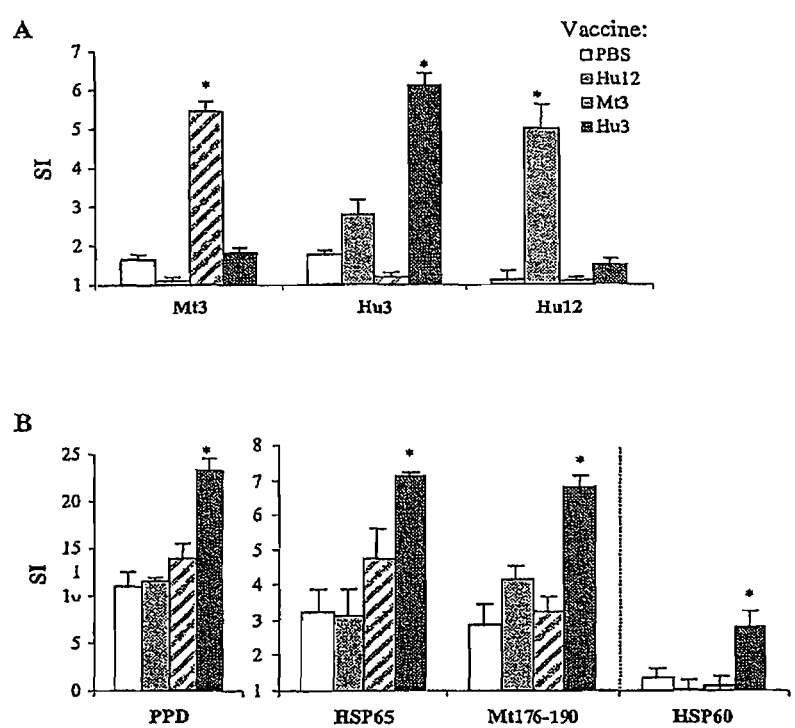
FIG. 7: T-cell responses after DNA vaccination. Lewis rats were vaccinated with Hu3, Mt3, Hu12 or PBS and AA was induced. Twenty-six days later, LNC were collected, and the proliferative responses to (A) PPD, (B) HSP65, Mt176-190, Mt3, HSP60 and Hu3 were studied.

The T-cell responses after induction of AA in rats that had been vaccinated with peptides Hu3, Hu12 or Mt3 was examined. All three peptides were immunogenic; significant and specific T-cell responses could be detected in the immunized rats to each immunogen (FIG. 7A). However, only the LNC taken from Hu3-vaccinated rats showed up-regulated T-cell proliferative responses to the mycobacterial antigens PPD, HSP65 and Mt176-190 (FIG. 7B). Furthermore, vaccination with Hu3 led to the induction of a specific response to HSP60 (FIG. 7B). None of the experimental groups showed significant responses to OVA, and they did not differ in their response to Con A (data not shown).

Example 8: Cytokine Secretion by LNC Taken from Rats Vaccinated with Hu3

Figure 8:
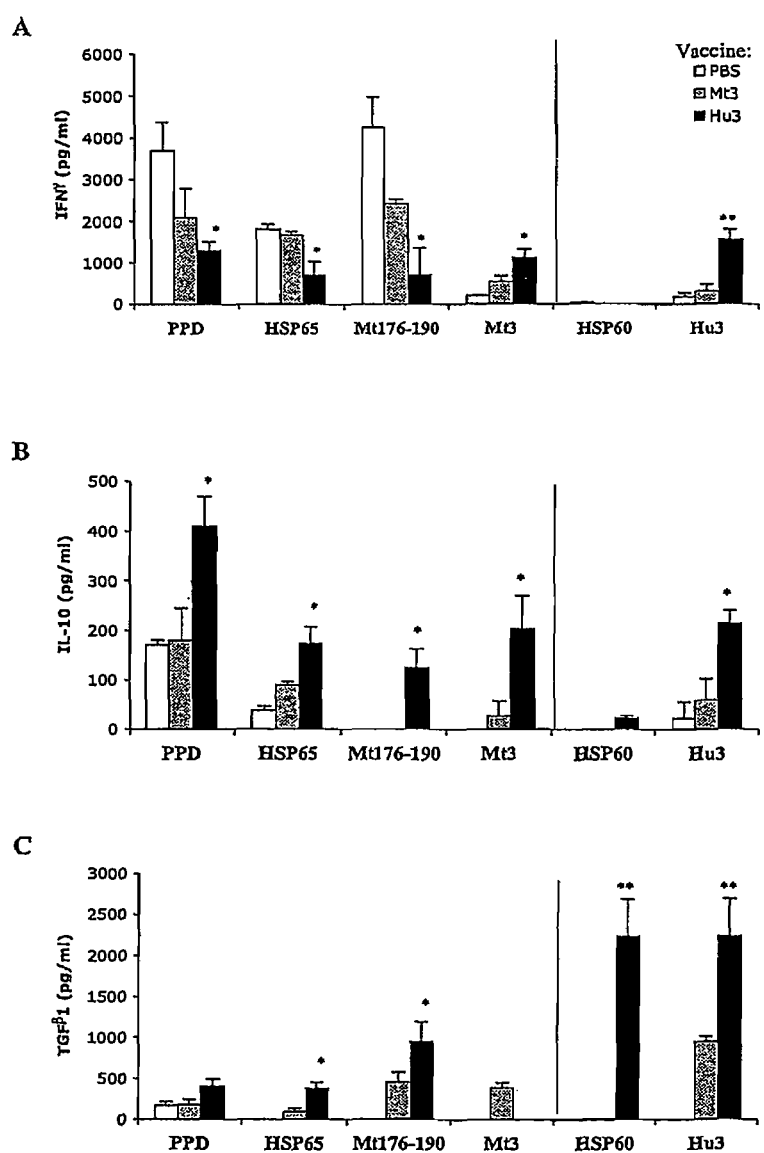
FIG. 8: Cytokine secretion after DNA vaccination. Lewis rats were vaccinated with Hu3, Mt3, Hu12 or PBS, and AA was induced. Twenty-six days later, LNC were collected, stimulated in vitro with PPD, (B) HSP65, Mt176-190, Mt3, HSP60 and Hu3 and the supernatants were tested after 72 hr for the amounts of secreted (A) INFγ, (B) IL-10 or (C) TGFβ1.

Vaccination with Hu3 led to a reduction in IFNγ secretion (FIG. 8A), and to a concomitant increase in the secretion of IL-10 (FIG. 8B) and TGFβ1 (FIG. 8C) upon stimulation with PPD, HSP65 or Mt176-190. Hu3-vaccination also led to the induction of T-cells that secreted IFNγ, IL-10 and TGFβ1 in response to Hu3. The response to whole HSP60 was predominantly TGFβ1.

Figure 9:
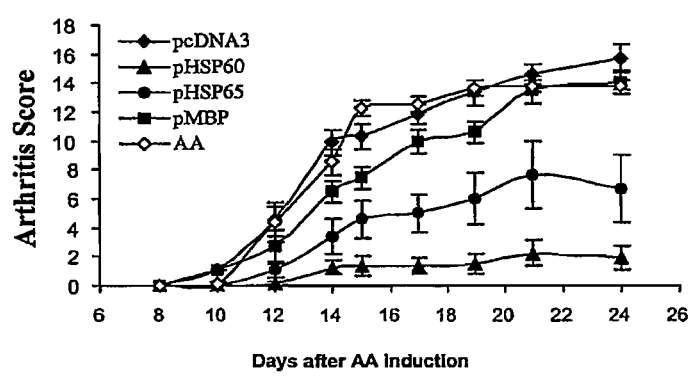
FIG. 9: Modulation of AA by preimmunization with pHSP60 or pHSP65. A. Time course of AA. Rats were vaccinated in the quadriceps three times (on days −40, −26 −12 relative to AA induction) with 150 μg of pcDNA3, pMBP, pHSP60 or pHSP65, or left untreated as controls (AA). On day 0 AA was induced by injecting 1 mg of *Mycobacterium tuberculosis* (Mt) suspended in 100 μl of IFA, and arthritis scores were assessed every two or three days starting at day 8 after Mt injection. B. Leg swelling measured at day 26 after AA induction.
Figure 9:
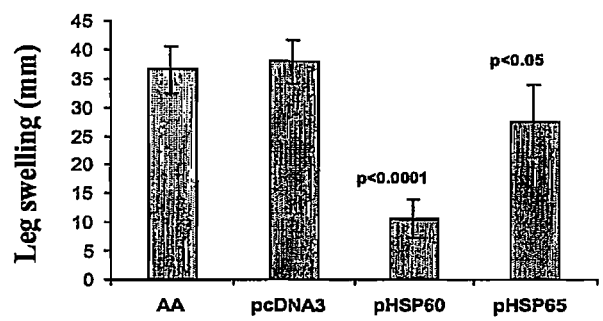

Example 9: Human pHPS60 is More Effective than Mycobacterial pHSP65 in Inhibiting AA The effects on AA of vaccination with DNA encoding human pHSP60 compared to mycobacterial HSP65 was examined. The construct encoding the full-length human HSP60 (pHSP60) has more than 97% percent identity at the amino acid level with its rat counterpart. A construct encoding for the full-length HSP65 of *Mycobacterium* was used as well. Two control constructs were used: an empty vector (pcDNA3), and a construct encoding murine Myelin Basic Protein (pMBP). FIG. 9a shows that vaccination with pcDNA3 or pMBP did not have any effect on AA. In contrast, rats immunized with pHSP60 or pHSP65 manifested a significantly milder arthritis. Inhibition of AA was also reflected as a diminished swelling of the ankle, as shown in FIG. 9b. It can be seen that pHSP60 was more effective than pHSP65 in modulating the autoimmune process. The difference between pHSP60 and pHSP65 was statistically significant with regard to the maximal AA index (2.25±0.65 vs. 7.67±1.83, p=0.02), and leg swelling (10.64±3.43 vs. 27.5±6.35, p=0.03).

Example 10: In Vitro Proliferation of LNC Isolated from Rats After DNA Vaccination with pHSP60

Figure 10:
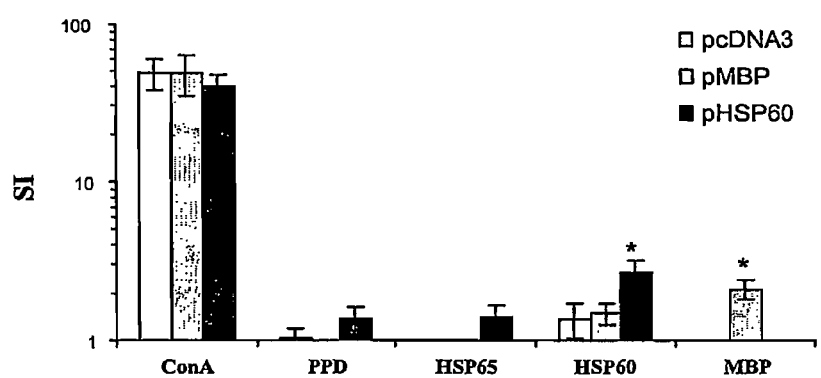
FIG. 10: Proliferative responses to HSP60, HSP65 and PPD in pHSP60-, pMBP and pcDNA3-vaccinated animals. Female Lewis rats were vaccinated in the quadriceps three times (on days −40, −26 −12 relative to AA induction) with 150 μg of pHSP60, pMBP or pcDNA3, beginning 5 days after i.m. injection of 200 μl of cardiotoxin 10 μM. A group was left untreated as a control. Animals were killed and LNC were collected on day −1 prior to the induction of AA.

The immune response induced by pHSP60-vaccination alone was studied before disease induction. Spleen cells were prepared 10 days after the administration of the third dose of the DNA-vaccine, and the proliferative response upon in vitro stimulation with different antigens was studied. FIG. 10 shows that pHSP60-vaccination induced a significant proliferative response to HSP60, but not to HSP65, MBP or PPD, while cells from pMBP-treated rats only proliferated in response to MBP. These HSP60-specific T-cells secreted low amounts of both IL-10 (22±5 pg/ml) and IFNγ (80±15 pg/ml) upon stimulation in vitro with HSP60 (data not shown). No cytokine release was detected when splenocytes from pcDNA3-treated animals were stimulated with HSP60. No significant differences were seen between the different experimental groups neither in T-cell proliferation nor in cytokine-release in response to stimulation with Con A (data not shown). Thus pHSP60 vaccination induced a low, but specific T-cell response to HSP60; the immune response elicited by pHsp60 vaccination is capable of affecting the immune reactions that characterize AA.

Figure 11:
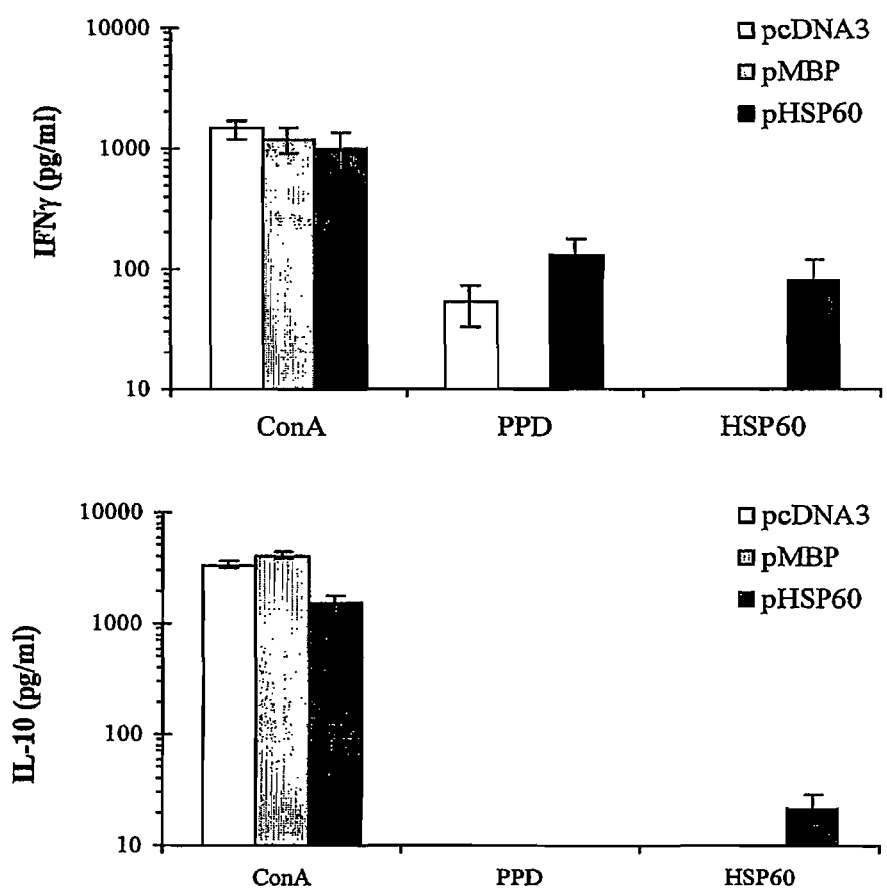
FIG. 11: T-cell responses in AA rats vaccinated with pcDNA3. Animals vaccinated with pcDNA3 were killed on day 26 after induction of AA and their LNC were collected and stimulated in vitro for 72 hrs in the presence of different concentrations of antigen. The release of IFNγ and IL-10 was studied.

Example 11: Cytokine Secretion in AA Rats Vaccinated with pHSP60 pHSP65 or Hu3/IFA Twenty-six days after the induction of AA, LNC were prepared from untreated rats, or animals that had been treated with pcDNA3 or PBS/IFA. LNC were stimulated in vitro with a collective of antigens previously known to be targeted or associated with AA: HSP60, HSP65, PPD, P176-90 (which contains the 180-188 epitope of HSP65 (3)) and Hu3 described here. Hu12 and OVA were included as control antigens. The results were essentially the same whether the AA was induced in untreated rats, or in rats pre-treated with injections of PBS/IFA or pcDNA3. FIG. 11 depicts the results obtained with LNC isolated from pcDNA3-treated animals, showing the cytokines released to the culture medium. LNC from pCDNA3-treated animals showed a strong proliferative response to PPD, and low but significant responses to HSP65 and P176-90, while no proliferation was detected after stimulation with HSP60, Hu3 or Hu12. Although the proliferative response to P176-90 was quite low, stimulation with this peptide led to the release of IFNγ to at least the same levels as those achieved by stimulation with PPD. IFNγ was secreted to a lower extent in response to HSP65, while no secretion was detected upon stimulation with HSP60, Hu3 or Hu12. IL-10 and TGFβ1 were detected only upon activation with PPD. Thus, induction of AA activates T-cells that almost exclusively secrete IFNγ in response to activation with mycobacterial antigens, and that do not appear to recognize HSP60 or its peptides Hu3 and Hu12.

Figure 12:
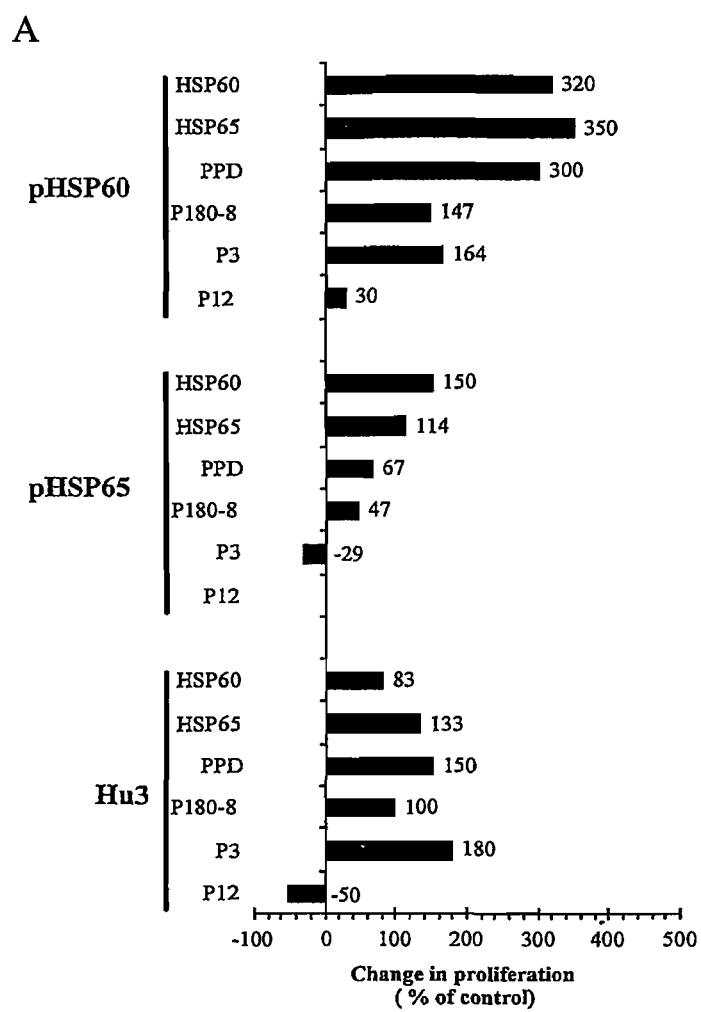
FIG. 12: Effect of vaccination on cytokine secretion. Animals vaccinated with pHSP60, pHSP65 or Hu3 were killed on day 26 after induction of AA and their LNC were collected. The cells were stimulated for 72 hrs in the presence of different antigens, and the proliferation (a) or the release of IFNγ (b), IL-10 (c) and TGFβ$_1$ (d) were studied and are illustrated.
Figure 12:
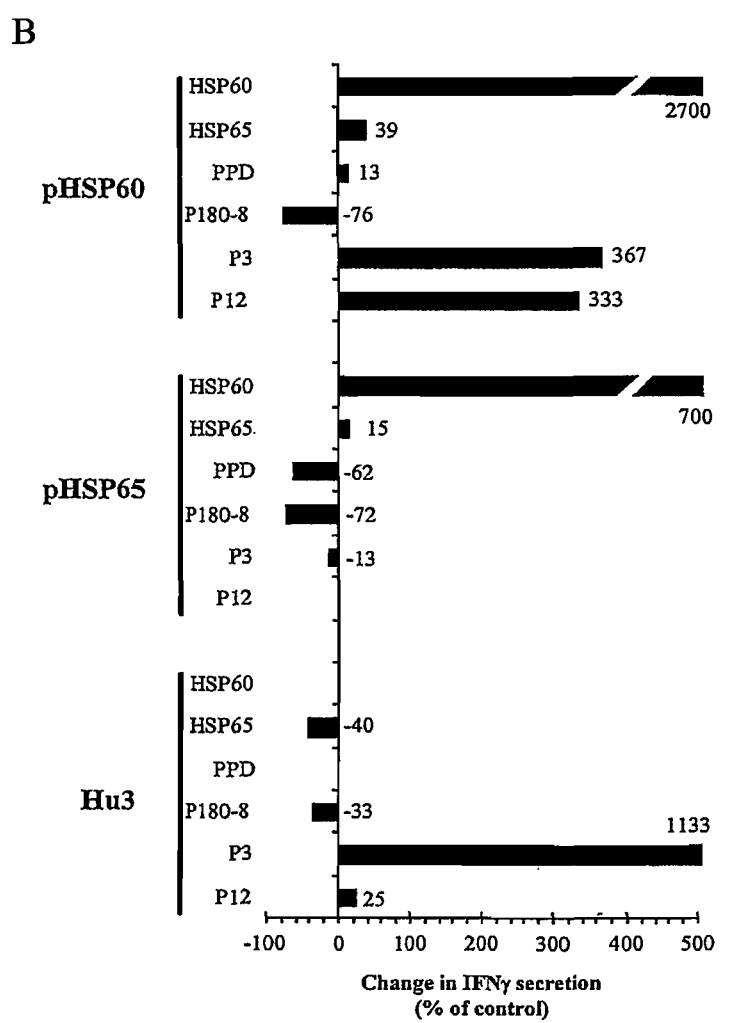
Figure 12:
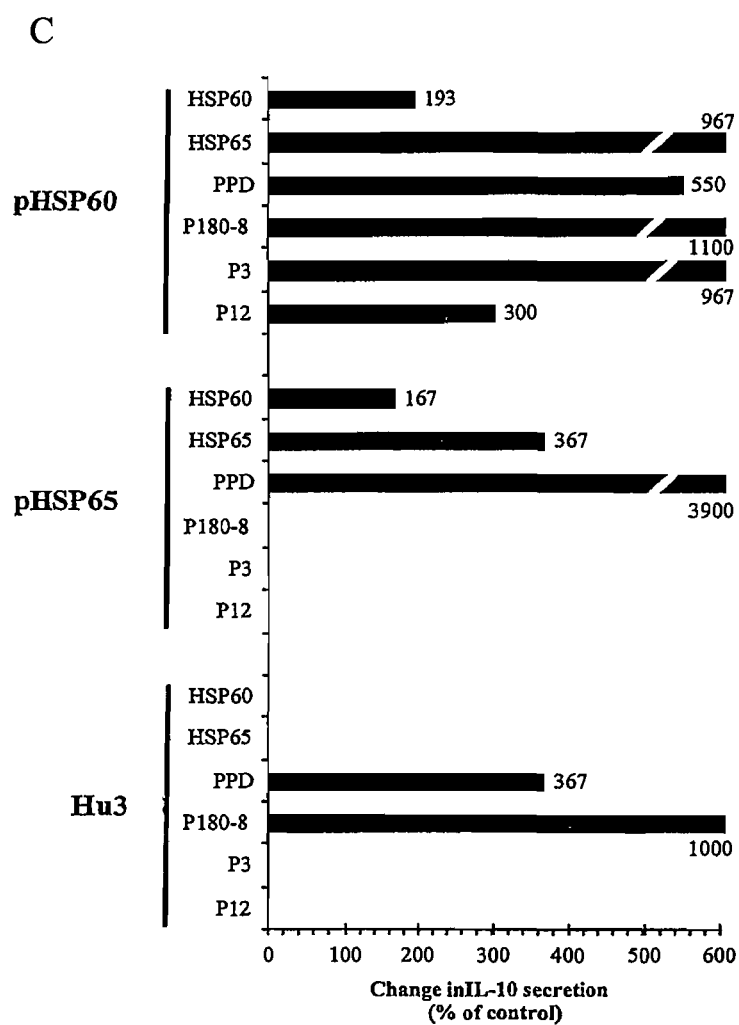
Figure 12:
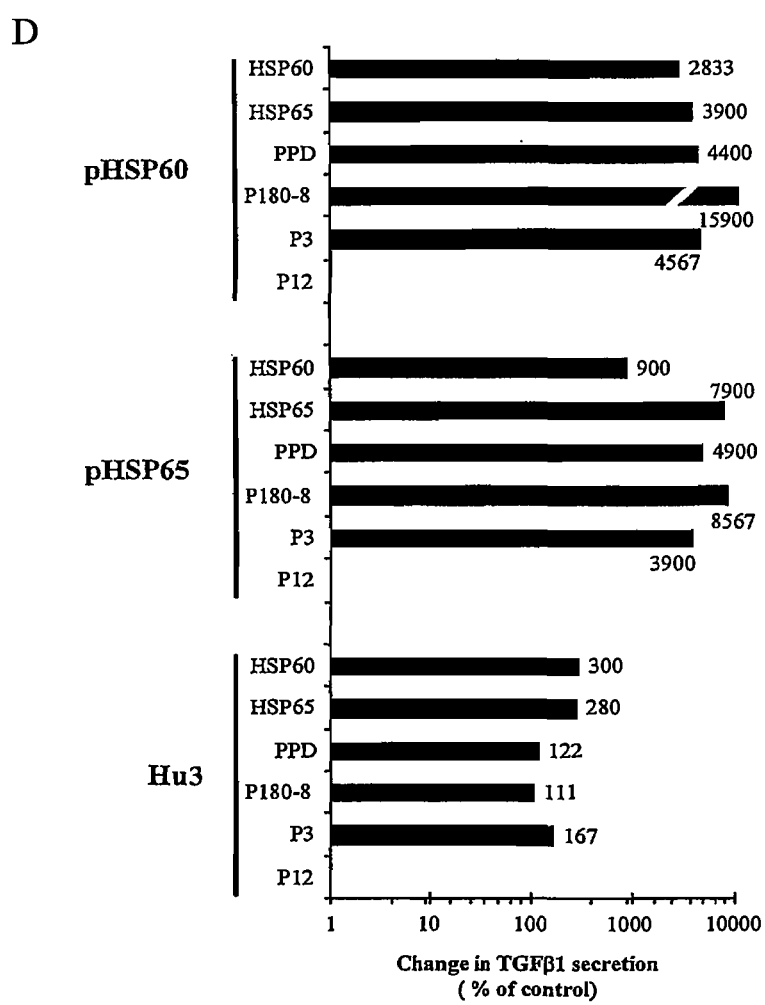

FIG. 12A depicts the proliferative response and cytokine secretion of cells isolated from animals treated with pHSP60, pHSP65 or Hu3/IFA expressed as the percent change in reactivity relative to the proliferation seen using cells from their respective controls (pcDNA3 or PBS/IFA-treated animals). Animals protected from AA showed increased proliferative responses to mycobacterial antigens (PPD, HSP65 and P176-90). The increase in the proliferation to HSP65 and PPD was stronger in pHSP60-treated animals. Also the response to mammalian HSP60 was up-regulated throughout all the groups, but this effect was more marked in pHSP60 vaccinated animals. Moreover, at day 26 after AA induction, the response to HSP60 was significantly higher than that detected at the end of the immunization protocol (Stimulation Index, SI=2.4±0.39 vs. SI=4.44±0.37 respectively, p<0.05). In addition, Hu3 was only recognized by animals immunized with pHSP60, or with Hu3 itself, while there were no responses directed towards Hu12. Cells from HU12/IFA-treated rats proliferated upon stimulation with HU12 (data not shown). None of the experimental groups showed significant responses to OVA, and they did not differ in their response to Con A (data not shown). Thus, modulation of AA by vaccination with pHSP60, pHSP65 or Hu3 is accompanied by the up-regulation of T-cell proliferative responses to both self- and mycobacterial antigens. The phenotype of these augmented cellular responses has been characterized in terms of cytokine release profiles.

As shown in FIG. 12B, Secretion of IFNγ was increased in LNC from: A, pHSP60-treated rats stimulated with HSP60, Hu3 or Hu12; B, pHSP65-treated rats stimulated with HSP60 and C, in Hu3-treated rats stimulated with Hu3. Thus, modulation of AA is associated with a reduction in IFNγ release to P176-90 and an increase in the release of IFNγ to HSP60. As shown in FIG. 12C, the study of IL-10 secretion revealed that LNC from animals protected from AA (either by DNA or peptide vaccination) showed increased secretion of IL-10 in response to in vitro stimulation with mycobacterial antigens. In cells from all the groups protected we found secretion of IL-10 in response to stimulation with PPD, HSP65 (pHSP60 and pHSP65-treated animals) or P176-90 (pHSP60- and Hu3-treated rats). Release of IL-10 upon stimulation with HSP60 and its peptides was not uniform and only found in cells from pHSP60 or pHSP65-vaccinated animals. Therefore protection was associated with the induction of IL-10 secretors responsive to mycobacterial antigens (PPD or P180-90) and, in DNA vaccinated animals, to mammalian HSP60. The analysis of TGFβ1 release from LNC taken from all the groups protected from AA, (either by DNA or peptide vaccination), showed an increase in the secretion of TGFβ1 in response to stimulation with mycobacterial antigens and HSP60 or its peptides (FIG. 12D). However, this effect was stronger in DNA-treated rats.

All together, the results suggest that modulation of AA by treatment with specific DNA or peptide is associated with three observations. A, decreased secretion of IFNγ upon stimulation with the HSP65 peptide P178-190. B, the induction HSP60-specific T-cells that secrete IFNγ. C, the appearance of IL-10 and TGFβ1 secretors specific for mycobacterial antigens and HSP60.

Example 12: Inhibition of AA by DNA Vaccines Encoding Human HSP70 and Human HSP90

Figure 13:
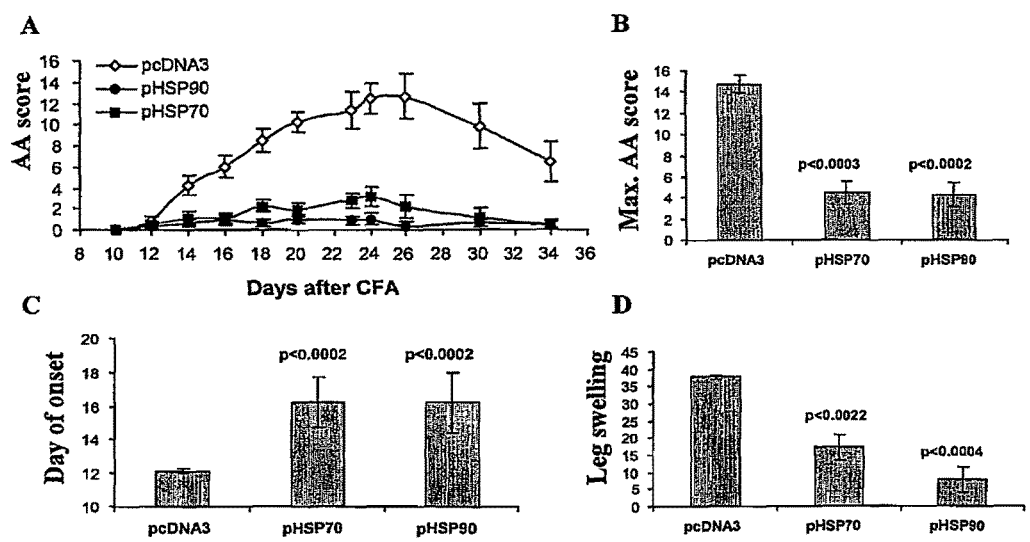
FIG. 13: Inhibition of AA by preimmunization with pHSP70 or pHSP90. A. Time course of AA. B. Maximal arthritis score. C. Day of onset. D. Difference in leg swelling measured at day 26 after AA induction.

The full-length cDNA of human HSP70 (pHSP70) or human HSP90 (pHSP90) were cloned into the pcDNA3 vector. The gene constructs were found to be functional in an in vitro transcription/translation system (data not shown). Rats were immunized with pHSP90 and pHSP70 following the same scheme of vaccination used for pHSP60, and 12 days after the last injection of DNA, AA was induced. FIG. 13A shows that in rats vaccinated with pHSP70 or pHSP90 there was a significant inhibition of AA Inhibition of AA was also seen as a reduction in the maximal score (FIG. 13B), leg swelling (FIG. 13C) and a significant delay in the mean day of disease onset (FIG. 13D).

Figure 14:
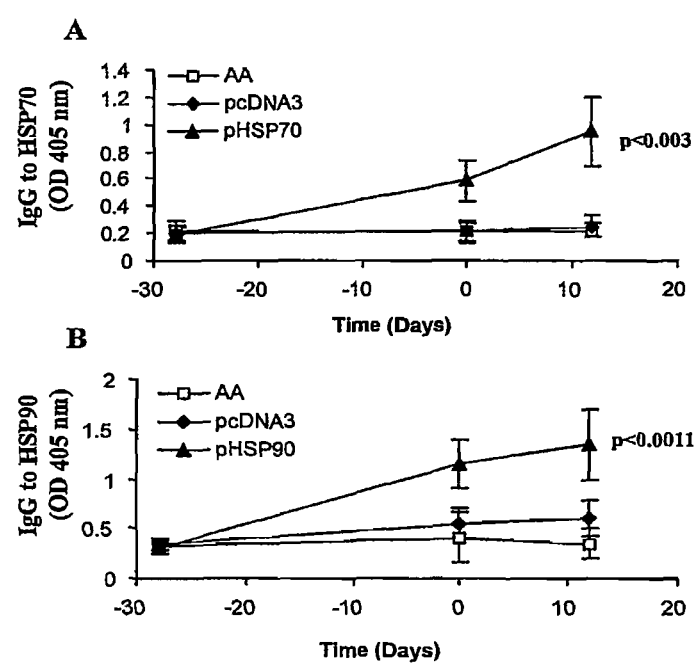
FIG. 14. Humoral response in DNA vaccinated rats. A. Antibodies to HSP70 in pHSP70-immunized rats. B. Antibodies to HSP90 in pHSP90-immunized rats. The day of induction of AA was considered day 0.

In order to gain some insight into the mechanism that mediates prevention of AA by treatment with pHSP70 or pHSP90, the induction of antibodies of the IgG isotype to the antigen encoded by the vector was studied. FIGS. 14A and 14B depict the results obtained for pHSP70- and pHSP90-treated rats respectively. Vaccination with the DNA constructs induced specific antibodies, indicating that both constructs are immunogenic; and the humoral response induced is up-regulated upon induction of AA.

Example 13: Cytokine Secretion and In Vitro Proliferation of LNC Isolated from AA Rats Vaccinated with pHSP70 or pHSP90

Figure 15:
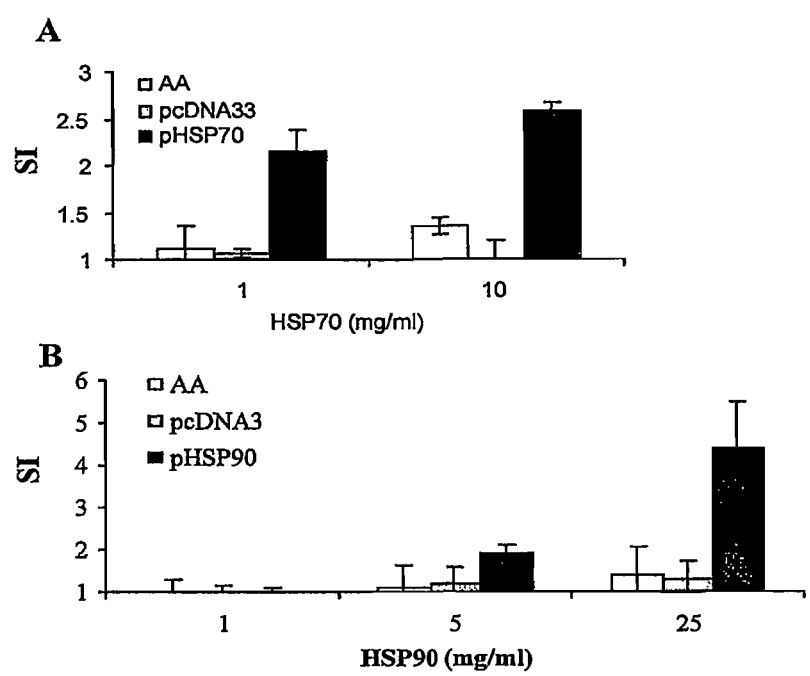
FIG. 15. T-cell response to the immunizing antigen in DNA-vaccinated rats. A. Proliferative response to HSP70 in pHSP70-immunized rats. The results are presented as the mean±SD of the stimulation index (SI) in quadruplicate cultures. B. Proliferative response to HSP90 in pHSP90-immunized rats. The results are presented as the mean±SD of the SI in quadruplicate cultures.
Figure 16:
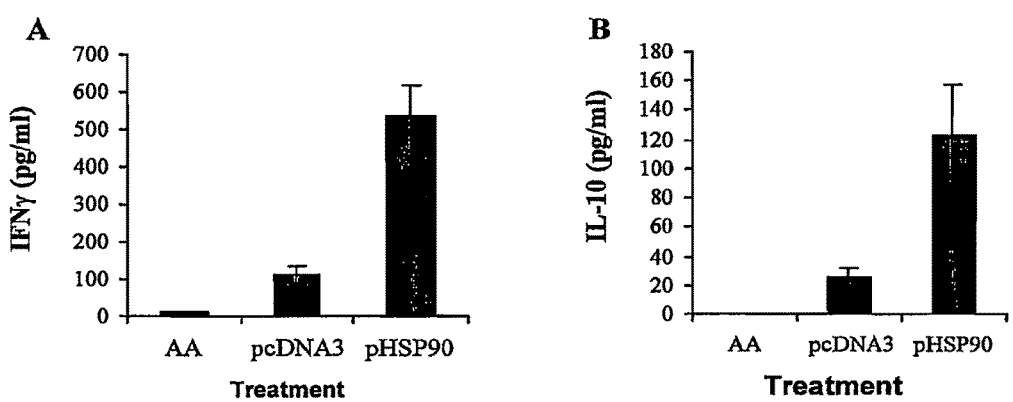
FIG. 16. Cytokine secretion in response to stimulation with the immunizing antigen in DNA-vaccinated rats. Draining lymph node cells were stimulated for 72 hrs in the presence of HSP70 or HSP90, and the content of IFNγ (A) or IL-10 (B) was determined in the supernatants by capture ELISA.

FIGS. 15A and 15B shows that draining lymph node DLN cells from immunized animals showed a dose response proliferation upon activation with the protein encoded by the immunizing vector. Furthermore, the analysis of the cytokines released in response to antigen-specific stimulation revealed that cells taken from pHSP90-immunized animals secreted both IL-10 and IFNγ in response to activation with HSP90 (FIGS. 16A and 16B). There was no IFNγ or IL-10 secretion when cells from pHSP70-treated animals were stimulated with HSP70 (data not shown).

Figure 17:
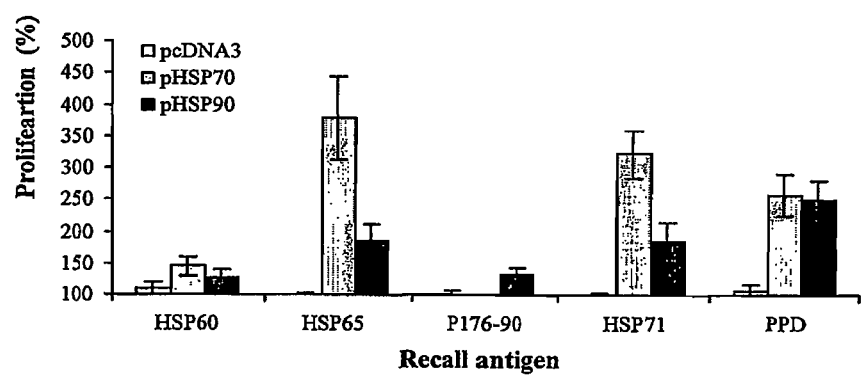
FIG. 17: Effect of DNA vaccination on T-cell proliferation following AA induction. The results are expressed as the percent change in proliferation relative to the responses of untreated rats, 26 after the induction of AA.
Figure 18:
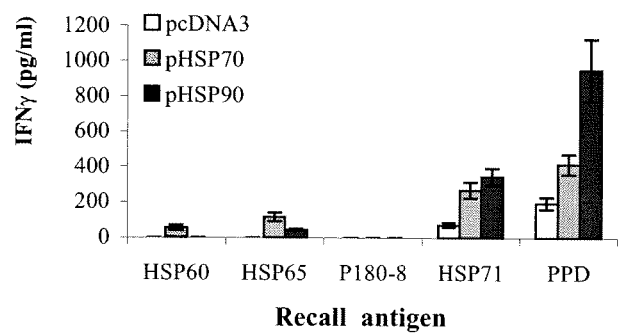
FIG. 18: Effect of DNA vaccination on cytokine secretion following AA induction. DLN cells were stimulated for 72 hrs in the presence of HSP70 or HSP90, and the content of IFNγ (A), IL-10 (B) or TGFβ1 (C) was determined in the supernatants by capture ELISA.
Figure 18:
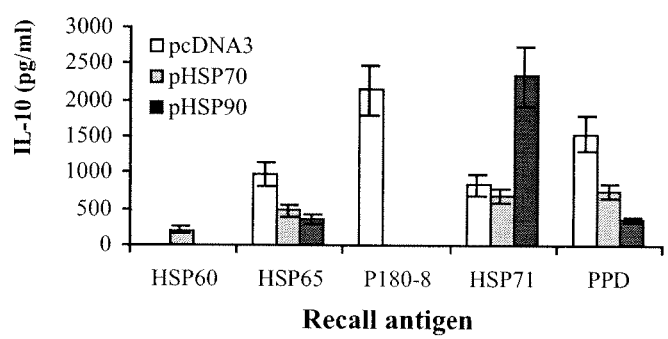
Figure 18:
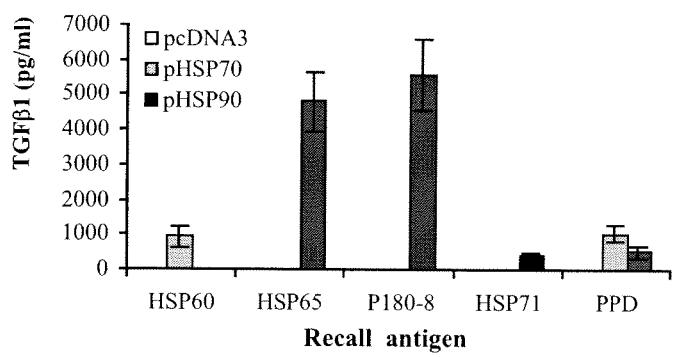

The immune response to a panel of antigens in DLN cells isolated from pcDNA3-, pHSP70- or pHSP90-treated rats was detected 26 days after the induction of AA. The results are shown in FIG. 17 as the percentage of the proliferation observed in untreated rats. Vaccination with pHSP70 or pHSP90 led to a significant up-regulation in the proliferative response to HSP65, HSP71 and PPD, and this increase in the immune response was stronger in pHSP70 vaccinated rats. To further characterize the nature of the up-regulated immune response in pHSP70- and pHSP90-vaccinated, cytokine secretion in response to in vitro stimulation with the same AA-related antigens was detected. IFNγ secretion in response to stimulation with HSP65, its epitope P176-188 or PPD was down-regulated in animals treated with pHSP70 or pHSP90 (FIG. 18A). In addition, IL-10 secretion was up-regulated upon in vitro activation with PPD, HSP71, HSP65 or HSP60, both in pHSP70- and pHSP90-vaccinated animals (FIG. 18B). Finally, TGFβ1 release upon stimulation with HSP65 and its peptide P176-80 was increased in cells taken from pHSP90-vaccinated animals, and there was a slight but significant release of in response to stimulation with PPD in cells from pHSP70-treated animals (FIG. 18C). Note that the decrease in IFNγ secretion and the concomitant increase in IL-10 and TGFβ1 release was stronger in the group treated with pHSP90; in this group AA was inhibited even more effectively than in pHSP70-immunized rats.

TABLE I

Overlapping peptides of human HSP60, region 1-275

| Peptide | Position | | Sequence |
|---|---|---|---|
| Hu1 | 1-20 | (SEQ ID NO: 15) | MLRLPTVFRQMRPVSRVLAP |
| Hu2 | 16-35 | (SEQ ID NO: 16) | RVLAPHLTRAYAKDVKFGAD |
| Hu3 | 31-50 | (SEQ ID NO: 3) | KFGADARALMLQGVDLLADA |
| Hu4 | 46-65 | (SEQ ID NO: 17) | LLADAVAVTMGKGRTVIIE |
| Hu5 | 61-80 | (SEQ ID NO: 18) | TVIIEQSWGSPKVTKDGVTV |
| Hu6 | 76-95 | (SEQ ID NO: 19) | DGVTVAKSIDLKDKYKNIGA |
| Hu7 | 91-110 | (SEQ ID NO: 20) | KNIGAKLVQDVANNTNEEAG |
| Hu8 | 106-125 | (SEQ ID NO: 21) | NEEAGKGTTTATVLARSIAK |
| Hu9 | 121-140 | (SEQ ID NO: 22) | RSIAKEGFEKISKGANPVEI |
| Hu10 | 136-155 | (SEQ ID NO: 23) | NPVEIRRGVMLAVDAVIAEL |
| Hu11 | 151-170 | (SEQ ID NO: 24) | VIAELKKQSKPVTTPEEIAQ |
| Hu12 | 166-185 | (SEQ ID NO: 25) | EEIAQVATISANGDKEIGNI |
| Hu13 | 181-199 | (SEQ ID NO: 26) | EIGNIISDAMKKVGRKGVI |
| Hu14 | 195-214 | (SEQ ID NO: 27) | RKGVITVKDGKTLNDELEII |
| Hu15 | 210-229 | (SEQ ID NO: 28) | ELEIIEGMKFDRGYISPYFI |
| Hu16 | 225-244 | (SEQ ID NO: 29) | SPYFINTSKGQKCEFQDAYV |
| Hu17 | 240-259 | (SEQ ID NO: 30) | QDAYVLLSEKKISSIQSIVP |
| Hu18 | 255-275 | (SEQ ID NO: 31) | QSIVPALEIANAHRKPLVIIA |

TABLE II

Plasmids constructed containing overlapping fragments of the hsp60 gene

| Plasmid | Position | Corresponding Peptides included |
|---|---|---|
| pI | 1-140 | Hu1-Hu9 (a.k.a. P1-P9; SEQ ID NO: 1) |
| pII | 130-260 | Hu10-Hu18 (a.k.a. P10-P18; SEQ ID NO: 2) |
| pIII | 250-410 | NS |
| pIV | 400-470 | NS |
| pIV | 460-540 | NS |

The position is expressed as amino acid residue numbers.
NS = Not synthesized as individual peptides.

TABLE III

Comparison of human HSP60, rat HSP60 and mycobacterial HSP65 in the region corresponding to the Hu3 sequence[a,b].

| | | | | |
|---|---|---|---|---|
| H. sapiens | 31 | KFGADARALMLQGVDLLADA | 50 | (SEQ ID NO: 3) |
| R. norvergicus | 31 | KFGADARALMLQGVDLLADA | 50 | (SEQ ID NO: 35) |
| M. tuberculosis | 5 | A_YDEE_ARRG_LERGLNA_LADA | 24 | (SEQ ID NO: 32) |

[a]H. sapiens, Homo sapiens; R. norvergicus, Rattus norvergicus; M. tuberculosis, Mycobacterium tuberculosis.
[b]Residues sharing identity with the corresponding sequence of human HSP60 are shown in bold, and conserved substitutions are shown as underlined residues.

Peptides were synthesized as previously described (15). The HSP60 peptides used in these studies are listed in Table I. Two HSP65 peptides were also used: Mt176-190, EESNTFGLQLELTEG (SEQ ID NO:33) (16) and Mt3, AYDEEARRGLERGLNALADA (SEQ ID NO:34). Purified recombinant HSP65 was generously provided by Prof. Ruurd van der Zee (Institute of Infectious Diseases and Immunology, Faculty of Veterinary Medicine, Utrecht, The Netherlands). Recombinant HSP60 was prepared in our laboratory as described (11). *M. tuberculosis* Strain H37Ra and incomplete Freund's adjuvant (IFA) were purchased from Difco (Detroit, Mich., USA). Tuberculin purified protein derivative (PPD) was provided by the Statens Seruminstitut (Copenhagen, Denmark). Ovalbumin (OVA) and Concanavalin A (Con A) were purchased from Sigma (Rehovot, Israel).

REFERENCES

1. Wauben, M. H. M., J. P. A. Wagenaar-Hilbers, and W. van Eden. 1994. Adjuvant Arthritis. In *Autoimmune Disease Models*. I. R. Cohen, and A. Miller, eds. Academic Press, Inc., Calif., USA.
2. van Eden, W., J. E. Thole, R. van der Zee, A. Noordzij, J. D. van Embden, E. J. Hensen, and I. R. Cohen. 1988. Cloning of the mycobacterial epitope recognized by T lymphocytes in adjuvant arthritis. *Nature* 331:171.
3. van Eden, W., J. Holoshitz, Z. Nevo, A. Frenkel, A. Klajman, and I. R. Cohen. 1985. Arthritis induced by a T-lymphocyte clone that responds to *Mycobacterium tuberculosis* and to cartilage proteoglycans. *Proc Natl Acad Sci USA* 82:5117.
4. Holoshitz, J., A. Matitiau, and I. R. Cohen. 1984. Arthritis induced in rats by cloned T lymphocytes responsive to mycobacteria but not to collagen type II. *J Clin Invest* 73:211.
5. Holoshitz, J., Y. Naparstek, A. Ben-Nun, and I. R. Cohen. 1983. Lines of T lymphocytes induce or vaccinate against autoimmune arthritis. *Science* 219:56.
6. Billingham, M. E., S. Carney, R. Butler, and M. J. Colston. 1990. A mycobacterial 65-kD heat shock protein induces antigen-specific suppression of adjuvant arthritis, but is not itself arthritogenic. *J Exp Med* 171:339.
7. Hogervorst, E. J., L. Schouls, J. P. Wagenaar, C. J. Boog, W. J. Spaan, J. D. van Embden, and W. van Eden. 1991. Modulation of experimental autoimmunity: treatment of adjuvant arthritis by immunization with a recombinant vaccinia virus. *Infect Immun* 59:2029.
8. Ragno, S., M. J. Colston, D. B. Lowrie, V. R. Winrow, D. R. Blake, and R. Tascon. 1997. Protection of rats from adjuvant arthritis by immunization with naked DNA encoding for mycobacterial heat shock protein 65. *Arthritis Rheum* 40:277.

9. Moudgil, K. D., T. T. Chang, H. Eradat, A. M. Chen, R. S. Gupta, E. Brahn, and E. E. Sercarz. 1997. Diversification of T cell responses to carboxy-terminal determinants within the 65-kD heat-shock protein is involved in regulation of autoimmune arthritis. *J Exp Med* 185:1307.
10. Anderton, S. M., R. van der Zee, B. Prakken, A. Noordzij, and W. van Eden. 1995. Activation of T cells recognizing self 60-kD heat shock protein can protect against experimental arthritis. *J Exp Med* 181:943.
11. Yang, X. D., J. Gasser, and U. Feige. 1992. Prevention of adjuvant arthritis in rats by a nonapeptide from the 65-kD mycobacterial heat-shock protein: specificity and mechanism. *Clin Exp Immunol* 87:99.
12. van Eden, W., U. Wendling, L. Paul, B. Prakken, P. van Kooten, and R. van der Zee. 2000. Arthritis protective regulatory potential of self-heat shock protein cross-reactive T cells. *Cell Stress Chaperones* 5:452.
13. Lopez-Guerrero, J. A., J. P. Lopez-Bote, M. A. Ortiz, R. S. Gupta, E. Paez, and C. Bernabeu. 1993. Modulation of adjuvant arthritis in Lewis rats by recombinant vaccinia virus expressing the human 60-kilodalton heat shock protein. *Infect Immun* 61:4225.
14. Lopez-Guerrero, J. A., M. A. Ortiz, E. Paez, C. Bernabeu, and J. P. Lopez-Bote. 1994. Therapeutic effect of recombinant vaccinia virus expressing the 60-kd heat-shock protein on adjuvant arthritis. *Arthritis Rheum* 37:1462.
15. Quintana, F. J., P. Carmi, F. Mor, and I. R. Cohen. 2002 Inhibition of adjuvant arthritis by a DNA vaccine encoding human heat shock protein 60. *J Immunol* 169:3422.
16. Anderton, S. M., R. van der Zee, A. Noordzij, and W. van Eden. 1994. Differential mycobacterial 65-kDa heat shock protein T cell epitope recognition after adjuvant arthritis-inducing or protective immunization protocols. *J Immunol* 152:3656.
17. Quintana, F. J., A. Rotem, P. Carmi, and I. R. Cohen. 2000. Vaccination with empty plasmid DNA or CpG oligonucleotide inhibits diabetes in nonobese diabetic mice: modulation of spontaneous 60-kDa heat shock protein autoimmunity. *J Immunol* 165:6148.

What is claimed is:

1. A method of treating a T cell-mediated inflammatory autoimmune disease in an individual, the method comprising:
   administering by intramuscular injection to an individual having a T cell-mediated inflammatory autoimmune disease a composition comprising a nucleic acid molecule encoding a mammalian heat shock protein 90 (HSP90), or an active fragment thereof, in an amount to provide from about 0.1 μg/kg body weight to about 200 μg/kg body weight of the nucleic acid molecule encoding the mammalian HSP90, or an active fragment thereof to the individual, wherein the nucleic acid molecule is operatively linked to one or more transcription control sequences,
   wherein the administering treats the T cell-mediated inflammatory autoimmune disease in the individual.

2. The method of claim 1, wherein the composition comprises a delivery vehicle selected from the group consisting of liposomes, micelles, and emulsions.

3. The method of claim 1, wherein the nucleic acid molecule encodes mammalian HSP 90.

4. The method of claim 3, wherein the mammalian HSP90 is human HSP90.

5. The method of claim 4, wherein the individual is a human.

6. The method of claim 5, wherein the T cell-mediated inflammatory autoimmune disease is inflammatory bowel disease and wherein the composition is administered in an amount to provide about 0.1 μg/kg body weight to about 10 μg/kg body weight of the nucleic acid molecule encoding the human HSP90.

7. The method of claim 5, wherein the T cell-mediated inflammatory autoimmune disease is ulcerative colitis.

8. The method of claim 5, wherein the T cell-mediated inflammatory autoimmune disease is Crohn's disease.

9. The method of claim 1, wherein the composition is administered in an amount to provide about 0.5 μg/kg body weight to about 200 μg/kg body weight of the nucleic acid molecule encoding the mammalian HSP90, or an active fragment thereof to the individual.

10. The method of claim 9, wherein the nucleic acid molecule encodes mammalian HSP 90.

11. The method of claim 10, wherein the mammalian HSP90 is human HSP90.

12. The method of claim 11, wherein the individual is a human.

13. The method of claim 6, wherein the inflammatory bowel disease is ulcerative colitis.

14. The method of claim 6, wherein the inflammatory bowel disease is Crohn's disease.

15. The method of claim 1, wherein the composition is administered in an amount to provide about 0.1 μg/kg body weight to about 10 μg/kg body weight of the nucleic acid molecule encoding the mammalian HSP90, or an active fragment thereof to the individual.

* * * * *